(12) United States Patent
Bakaletz et al.

(10) Patent No.: US 11,690,892 B2
(45) Date of Patent: Jul. 4, 2023

(54) HU SPECIFIC INTERFERING AGENTS

(71) Applicant: Research Institute at Nationwide Children's Hospital, Columbus, OH (US)

(72) Inventors: Lauren O. Bakaletz, Hilliard, OH (US); Steven D. Goodman, Hilliard, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 246 days.

(21) Appl. No.: 15/952,129

(22) Filed: Apr. 12, 2018

(65) Prior Publication Data

US 2018/0303900 A1 Oct. 25, 2018

Related U.S. Application Data

(63) Continuation of application No. PCT/US2016/057237, filed on Oct. 14, 2016.

(60) Provisional application No. 62/241,670, filed on Oct. 14, 2015, provisional application No. 62/242,235, filed on Oct. 15, 2015, provisional application No. 62/347,551, filed on Jun. 8, 2016.

(51) Int. Cl.

| | |
|---|---|
| A61K 39/02 | (2006.01) |
| A61K 39/09 | (2006.01) |
| A61K 38/16 | (2006.01) |
| A61K 9/16 | (2006.01) |
| A61K 35/744 | (2015.01) |
| A61K 47/69 | (2017.01) |
| C07K 14/315 | (2006.01) |
| C07K 16/12 | (2006.01) |
| A61K 47/36 | (2006.01) |

(52) U.S. Cl.
CPC ............ *A61K 38/16* (2013.01); *A61K 9/1652* (2013.01); *A61K 35/744* (2013.01); *A61K 39/092* (2013.01); *A61K 47/36* (2013.01); *A61K 47/6921* (2017.08); *C07K 14/315* (2013.01); *C07K 16/1275* (2013.01); *A61K 39/0216* (2013.01)

(58) Field of Classification Search
None
See application file for complete search history.

(56) References Cited

U.S. PATENT DOCUMENTS

| | | | |
|---|---|---|---|
| 4,659,678 A * | 4/1987 | Forrest ................. | G01N 33/544 436/512 |
| 4,914,023 A * | 4/1990 | Philo ..................... | G01N 33/581 436/500 |
| 5,549,908 A | 8/1996 | Smith et al. | |
| 6,486,314 B1 | 11/2002 | Van Geel-Schutten et al. | |
| 6,551,795 B1 | 4/2003 | Rubenfield et al. | |
| 6,846,651 B2 | 1/2005 | Fleischmann et al. | |
| 7,241,867 B2 | 7/2007 | Bakaletz et al. | |
| 7,413,868 B2 | 8/2008 | Kauvar et al. | |
| 7,435,595 B2 | 10/2008 | Boehm et al. | |
| 7,638,282 B2 | 12/2009 | Bakaletz et al. | |
| 7,811,591 B2 | 10/2010 | Bakaletz et al. | |
| 7,816,086 B2 | 10/2010 | Bakaletz et al. | |
| 7,939,344 B2 | 5/2011 | Kauvar et al. | |
| 7,981,676 B2 | 7/2011 | Boehm et al. | |
| 7,998,490 B2 | 8/2011 | Bakaletz et al. | |
| 8,236,494 B2 | 8/2012 | Bakaletz et al. | |
| 8,283,114 B2 | 10/2012 | Bakaletz et al. | |
| 8,329,187 B2 | 12/2012 | Lazzari et al. | |
| 8,628,917 B2 | 1/2014 | Bakaletz et al. | |
| 8,652,773 B2 | 2/2014 | Bakaletz et al. | |
| 8,758,764 B2 | 6/2014 | Masignani et al. | |
| 8,933,029 B2 | 1/2015 | McNicol et al. | |
| 8,999,291 B2 | 4/2015 | Goodman et al. | |
| 9,017,656 B2 | 4/2015 | Hancock et al. | |
| 9,034,642 B2 | 5/2015 | Bakaletz et al. | |
| 9,155,792 B2 | 10/2015 | Cottarel et al. | |
| 9,278,069 B2 | 3/2016 | Berkland et al. | |
| 9,504,739 B2 | 11/2016 | Berkes et al. | |
| 9,554,590 B2 | 1/2017 | Quintens et al. | |
| 9,603,878 B2 | 3/2017 | Berry et al. | |
| 9,610,307 B2 | 4/2017 | Berry et al. | |
| 9,687,449 B2 | 6/2017 | Harel | |

(Continued)

FOREIGN PATENT DOCUMENTS

| | | |
|---|---|---|
| DE | 20 2013 103 204 U1 | 9/2013 |
| WO | WO-98/50018 A1 | 11/1998 |

(Continued)

OTHER PUBLICATIONS

Wu et al. Nanoscale Res. Lett. 8: 197, 1-8, 2013.*

(Continued)

*Primary Examiner* — S. Devi

(74) *Attorney, Agent, or Firm* — Foley & Lardner LLP

(57) ABSTRACT

Methods of and compositions for breaking down a biofilm or inhibiting, preventing or treating a microbial infection that produces a biofilm are disclosed, which involves administration of an interfering agent capable of specifically competing, titrating, or inhibiting the binding of an HU protein to a microbial DNA. By competing with HU proteins that bind to DNA scaffold in the biofilm, these interfering agents destabilize the biofilm leading to destruction and removal of the biofilm by the immune system. Further method and composition aspects are contemplated in relation to infections caused by bacteria that export an HU protein.

15 Claims, 5 Drawing Sheets

Specification includes a Sequence Listing.

(56) References Cited

U.S. PATENT DOCUMENTS

| | | |
|---|---|---|
| 9,713,631 B2 | 7/2017 | Berkes et al. |
| 9,717,765 B2 | 8/2017 | Berkes et al. |
| 9,745,366 B2 | 8/2017 | Goodman et al. |
| 10,233,234 B2 | 3/2019 | Kauvar et al. |
| 10,369,176 B2 | 8/2019 | Goodman et al. |
| 10,570,193 B2 | 2/2020 | Kauvar et al. |
| 10,624,934 B2 | 4/2020 | Goodman et al. |
| 10,642,934 B2 | 5/2020 | Heck et al. |
| 11,104,723 B2 | 8/2021 | Goodman et al. |
| 2002/0132753 A1 | 9/2002 | Rosen et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0059633 A1 | 3/2005 | Van Geel-Schuten et al. |
| 2005/0112235 A1 | 5/2005 | Shefer et al. |
| 2005/0131222 A1 | 6/2005 | Fleischmann et al. |
| 2005/0170504 A1 | 8/2005 | Boehm et al. |
| 2005/0221439 A1 | 10/2005 | Bakaletz et al. |
| 2005/0266069 A1 | 12/2005 | Simmons et al. |
| 2006/0030539 A1 | 2/2006 | Nick et al. |
| 2006/0228384 A1 | 10/2006 | Eldridge |
| 2006/0240045 A1 | 10/2006 | Berthet et al. |
| 2007/0207210 A1 | 9/2007 | Brown et al. |
| 2007/0264256 A1 | 11/2007 | Bakaletz et al. |
| 2007/0286822 A1 | 12/2007 | Sanders et al. |
| 2009/0155912 A1 | 6/2009 | Boehm et al. |
| 2009/0297555 A1 | 12/2009 | Kemble et al. |
| 2009/0324651 A1 | 12/2009 | Old et al. |
| 2010/0166771 A1 | 7/2010 | Bakaletz et al. |
| 2010/0291177 A1 | 11/2010 | Hermans et al. |
| 2010/0303723 A1 | 12/2010 | Farokhzad et al. |
| 2010/0310569 A1 | 12/2010 | Bakaletz et al. |
| 2011/0008493 A1 | 1/2011 | Zorea |
| 2011/0027328 A1 | 2/2011 | Baig et al. |
| 2011/0135646 A1 | 6/2011 | Bakaletz et al. |
| 2011/0236306 A1 | 9/2011 | Goodman et al. |
| 2012/0128701 A1 | 5/2012 | Goodman et al. |
| 2012/0148615 A1 | 6/2012 | Masignani et al. |
| 2012/0189558 A1 | 7/2012 | Prendergast |
| 2012/0247993 A1 | 10/2012 | Palazzi et al. |
| 2013/0017204 A1 | 1/2013 | Bakaletz et al. |
| 2013/0078254 A1 | 3/2013 | Bakaletz et al. |
| 2013/0183323 A1 | 7/2013 | Wang |
| 2014/0010918 A1 | 1/2014 | Quintens et al. |
| 2014/0120107 A1 | 5/2014 | Bakaletz et al. |
| 2014/0127221 A1 | 5/2014 | Bakaletz et al. |
| 2014/0287426 A1 | 9/2014 | Arnold et al. |
| 2014/0356389 A1 | 12/2014 | Masignani et al. |
| 2015/0010654 A1 | 1/2015 | Arnold et al. |
| 2015/0086561 A1 | 3/2015 | Kauvar et al. |
| 2015/0110838 A1 | 4/2015 | Agrawal |
| 2015/0166641 A1 | 6/2015 | Goodman et al. |
| 2015/0197558 A1 | 7/2015 | Kauvar et al. |
| 2015/0216971 A1 | 8/2015 | Rotolo et al. |
| 2015/0218231 A1 | 8/2015 | Bakaletz et al. |
| 2015/0290140 A1 | 10/2015 | Singh et al. |
| 2015/0299298 A1 | 10/2015 | Kauvar et al. |
| 2015/0342848 A1 | 12/2015 | Bhushan et al. |
| 2016/0089363 A1 | 3/2016 | Borody |
| 2016/0095316 A1 | 4/2016 | Goodman et al. |
| 2016/0143961 A1 | 5/2016 | Berry et al. |
| 2016/0175440 A1 | 6/2016 | Goodman et al. |
| 2016/0193258 A1 | 7/2016 | Berry et al. |
| 2016/0194384 A1 | 7/2016 | Goodman et al. |
| 2016/0199424 A1 | 7/2016 | Berry et al. |
| 2016/0223553 A1 | 8/2016 | Sears et al. |
| 2016/0235792 A1 | 8/2016 | Berry et al. |
| 2016/0244489 A1 | 8/2016 | Masignani et al. |
| 2016/0271188 A1 | 9/2016 | Berry et al. |
| 2016/0289278 A1 | 10/2016 | Bakaletz et al. |
| 2017/0056454 A1 | 3/2017 | Berkes et al. |
| 2017/0056455 A1 | 3/2017 | Berkes et al. |
| 2017/0128502 A1 | 5/2017 | Berkes et al. |
| 2017/0196914 A1 | 7/2017 | McKenzie et al. |
| 2017/0196915 A1 | 7/2017 | Czarnecki-Maulden et al. |
| 2017/0197028 A1 | 7/2017 | Goldsmith |
| 2017/0215417 A1 | 8/2017 | Bhushan et al. |
| 2017/0216377 A1 | 8/2017 | Berkes et al. |
| 2017/0281699 A1 | 10/2017 | Berkes et al. |
| 2017/0296600 A1 | 10/2017 | Rangavajla |
| 2018/0071344 A1 | 3/2018 | Berry et al. |
| 2018/0207067 A1 | 7/2018 | Goodman et al. |
| 2018/0221422 A1 | 8/2018 | Keshtmand et al. |
| 2019/0000971 A1 | 1/2019 | Bakaletz et al. |
| 2019/0040127 A1 | 2/2019 | Wadehra et al. |
| 2019/0055304 A1 | 2/2019 | Kauvar et al. |
| 2019/0337996 A1 | 11/2019 | Bakaletz et al. |
| 2019/0338018 A1 | 11/2019 | Bakaletz et al. |
| 2019/0388309 A1 | 12/2019 | Goodman et al. |
| 2020/0002409 A1 | 1/2020 | Goodman et al. |
| 2020/0155620 A1 | 5/2020 | Goodman et al. |
| 2021/0206841 A1 | 7/2021 | Goodman et al. |
| 2021/0228716 A1 | 7/2021 | Bakaletz et al. |

FOREIGN PATENT DOCUMENTS

| | | |
|---|---|---|
| WO | WO-02/077183 A2 | 10/2002 |
| WO | WO-03/083045 A2 | 10/2003 |
| WO | WO-2004/014418 A2 | 2/2004 |
| WO | WO-2005/111066 A2 | 11/2005 |
| WO | WO-2006/017816 A2 | 2/2006 |
| WO | WO-2006/138527 A2 | 12/2006 |
| WO | WO-2009/006699 A1 | 1/2009 |
| WO | WO-2010/138522 A2 | 12/2010 |
| WO | WO-2010/139956 A1 | 12/2010 |
| WO | WO-2011/123396 A1 | 10/2011 |
| WO | WO-2012/034090 A1 | 3/2012 |
| WO | WO-2013/088045 A1 | 6/2013 |
| WO | WO-2014/016417 A1 | 1/2014 |
| WO | WO-2014/067976 A1 | 5/2014 |
| WO | WO-2014/121304 A1 | 8/2014 |
| WO | WO-2014/201305 A1 | 12/2014 |
| WO | WO-2015/038339 A1 | 3/2015 |
| WO | WO-2015/048484 A2 | 4/2015 |
| WO | WO-2015/089502 A2 | 6/2015 |
| WO | WO-2016/154491 A1 | 9/2016 |
| WO | WO-2017/066719 A2 | 4/2017 |
| WO | WO-2017/192594 A1 | 11/2017 |
| WO | WO-2018/187615 A1 | 10/2018 |

OTHER PUBLICATIONS

Actor JK. In: Introductory Immunology, Chapter 12, pp. 135-152, 2014.*

Franssen et al. J. Controllled Release 60: 211-221, 1999.*

Goshima et al. Gene 118: 97-102, 1992.*

U.S. Appl. No. 16/297,094, filed Mar. 8, 2019, Goodman et al.

U.S. Appl. No. 16/746,708, filed Jan. 17, 2020, Trellis Bioscience, LLC.

Adams et al., "D-158. Epitope-mapping the immune response of children with otitis media and adults with chronic obstructive pulmonary disease to the PilA protein of nontypeable Haemophilus influenzae type IV pilus," 107th General Meeting, American Society for Microbiology; Toronto, ON, 2007, 1 page.

Adams et al., "Epitope-mapping the immune response of children with otitis media and adults with chronic obstructive pulmonary disease to the PilA protein of nontypeable Haemophilus influenzae type IV pilus," Immunology, 9th International Symposium on Recent Advances in Otitis Media; St. Pete Beach, FL, 2007, p. 356, 1 page.

Albandar, "Epidemiology and risk factors of periodontal diseases", Dental clinics of North America, vol. 49, No. 3, Jun. 28, 2005, pp. 517-532.

Bakaletz et al., "New strategies to target bacterial biofilms", 28th Annual North American Cystic Fibrosis Conference (NACFC), Atlanta, GA, Oct. 9-11, 2014 (presentation), 2 pages.

Bakaletz et al., "Relative immunogenicity and efficacy of two synthetic chimeric peptides of fimbrin as vaccinogens against nasopharyngeal colonization by nontypeable Haemophilus influenzae in the chinchilla," Vaccine, vol. 15, No. 9, 1997, pp. 955-961.

(56) References Cited

OTHER PUBLICATIONS

Bakaletz et al., "Protection against Development of Otitis Media Induced by Nontypeable Haemophilus influenzae by Both Active and Passive Immunization in a Chinchilla Model of Virus-Bacterium Superinfection," Infecion and Immunity, vol. 67, No. 6, Jun. 1999, pp. 2746-2762.

Bakaletz, "Biofilms can be dispersed by focusing the immune system on a common family of bacterial nucleoid associated proteins", 6th ASM Conference on Biofilms, Miami, FL, Sep. 29-Oct. 4, 2012 (presentation), 5 pages.

Bakaletz, L.O., Targeting the biofilm for development of novel preventative and therapeutic vaccine candidates to prevent otitis media, 6th ASM Conference on Biofilms, Miami, FL, Sep. 29-Oct. 4, 2012 (presentation), 5 pages.

Bass, J.I.F. et al. (2010) "Extracellular DNA: A Major Proinflammatory Component of Pseudomonas aeruginosa Biofilms," The Journal of Immunology 184:6386-6395.

Beech, I.B. et al. (2005) "Microbe-surface interactions in biofouling and biocorrosion processes," International Microbiology 8:157-168.

Bjarnsholt, T. (2013) "The role of bacterial biofilms in chronic infections," APMIS 121(Suppl. 136):1-51.

Boles, B.R. et al. (2011) "Staphylococcal biofilm disassembly," Trends in Microbiology 19(9):449-455.

Brady, R.A. et al. (2006) "Identification of Staphylococcus aureus Proteins Recognized by the Antibody-Mediated Immune Response to a Biofilm Infection," Infection and Immunity 74(6):3415-3426.

Brandstetter et al., "Antibodies Directed Against Integration Host Factor Mediate Biofilm Clearance From Nasopore," The Laryngoscope, vol. 12, No. 11, Nov. 2013, pp. 2626-2632.

Brinkmann V, Reichard U, Goosmann C, Fauler B, Uhlemann Y, Weiss DS, Weinrauch Y, Zychlinsky A. Neutrophil extracellular traps kill bacteria. Science. 2004;303(5663):1532-5. doi: 10.1126/science.1092385. PubMed PMID: 15001782.

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258, Supplementary Material, 6 pages.

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258.

Brockson ME, Novotny LA, Mokrzan EM, Malhotra S, Jurcisek JA, Akbar R, Devaraj A, Goodman SD, Bakaletz LO, Evaluation of the kinetics and mechanism of action of anti-integration host factor-mediated disruption of bacterial biofilms. Molecular microbiology. 2014;93(6): 1246-58. Epub Jul. 30, 2014, doi: 10.1 1 1 1/mmi.12735, PubMed PMID: 25069521 ; PMCID: 4160410.

Catlin, "Extracellular Deoxyribonucleic Acid of Bacteria and a Deoxyribonuclease Inhibitor," Science, vol. 124, Sep. 7, 1956, pp. 441-442.

Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.

Chen et al., "Novel Strategies for the Prevention and Treatment of Biofilm Related Infections," Int. J. Mol. Sci., vol. 14, Sep. 6, 2013, pp. 18488-18501.

Chen, C. et al. (2004) "Substrate specificity of Helicobacter pylori histone-like HU protein is determined by insufficient stabilization of DNA flexure points," Biochem J. 383:343-351.

Coenye, T. et al. (2010) "In vitro and in vivo model systems to study microbial biofilm formation," Journal of Microbiological Methods 83:89-105.

Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.

Collarini, E.J. et al. (2009) "Potent High-Affinity Antibodies for Treatment and Prophylaxis of Respiratory Syncytial Virus Derived from B Cells of Infected Patients," J Immunol 183:6338-6345.

Dalai, B. et al. (2009) "Histone-like protein H-NS regulates biofilm formation and virulence of Actinobacillus pheuropneumonia," Microbial Pathogenesis 46:128-134.

Darouiche, R.O. et al. (2004) "Treatment of Infections Associated with Surgical Implants," N Engl J Med 350:1422-1429.

Darveau RP. The oral microbial consortium's interaction with the periodontal innate defense system. DNA and cell biology. 2009;28(8):389-95. Epub May 14, 2009. doi:10.1089/dna.2009.0864. PubMed PMID: 19435427; PMCID: 2883565.

Darveau, "Periodontitis: a polymicrobial disruption of host homeostasis", Nature reviews Microbiology, vol. 8, No. 7, Jul. 2010, pp. 481-490.

De La Fuente-Nunez et al., "Broad-Spectrum Anti-biofilm Peptide That Targets a Cellular Stress Response," PLoS Pathog., vol. 10, No. 5, May 2014, pp. 1-12.

Devaraj A, justice SS, Bakaletz LO, Goodman SD. DNABII proteins play a central role in UPEC biofilm structure. Molecular microbiology. 2015. doi: 10.1111/mmi.12994. PubMed PMID: 25757804.

Devaraj et al., "DNABII proteins play a central role in UPEC biofilm structure", Molecular Microbiology, 2017, vol. 96, vol. 6, Jun. 2015, pp. 1119-1135.

Dominguez-Herrera, J. et al. (2011) "Efficacy of Daptomycin versus Vancomycin in an Experimental Model of Foreign-Body and Systemic Infection Caused by Biofilm Producers and Methicillin-Resistant *Staphylococcus epidermidis*," Antimicrobial Agents and Chemotherapy 56(2):613-617.

Donlan, R.M. et al. (2002) "Biofilms: Survival Mechanisms of Clinically Relevant Microorganisms," Clinical Microbiology Reviews 15(2):167-193.

Durocher et al., "High-level and high-throughput recombinant protein production by transient transfection of suspension-growing human 293-EBNA1 cells," Nucleic Acids Research, vol. 30, No. 2, e9, Nov. 11, 2001, 9 pages.

Dzink et al., "The predominant cultivable microbiota of active and inactive lesions of destructive periodontal diseases", Journal of clinical periodontology, vol. 15, No. 5, Sep. 8, 1987, pp. 316-323.

Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.

Eke PI, Dye BA, Wei L, Thornton-Evans GO, Genco RJ, CDC Periodontal Disease Surveillance workgroup: James Beck GDRP. Prevalence of periodontitis in adults in the United States: 2009 and 2010. Journal of dental research.2012;91(10):914-20. Epub Sep. 1, 2012. doi: 10.1177/0022034512457373. PubMed PMID: 22935673.

Extended European Search Report issued in EP Application No. 16856372.4 dated Jun. 7, 2019, 8 pages.

Fedorov, O. et al. (2012) "Kinase Inhibitor Selectivity Profiling Using Differential Scanning Fluorimetry," Kinase Inhibitors: Methods and Protocols, Methods in Molecular Biology 795:109-118.

Garcia-Contreras et al., "Protein Translation and Cell Death: The Role of Rare tRNAs in Biofilm Formation and in Activating Dormant Phage Killer Genes," PLoS ONE, vol. 3, No. 6, Jun. 11, 2008, e2394, 17 pages.

George et al., "Cystic fibrosis infections: treatment strategies and prospects," FEMS Microbiol Lett., vol. 300, Jun. 15, 2009, pp. 153-164.

Goldenberg et al., "Genetic and biochemical analysis of IHF/HU hybrid proteins", BioChimie, vol. 76, No. 10-11, Jan. 1, 1994, pp. 941-950.

Goodman et al., "Biofilms can be dispersed by focusing the immune system on a common family of bacterial nucleoid-associated proteins," Mucosal Immunology, vol. 4, No. 6, Nov. 2011, pp. 625-637.

Goodman et al., "In Vitro Selection of Integration Host Factor Binding Sites," Journal of Bacteriology, vol. 181, No. 10, May 1999, pp. 3246-3255.

Goodman et al., "Replacement of Integration Host Factor Protein-induced DNA Bending by Flexible Regions of DNA," The Journal of Biological Chemistry, vol. 274, No. 52, Aug. 6, 1999, pp. 37004-37011.

Goodman S D et al., "Biofilms can be dispersed by focusing the immune system on a common family of bacterial nucleoid-

(56) References Cited

OTHER PUBLICATIONS associated proteins", Mucosal Immuno, Nature Publishing Group, vol. 4, No. 6, Nov. 1, 2011, pp. 625-637.
Goodman SD, Obergfell KP, Jurcisek JA, Novotny LA, Downey JS, Ayala EA, Tjokro N, Li B, Justice SS, Bakaletz LO. Biofilms can be dispersed by focusing the immune system on a common family of bacterial nucleoid-associated proteins. Mucosal immunology. 2011;4(6):625-37. Epub Jul. 1, 2011. doi: 10.1038/mi.2011.27. PubMed PMID: 21716265,.
Goodman, "A new immunotherapeutic approach that disperses biofilms, Banff Conference on Infectious Diseases", Banff, Alberta, Canada, May 18, 2012 (presentation), 9 pages.
Goodman, "Making and breaking biofilms", Ohio Branch American Society for Microbiology Annual Meeting, Columbus, OH, Apr. 11-12, 2014 (presentation), 12 pages.
Goodman, "Nucleoprotein complexes in the extracellular matrix are critical for the structural integrity of bacterial biofilms", 112th General Meeting, American Society for Microbiology, San Francisco, CA, Jun. 18, 2012 (presentation), 9 pages.
Goodman, "The DNABII family of proteins: Diagnostic markers and therapeutic targets of bacterial biofilms", International Congress on Bacteriology and Infectious Disease, Baltimore, MD, Nov. 21, 2013, 7 pages.
Goshima et al., "Chimeric HU-IHF proteins that alter DNA-binding ability," GENE, vol. 118, No. 1, Sep. 1, 1992, pp. 97-102.
Govan et al., "Microbial pathogenesis in cystic fibrosis: mucoid Pseudomonas aeruginosa and Burkholderia cepacia," Microbiol. Rev., vol. 60, No. 3, Sep. 1996, pp. 539-574.
Grossi et al., "Assessment of risk for periodontal disease. I. Risk indicators for attachment loss", Journal of periodontology, vol. 65, No. 3, Sep. 15, 1993, pp. 260-267.
Gustave et al., "Targeting bacterial integration host factor to disrupt biofilms associated with cystic fibrosis," Journal of Cystic Fibrosis, vol. 12, No. 4, Nov. 17, 2012, pp. 384-389.
Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster), 1 page.
Gustave JE, Jurcisek JA, McCoy KS, Goodman SD, Bakaletz LO. Targeting bacterial integration host factor to disrupt biofilms associated with cystic fibrosis. Journal of cystic fibrosis : official journal of the European Cystic Fibrosis Society.2013;12(4):384-9. Epub Nov. 22, 2012. doi: 10.1016/j.jcf.2012.10.011. PubMed PMID: 23168017; PMCID: 3582735.
Hajishengallis G, Darveau RP, Curtis MA. The keystone-pathogen hypothesis. Nature reviews Microbiology.2012;10(10):717-25. Epub Sep. 4, 2012. doi:10.1038/nrmicro2873. PubMed PMID: 22941505; PMCID: 3498498.
Hajishengallis G, Lambris JD. Microbial manipulation of receptor crosstalk in innate immunity. Nature reviews Immunology. 2011;11(3):187-200. Epub Feb. 26, 2011. doi:10.1038/nri2918. PubMed PMID: 21350579; PMCID: 3077082.
Hajishengallis G, Liang S, Payne MA, Hashim A, Jotwani R, Eskan MA, McIntosh ML, Alsam A, Kirkwood KL, Lambris JD, Darveau RP, Curtis MA. Low-abundance biofilm species orchestrates inflammatory periodontal disease through the commensal microbiota and complement. Cell host & microbe.2011;10(5):497-506. Epub Nov. 1, 2011.
Hall-Stoodley et al., "Bacterial Biofilms: From the Natural Environment to Infectious Diseases," Nature Reviews, Microbiology, vol. 2, Feb. 2004, pp. 95-108.
Hall-Stoodley et al., "Direct Detection of Bacterial Biofilms on the Middle-Ear Mucosa of Children With Chronic Otitis Media," JAMA, vol. 296, No. 2, Jun. 1, 2007, pp. 202-211.
Hall-Stoodley et al., "Evolving concepts in biofilm infections", Cellular Microbiology, vol. 11, No. 7, 2009, pp. 1034-1043.
Haluzi et al., "Genes Coding for Integration Host Factor Are Conserve in Gram-Negative Bacteria," Journal of Bacteriology, vol. 173, No. 19, Oct. 1991, pp. 6297-6299.

Harriman, W.D. et al. (2008) "Antibody discovery via multiplexed single cell characterization," Journal of Immunological Methods 341:135-145.
Harrison, J.J. et al. (2010) "Microtiter susceptibility testing of microbes growing on peg lids: a miniaturized biofilm model for high-throughput screening," Nature Protocols 5(7):1236-1254.
Haruta et al., "A possible role of histone-like DNA-binding protein of *Streptococcus intermedius* in the pathogenesis of bile duct damage in primary biliary cirrhosis," Clinical Immunology, vol. 127, No. 2, Mar. 11, 2008, pp. 245-251.
Haruta et al.,"Long-term bacterial exposure can trigger nonsuppurative destructive cholangitis associated with multifocal epithelial inflammation," Laboratory Investigation, vol. 90, Apr. 2010, pp. 577-588.
Hoyle et al., "Bacterial Resistance to Antibiotics: The Role of Biofilms," Prog. Drug Res., vol. 37, 1991, pp. 91-105.
Janeway, "Manipulating the immune response to fight infection," Immunobiology: The Immune System in Health and Disease, 5th ed.; retrieved online from https://www.ncbi.nlm.nih.gov/books/NBK27131/, 2001, 13 pages.
Jiao et al., "Identification of Biofilm Matrix-Associated Proteins from an Acid Mine Drainage Microbial Community," Appl & Environ Microbiol., vol. 77, Aug. 2011, pp. 5230-5237.
John, A-K. et al. (2011) "Reversible Daptomycin Tolerance of Adherent Staphylococci in an Implant Infection Model," Antimicrobial Agents and Chemotherapy 55(7):3510-3516.
Johnson et al., "Chapter 8: Bending and Compaction of DNA by Proteins," Protein-Nucleic Acid Interactions: Structural Biology, 2008, pp. 176-220.
Joo, H-S. et al. (2012) "Molecular Basis of In Vivo Formation by Bacterial Pathogens," Chemistry & Biology 19:1503-1513.
Jurcisek et al., "Role of Sialic Acid and Complex Carbohydrate Biosynthesis in Biofilm Formation by Nontypeable Haemophilus influenzae in the Chinchilla Middle Ear," Infection and Immunity, vol. 73, Jun. 2005, pp. 3210-3218.
Jurcisek et al., "Biofilms Formed by Nontypeable Haemophilus influenzae In Vivo Contain both Double-Stranded DNA and Type IV Pilin Protein," Journal of Bacteriology, vol. 189, No. 10, Feb. 15, 2007, pp. 3868-3875.
Jurcisek JA, Bakaletz LO. Biofilms formed by nontypeable Haemophilus influenzae in vivo contain both double-stranded DNA and type IV pilin protein. Journal of bacteriology.2007;189(10):3868-75. Epub Feb. 27, 2007. doi: 10.1128/JB.01935-06. PubMed PMID: 17322318; PMCID: 1913342.
Justice et al., "Aberrant Community Architecture and Attenuated Persistence of Uropathogenic *Escherichia coli* in the Absence of Individual IHF Subunits," PLoS ONE, vol. 7, No. 10, Oct. 2012, pp. 1-11.
Kamashev D, Rouviere-Yaniv J. The histone-like protein HU binds specifically to DNA recombination and repair intermediates. The EMBO journal.2000;19(23):6527-35.
Kamashev et al., "The histone-like protein HU binds specifically to DNA recombination and repair intermediates," The EMBO Journal, vol. 19, No. 23, Oct. 13, 2000, pp. 6527-6535.
Kennedy et al., "Passive Transfer of Antiserum Specific for Immunogens Derived from a Nontypeable Haemophilus influenzae Adhesin and Lipoprotein D Prevents Otitis Media after Heterologous Challenge," Infection and Immunity, vol. 68, No. 5, May 2000, pp. 2756-2765.
Khrapunov, S. et al. (2006) "Binding then bending: A mechanism for wrapping DNA," PNAS 103(51):19217-19218.
Kim et al., "Beta-Arm flexibility of HU from *Staphylococcus aureus* dictates the DNA-binding and recognition mechanism," Acta Cryst., D70, Oct. 30, 2014, pp. 3273-3289.
Kim et al., "Proteins Released by Helicobacter pylori In Vitro," Journal of Bacteriology, vol. 184, No. 22, Nov. 2002, pp. 6155-6162.
Kirketerp-Moller et al., "Distribution, Organization, and Ecology of Bacteria in Chronic Wounds," Journal of Clinical Microbiology, vol. 46, No. 8, Aug. 2008, pp. 2717-2722.
Kristian, S.A. et al. (2003) "Alanylation of Teichoic Acids Protects *Staphylococcus aureus* against Toll-like Receptor 2-Dependent Host

(56) References Cited

OTHER PUBLICATIONS

Defense in a Mouse Tissue Cage Infection Model," The Journal of Infectoius Diseases 188:414-423.
Kyd et al., "Efficacy of the 26-Kilodalton Outer Membrane Protein and Two P5 Fimbrin-Derived Immunogens to Induce Clearance of Nontypeable Haemophilus influenzae from the Rat Middle Ear and Lungs as Well as from the Chinchilla Middle Ear and Nasopharynx," Infection and Immunity, vol. 71, No. 8, Aug. 2003, pp. 4691-4699.
Lamont RJ, Jenkinson HF. Life below the gum line: pathogenic mechanisms of Porphyromonas gingivalis. Microbiology and molecular biology reviews: MMBR.1998;62(4):1244-63. Epub Dec. 5, 1998. PubMed PMID: 9841671; PMCID: 98945.
Lappann M, Claus H, van Alen T, Harmsen M, Elias J, Molin S, Vogel U. A dual role of extracellular DNA during biofilm formation of Neisseria meningitidis. Molecular microbiology.2010;75(6):1355-71. doi: 10.1111/j.1365-2958.2010.07054.x. PubMed PMID: 20180907.
Lebeaux et al., "From in vitro to in vivo Models of Bacterial Biofilm-Related Infections," Pathogens, vol. 2, May 13, 2013, pp. 288-356.
Liu et al., "The essentiality and involvement of *Streptococcus intermedius* histone-like DNA-binding protein in bacterial viability and normal growth," Molecular Microbiology, vol. 68, No. 5, Apr. 21, 2008, pp. 1268-1282.
Liu, D. et al. (2008) "Histone-like DNA binding protein of *Streptococcus intermedius* induces the expression of pro-inflammatory cytokines in human monocytes via activation of ERK1/2 and JNK pathways," Cellular Microbiology 10(1):262-276.
Lunsford et al., "DNA-Binding Activities in *Streptococcus gordonii*: Indentification of a Receptor-Nickase and a Histonelike Protein," Current Microbiology, vol. 32, 1996, pp. 95-100.
M. Elizabeth Brockson et al., "Evaluation of the kinetics and mechanism of action anti-integration host factor-mediated disruption of bacterial biofilms: Anti-IHF-mediated biofilm collapse", Molecular Microbiology., Aug. 19, 2014, pp. 1-22.
Maeda et al., "Oral streptococcal glyceraldehyde-3-phosphate dehydrogenase mediates interaction with Porphyromonas gingivalis fimbriae", Microbes and infection / Institut Pasteur., vol. 6, No. 13, Sep. 11, 2004, pp. 1163-1170.
Malhotra et al., "Defining the functional epitopes of Integration Host Factor (IHF) to develop a novel biofilm-focused immunotherapeutic against nontypeable Haemophilus influenzae-induced chronic and recurrent otitis media", 18th International Symposium on Recent Advances in Otitis Media, National Harbor, MD, Jun. 7-11, 2015 (poster), 1 page.
Malhotra et al., "Fine mapping the functional epitopes within integration host factor, a novel therapeutic target for nontypeable Haemophilus influenza-induced diseases of the respiratory tract", Abst. 12th Annual AMA Research Symposium, Dallas, TX, Nov. 7, 2014, 1 page.
Malhotra et al., Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster),1 page.
Malhotra et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013, 20 pages.
Malhotra et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).
Mann, E.E. et al. (2009) "Modulation of eDNA Release and Degradation Affects *Staphylococcus aureus* Biofilm Maturation," PLoS ONE 4(6):e5822, 1-12.
Martinez-Antonio A et al. (2008), "Functional organization of *Escherichia coli* transcriptional regulatory network", J. Mol. Biol. vol. 381, p. 238-247.
Meluleni et al., (1995) "Mucoid Pseudomonas aeruginosa Growing in a Biofilm In Vitro Are Killed by Opsonic Antibodies to the Mucoid Exopolysaccharide Capsule but Not by Antibodies Produced During Chronic Lung Infection in Cystic Fibrosis Patients," J. Immunology, 155:2029-2038.
Mouw et al., "Shaping the Borrelia burgdorferi genome: crystal structure and binding properties of the DNA-bending protein Hbb," Molecular Microbiology, vol. 63, No. 5, Jan. 22, 2007, pp. 1319-1330.
Mukherjee et al., "Quantitative protein expression and cell surface characteristics of *Escherichia coli* MG1655 biofilms," Proteomics, vol. 11, Nov. 1, 2010, pp. 339-351.
Murphy et al., "Microbial Interactions in the Respiratory Tract," The Pediatric Infectious Disease Journal, vol. 28, No. 10, Oct. 2009, pp. S121-S126.
Murphy, T.F. et al. (2002) "Biofilm formation by nontypeable Haemophilus influenzae: strain variablitiy, outer membrane antigen expression and role of pili," BMC Microbiology 2:7, 1-8.
Nakagawa et al., "Clinical, microbiological and immunological studies on recurrent periodontal disease", Journal of clinical periodontology, Jul. 31, 1989, vol. 17, No. 7 Pt 1, pp. 426-434.
Novotny et al., "Antibodies against the majority subunit of Type IV pili disperse nontypeable Haemophilus influenza biofilms in a LuxS-dependent manner and confer therapeutics resolution of experimental otitis media," Mol. Microbiol., vol. 96, No. 2, Apr. 2015, pp. 1-32.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, pp. 279-289 (Dec. 10, 2009).
Novotny et al., "Structural Stability of Burkholderia cenocepacia Biofilms Is Reliant on eDNA Structure and Presence of a Bacterial Nucleic Acid Binding Protein," PLOS ONE, vol. 8, No. 6, e67629, Jun. 2013, 15 pages.
Novotny et al., "Detection and characterization of pediatric serum antibody to the OMP P5-homologous adhesin of nontypeable Haemophilus influenzae during acute otitis media," Vaccine, vol. 20, No. 29-30, Jun. 8, 2002, pp. 3590-3597.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, Aug. 22, 2009, pp. 279-289.
Novotny et al., "Epitope mapping of the Outer Membrane Protein P5-Homologous Fimbrin Adhesin of Nontypeable Haemophilus influenzae," Infection and Immunity, vol. 68, No. 4, Apr. 2000, pp. 2119-2128.
Novotny et al., "Passive immunization with human anti-protein D antibodies induced by polysaccharide protein D conjugates protects chinchillas against otitis media after intranasal challenge with Haemophilus influenzae," Vaccine, vol. 24, No. 22, Mar. 27, 2006, pp. 4804-4811.
Novotny et al., "The Fourth Surface-Exposed Region of the Outer Membrane Protein P5-Homologous Adhesin of the Nontypable Haemophilus influenzae Is an Immunodominant But Nonprotective Decoying Epitope," The Journal of Immunology, vol. 171, No. 4, Jun. 10, 2003, pp. 1978-1983.
Novotny LA, Amer AO, Brockson ME, Goodman SD, Bakaletz LO. Structural stability of Burkholderia cenocepacia biofilms is reliant on eDNA structure and presence of a bacterial nucleic acid binding protein. PloS one.2013;8(6):e67629. Epub Jun. 27, 2013. doi: 10.1371/journal.pone.0067629. PubMed PMID: 23799151; PMCID: 3682984.
Novotny, "Development of a novel biofilm-focused immunotherapeutic against NTHI-induced otitis media", 18th International Symposium on Recent Advances in Otitis Media, National Harbor, MD, Jun. 7-11, 2015 (presentation), 3 pages.
Oberto et al., "Histones, HMG, HU, IHF: Même combat," Biochimie, vol. 76, 1994, pp. 901-908.
Ordway et al., "Evaluation of Standard Chemotherapy in the Guinea Pig Model of Tuberculosis," Antimicrobial Agents and Chemotherapy, vol. 54, May 2010, pp. 1820-1833.
Otto, "*Staphylococcus epidermidis*—the 'accidental' pathogen," Nature Reviews Microbiology, vol. 7, Aug. 2009, pp. 555-567.
Park Y, Simionato MR, Sekiya K, Murakami Y, James D, Chen W, Hackett M, Yoshimura F, Demuth DR, Lamont RJ. Short fimbriae

(56) References Cited

OTHER PUBLICATIONS of Porphyromonas gingivalis and their role in coadhesion with *Streptococcus gordonii*. Infection and immunity. 2005;73(7):3983-9. Epub Jun. 24, 2005. doi: 10.1128/IAI.73.7.3983-3989.2005. PubMed PMID: 15972485; PMCID: 1168573.
PDB ID: 1IHF: Rice, P.A. et al. (1996), 1 page; retrieved online from http://www.rcsb.org/pdb/explore.do?structureId=IHF, 2 pages.
Pedulla et al., "A novel host factor for integration of mycobacteriophage L5," Proc. Natl. Acad. Sci. USA, vol. 93, Dec. 1996, pp. 15411-15416.
Percival, S.L. et al. (2015) "Biofilms and Wounds: An Overview of the Evidence," Advances in Wound Care 4(7):373-381.
Petersen et al., "Biofilm Mode of Growth of *Streptococcus intermedius* Favoreed by a Competence-Stimulating Signaling Peptide," Journal of Bacteriology, vol. 186, No. 18, Sep. 2004, pp. 6327-6331.
Petersen PE, Ogawa H. Strengthening the prevention of periodontal disease: the WHO approach. Journal of periodontology. 2005;76(12):2187-93. Epub Dec. 8, 2005. doi: 10.1902/jop.2005. 76.12.2187. PubMed PMID: 16332229.
Pethe et al., "*Mycobacterium smegmatis* laminin-binding glycoprotein shares epitopes with *Mycobacterium tuberculosis* heparin-binding haemagglutinin," Molecular Microbiology, vol. 39, No. 1, 2001, pp. 89-99.
Priyadarshini R, Cugini C, Arndt A, Chen T, Tjokro NO, Goodman SD, Davey ME, The nucleoid-associated protein ?Uß affects global gene expression in Porphyromonas gingivalis. Microbiology. 2013; 159(Pt 2):219-29.
Prymula et al., "Pneumococcal capsular polysaccharides conjugated to protein D for prevention of acute otitis media caused by both *Streptococcus pneumoniae* and non-typable Haemophilus influenzae: a randomized double-blind efficacy study," Lancet, vol. 367, No. 9512, Mar. 4, 2006, pp. 740-748.
Reffuveille et al., "A Broad-Spectrum Antibiofilm Peptide Enhances Antibiotic Action against Bacterial Biofilms", Antimicrobial Agents and Chemotherapy, vol. 58, No. 9, Sep. 2014, pp. 5363-5371.
Rice et al., "Crystal Structure of an IHF-DNA Complex: A Protein-Induced DNA U-Turn," Cell, vol. 87, No. 7, pp. 1295-1306 (Dec. 27, 1996).
Rouviere-Yaniv J, Gros F. Characterization of a novel, low-molecular-weight DNA-binding protein from *Escherichia coli*. Proceedings of the National Academy of Sciences of the United States of America. 1975;72(9):3428-32. Epub Sep. 1, 1975. PubMed PMID: 1103148; PMCID: 433007.
Sapi et al., "Characterization of Biofilm Formation by Borrelia burgdorferi In Vitro," PLOS One, vol. 7, No. 10, Oct. 2012, pp. 1-11.
Schwartz, K. et al. (2012) "Functional Amyloids Composed of Phenol Soluble Modulins Stabilize *Staphylococcus aureus* Biofilms," PLOS Pathogens 8:e1002744, 1-11.
Segall et al., "Architectural elements in nucleoprotein complexes: interchangeability of specific and non-specific DNA binding proteins," The EMBO Journal, vol. 13, No. 19, 1994, pp. 4536-4548.
Shahrooei et al., "Inhibition of *Staphylococcus epidermidis* Biofilm Formation by Rabbit Polyclonal Antibodies against the SesC Protein," Infection and Immunity, vol. 77, No. 9, Sep. 2009, pp. 3670-3678.
Shields, R.C. et al. (2013) "Efficacy of a Marine Bacterial Nuclease against Biofilm Forming Microorganisms Isolated from Chronic Rhinosinusitis," PLoS ONE 8(2):e55339, 1-13.
Singh et al., "Quorum-sensing signals indicate that cystic fibrosis lungs are infected with bacterial biofilms," Nature, vol. 407, No. 12, Oct. 12, 2000, pp. 762-764.
Slots J, Gibbons RJ. Attachment of *Bacteroides melaninogenicus* subsp. asaccharolyticus to oral surfaces and its possible role in colonization of the mouth and of periodontal pockets. Infection and immunity.1978;19(1):254-64. Epub Jan. 1, 1978. PubMed PMID: 24002; PMCID: 414075.
Smith et al., "Cystic Fibrosis Airway Epithelia Fail to Kill Bacteria Because of Abnormal Airway Surface Fluid," Cell, vol. 85, Apr. 19, 1996, pp. 229-236.

Stinson, M.W. et al. (1998) "Streptococcal Histone-Like Protein: Primary Structure of hlpA and Protein Binding to Lipoteichoic Acid and Epithelial Cells," Infection and Immunity 66(1):259-265.
Stoltz et al., "Cystic Fibrosis Pigs Develop Lung Disease and Exhibit Defective Bacterial Eradication at Birth," www. ScienceTranslationMedicine.org, vol. 2, No. 29, Apr. 28, 2010, pp. 1-8.
Sun et al.,"Inhibition of Biofilm Formation by Monoclonal Antibodies against *Staphylococcus epidermindis* RP62A Accumulation-Associated Protein," Clinical & Diagnostic Laboratory Immunology, vol. 12, No. 1, Jan. 2005, pp. 93-100.
Swinger et al., "IHF and HU: flexible architects of bent DNA," Current Opinion in Structural Biology, vol. 14, No. 1, 2004, pp. 28-35.
Teter et al., "DNA Bending and Twisting Properties of Integration Host Factor Determined by DNA Cyclization," Plasmid, vol. 43, 2000, pp. 73-84.
Tjokro NO, Rocco CJ, Priyadarshini R, Davey ME, Goodman SD. A biochemical analysis of the interaction of Porphyromonas gingivalis HU PG0121 protein with DNA. PloS one. 2014;9(3):e93266. Epub Apr. 1, 2014. doi: 10.1371.
Tsaras et al., "Incidence, Secular Trends, and Outcomes of Prosthetic Joint Infection: A Population-Based Study, Olmsted County, Minnesota, 1969-2007," Infect Control Hosp Epidemiol., vol. 33, No. 12, Dec. 2012, pp. 1207-1212.
UniProtKB/TrEMBL A0A0E4BIL9. Putative DNA-binding protein HU (Sep. 16, 2015) [Retrieved from the Internet Jan. 12, 2017: ],1 page.
van de Rijn I, Kessler RE. Growth characteristics of group A streptococci in a new chemically defined medium. Infection and immunity. l980;27(2):444-8. Epub Feb. 1, 1980. PubMed PMID: 6991416; PMCID: 550785.
Van Schaik et al., "DNA Binding: a Novel Function of Pseudomonas aeruginosa Type IV Pili," Journal of Bacteriology, vol. 187, No. 4, Feb. 2005, pp. 1455-1464.
Whitchurch et al., "Extracellular DNA Required for Bacterial Biofilm Formation," Science, vol. 295, No. 5559, Feb. 22, 2002, p. 1487, 1 page.
Whitchurch et al., "Extracellular DNA Required for Bacterial Biofilm Formation," Science, vol. 295, No. 5559, Feb. 22, 2002, Supplementary Material, 2 pages.
Winters et al., "Isolation and Characterization of a *Streptococcus pyogenes* Protein that Binds to Basal Laminae of Human Cardiac Muscle," Infection and Immunity, vol. 61, No. 8, Aug. 1993, pp. 3259-3264.
Woischnig et al., "High Affinity Native Human Monoclonal Antibody with Broad Cross-Species Biofilm Disrupting Activity" poster presented at ICAAC Meeting on Sep. 20, 2015, available at www. trellisbio.com/assets/docs/ICAAC%20Biofilm%20Poster%2020150920. pdf., 1 page.
Zimmerli et al., "Pathogenesis of Foreign Body Infection: Description and Characteristics of an Animal Model," The Journal of Infectious Diseases, vol. 146, No. 4, Oct. 1982, pp. 487-497.
International Search Report dated Apr. 5, 2017 in International Application No. PCT/US2016/57237.
Kadajji et al., "Water Soluble Polymers for Pharmaceutical Applications", Polymers (2011), 3(4):1972-2009; Abstract; p. 1985, last para; p. 1988, 2nd Para.
Thurnheer et al., Colonisation of gingival epithelia by subgingival biofilms in vitro: role of "red complex" bacteria. Arch Oral Biol. (2014), 59(9):977-86; Abstract; p. 2, 1st para; p. 10, 1st para.
UniProtKB/TrEMBL A0A0E4BIL9. Putative DNA-binding protein HU (Sep. 16, 2015) [Retrieved from the Internet Jan. 12, 2017: <http://www.uniprot.org/uniprot/A0A0E4BIL9.txt?version=3>].
Woischnig et al., "High Affinity Native Human Monoclonal Antibody with Broad Cross-Species Biofilm Disrupting Activity", (Sep. 20, 2015) [Retrieved from the Internet Dec. 25, 2016: <http://www. trellisbio.com/assets/docs/ICAAC%20Biofilm%/20Poster% 2020150920.pdf>].
Wu, et al., "Preparation of sodium fluoride-loaded gelatin microspheres, characterization and cariostatic studies", J Microencapsul. (2004), 21(8):889-903; Abstract.

(56) References Cited

OTHER PUBLICATIONS

U.S. Appl. No. 16/820,463, filed Mar. 16, 2020, The Research Institute at Nationwide Children's Hospital; Ohio State Innovation Foundation.
U.S. Appl. No. 17/150,731, filed Jan. 15, 2021, The Research Institute at Nationwide Children's Hospital.
Allaker et al., "Non-conventional therapeutics for oral infections," Virulence, vol. 6, No. 3, Apr. 2015, pp. 196-207.
Beer et al., "Poly (lactic-glycolic) acid copolymer encapsulation of recombinant adenovirus reduces immunogenicity in vivo," Gene Therapy, vol. 5, Jan. 5, 1998, pp. 740-746.
Ben et al., "Low level of galacto-oligosaccharide in infant formula stimulates growth of intestinal Bifidobacteria and Lactobacilli," World Journal of Gastroenterology, vol. 14, No. 42, Nov. 14, 2008, pp. 6564-6568.
Chavarri et al., "Microencapsulation of a probiotic and prebiotic in alginate-chitosan capsules improves survival in simulated gastrointestinal conditions," International Journal of Food Microbiology, vol. 142, Jun. 22, 2010, pp. 185-189.
Chen et al., "The effect of immobilization of probiotic Lactobacillus reuteri DPC16 in sub-100 μm microcapsule on food-borne pathogens", World J. Microbial. Biotechnol., vol. 28, No. 6, Mar. 30, 2012, pp. 2447-2452.
Cook et al., "Microencapsulation of a synbiotic into PLGA/alginate multiparticulate gels," International Journal of Pharmaceutics, vol. 466, Mar. 20, 2014, pp. 400-408.
Cook et al., "Microencapsulation of probiotics for gastrointestinal delivery," Journal of Controlled Release, vol. 162, Jun. 11, 2012, pp. 56-67.
Cornaz Gudet et al., "Simple method of in vitro diffusion of nicotine across procine palatine mucosa", European Journal of Pharmaceutics and Biopharmaceutics, vol. 43, No. 3, Jan. 16, 1997, pp. 259-264.
Crittenden et al., "Synbiotic Microcapsules That Enhance Microbial Viability during Nonrefrigerated Storage and Gastrointestinal Transit", Applied and Environmental Microbiology, vol. 72, No. 3, Mar. 2006, 2280-2282.
Estrela et al., "Combining Biofilm-Controlling Compounds and Antibiotics as a Promising New Way to Control Biofilm Infections", Pharmaceuticals, vol. 3, No. 5, May 11, 2010, pp. 1374-1393.
Goodman et al., "Biofilms can be dispersed by focusing the immune system on a common family of bacterial nucleoid-associated proteins", Advances in Mucosal Immunology, Jun. 29, 2011, pp. 1-13.
Kadajji et al., "Water Soluble Polymers for Pharmaceutical Applications," Polymers, vol. 3, Nov. 11, 2011, pp. 1972-2009.
Kumari et al., "Biodegradable polymeric nanoparticles based drug delivery systems," Colloids and Surfaces B: Biointerfaces, vol. 75, Sep. 8, 2009, pp. 1-18.
Nowakowska, J. et al. (2014) "Foreign Body Infection Models to Study Host-Pathogen Response and Antimicrobial Tolerance of Bacterial Biofilm," Antibiotics 3:378-397, Aug. 2014.
Ornelas-Megiatto et al., "Aerosolized Antimicrobial Agents Based on Degradable Dextran Nanoparticles Loaded with Silver Carbene Complexes", Molecular Pharmaceutics, vol. 9, No. 11, Oct. 1, 2012, pp. 3012-3022.
Petreska Ivanovska et al., "Comparative evaluation of viability of encapsulated Lactobacillus casei using two different methods of microencapsulation," International Journal of Pharmaceutical and Phytopharmacological Research, vol. 4, No. 1, pp. 20-24 (Abstract only). Dec. 2014.
Pliszczak et al., "Improvement of an encapsulation process for the preparation of pro- and prebiotics-loaded bioadhesive microparticles by using experimental design," European Journal of Pharmaceutical Sciences, vol. 44, Jun. 25, 2011, pp. 83-92.
Rezaee et al., "Prebiotics Decrease the Antibacterial Effect of Nano Silver nd Nano TIO2 Particles Against Probiotic Bacteria of Food", Current Nutrition and Food Science, vol. 10, No. 2, Jul. 15, 2013, pp. 88-93.
Sathyabama et al., "Co-encapsulation of probiotics with prebiotics on alginate matrix and its effect on viability in simulated gastric environment," LWT—Food Science and Technology, vol. 57, Dec. 16, 2013, pp. 419-425.
Sultana et al., "Encapsulation of probiotic bacteria with alginate-starch and evaluation of survival in simulated gastrointestinal conditions and in yoghurt," International Journal of Food Microbiology, vol. 62, May 26, 2000, pp. 47-55.
Thurnheer et al., "Colonisation of gingival epithelia by subgingival biofilms in vitro: role of 'red complex' bacteria," Archives in Oral Biology, vol. 59, No. 9, Sep. 2014, pp. 1-24.
UniProtKB: TrEMBL A0A0E4BIL9. Putative DNA-binding protein HU, 2015, retrieved from www.uniprot.org/uniprot/A0A0E4BIL9.txt?version=3, 1 page.
Varshosaz, "The promise of chitosan microspheres in drug delivery systems", Expert Opinion on Drug Delivery, vol. 4, No. 3, May 9, 2007, pp. 263-273.
Wu et al., "Preparation of sodium fluoride-loaded gelatin microspheres, characterization and cariostatic studies," J Microencapsul., vol. 21, No. 8, Dec. 2004, pp. 889-903, Abstract Only.
Bendig, Mary M., "Humanization of Rodent Monoclonal Antibodies by CDR Grafting", Methods: A Companion to Methods in Enzymology, 1995, vol. 8, pp. 83-93.
Chen, et al., "Enhancement and destruction of antibody function by somatic mutation: unequal occurrence is controlled by V gene combinatorial associations", The EMBO Journal, 1995, vol. 14, No. 12, pp. 2784-2794.
Kussie, et al., "A Single Engineered Amino Acid Substitution Changes Antibody Fine Specificity", Journal of Immunology, 1994, vol. 152, pp. 146-152.

* cited by examiner

FIG. 3 (CONTD.)

SEQUENCE LISTING

<160> NUMBER OF SEQ ID NOS: 27

<210> SEQ ID NO 1
<211> LENGTH: 85
<212> TYPE: PRT
<213> ORGANISM: Tannerella forsythia

<400> SEQUENCE: 1

Met Asn Lys Thr Glu Phe Ile Asn Ala Val Ala Glu Lys Ala Gly Leu
1               5                   10                  15

Ser Lys Val Asp Gly Lys Lys Ala Val Glu Ala Met Val Lys Thr Ile
            20                  25                  30

Gln Gly Glu Met Lys Lys Gly Glu Lys Val Ser Ile Leu Gly Phe Gly
        35                  40                  45

Ser Phe Ser Val Val Glu Lys Ala Ser Arg Lys Gly Val Asn Pro Gln
    50                  55                  60

Thr Lys Lys Val Ile Asn Ile Pro Ala Arg Lys Val Ile Lys Phe Lys
65                  70                  75                  80

Pro Gly Thr Asp Leu
                85

<210> SEQ ID NO 2
<211> LENGTH: 88
<212> TYPE: PRT
<213> ORGANISM: Porphyromonas endodontalis

<400> SEQUENCE: 2

Met Asn Lys Thr Glu Phe Ile Ala Ala Val Ala Glu Lys Ala Gly Leu
1               5                   10                  15

Thr Lys Ala Asp Ala Gln Arg Ala Val Asn Ala Phe Thr Glu Val Val
            20                  25                  30

Lys Glu Thr Met Glu Lys Gly Asp Arg Leu Pro Leu Val Gly Phe Gly
        35                  40                  45

Thr Phe Ser Val Ser Gln Arg Lys Ala Arg Glu Gly Lys Asn Pro Arg
    50                  55                  60

Thr Gly Glu Thr Ile Lys Ile Ala Ala Arg Lys Val Val His Phe Lys
65                  70                  75                  80

Pro Gly Ala Asn Leu Asp Leu Lys
                85

<210> SEQ ID NO 3
<211> LENGTH: 87
<212> TYPE: PRT
<213> ORGANISM: Porphyromonas macacae

<400> SEQUENCE: 3

Met Asn Lys Ser Glu Phe Ile Ala Glu Val Ala Lys Ala Gly Met
1               5                   10                  15

Thr Lys Val Asp Ala Gln Lys Ser Val Asn Ala Phe Ile Glu Val Ile
            20                  25                  30

Gln Glu Gln Met Lys Lys Gly Glu Lys Val Ala Leu Leu Gly Phe Gly
        35                  40                  45

Thr Phe Ser Val Thr Gln Lys Ala Ala Arg Thr Gly Ile Asn Pro Lys
    50                  55                  60

Thr Lys Lys Ala Ile Lys Ile Pro Ala Arg Lys Ala Val Lys Phe Lys
65                  70                  75                  80

Ala Gly Ser Ala Leu Asp Val
                85

```
<210> SEQ ID NO 4
<211> LENGTH: 83
<212> TYPE: PRT
<213> ORGANISM: Bergeyella zoohelcum

<400> SEQUENCE: 4

Met Asn Lys Thr Asp Phe Ile Ala Ala Val Ala Glu Lys Ala Asn Leu
1               5                   10                  15

Thr Lys Ala Asp Ala Gln Arg Ala Val Asn Ala Phe Ala Glu Val Val
            20                  25                  30

Thr Glu Gln Met Asn Ala Gly Glu Lys Ile Ala Leu Ile Gly Phe Gly
        35                  40                  45

Thr Phe Ser Val Ser Glu Arg Ala Ala Arg Lys Gly Ile Asn Pro Ala
    50                  55                  60

Thr Lys Gln Pro Ile Asn Ile Pro Ala Lys Met Val Ala Lys Phe Lys
65                  70                  75                  80

Pro Gly Thr

<210> SEQ ID NO 5
<211> LENGTH: 85
<212> TYPE: PRT
<213> ORGANISM: Parabacteroides johnsonii

<400> SEQUENCE: 5

Met Asn Lys Thr Glu Phe Ile Asn Ala Val Ala Glu Lys Ser Gly Leu
1               5                   10                  15

Ser Lys Val Asp Ala Lys Lys Ala Glu Ala Phe Val Glu Thr Val
            20                  25                  30

Ser Ser Glu Leu Lys Glu Gly Gly Lys Val Ala Leu Leu Gly Phe Gly
        35                  40                  45

Ser Phe Ser Val Ala Glu Lys Ala Ala Arg Lys Gly Val Asn Pro Lys
    50                  55                  60

Thr Lys Gln Pro Ile Glu Ile Pro Ala Arg Lys Ser Val Lys Phe Lys
65                  70                  75                  80

Ala Gly Ala Glu Leu
                85

<210> SEQ ID NO 6
<211> LENGTH: 87
<212> TYPE: PRT
<213> ORGANISM: Porphyromonas cangingivalis

<400> SEQUENCE: 6

Met Asn Lys Thr Glu Phe Ile Ser Ala Val Ala Glu Lys Ala Gly Ala
1               5                   10                  15

Thr Lys Val Asp Thr Lys Ala Ile Val Asp Ala Ala Val Ala Val Ile
            20                  25                  30

Ala Glu Glu Met Lys Lys Gly Glu Lys Val Ala Ile Leu Gly Phe Gly
        35                  40                  45

Thr Phe Ser Val Val Glu Arg Ala Lys Arg Glu Gly Phe Asn Pro Arg
    50                  55                  60

Thr Lys Glu Lys Ile Lys Ile Pro Ala Arg Lys Ile Val Lys Phe Lys
65                  70                  75                  80

Pro Gly Ser Asp Leu Asp Ile
                85
```

```
<210> SEQ ID NO 7
<211> LENGTH: 85
<212> TYPE: PRT
<213> ORGANISM: Bacteroides faecichinchillae

<400> SEQUENCE: 7

Met Asn Lys Ser Glu Leu Ile Ser Ala Met Ala Thr Glu Ala Gln Met
1               5                   10                  15

Ser Lys Ala Asp Ala Lys Arg Ala Leu Glu Ala Phe Ile Thr Ser Val
            20                  25                  30

Thr Asn Ala Met Lys Ala Gly Asp Lys Val Ser Leu Val Gly Phe Gly
        35                  40                  45

Thr Phe Ala Val Ser Glu Arg Ala Ala Arg Thr Gly Ile Asn Pro Ser
    50                  55                  60

Thr Lys Ala Ser Ile Thr Ile Pro Ala Lys Lys Val Ala Lys Phe Lys
65                  70                  75                  80

Pro Gly Ala Glu Leu
                85

<210> SEQ ID NO 8
<211> LENGTH: 85
<212> TYPE: PRT
<213> ORGANISM: Odoribacter splanchnicus

<400> SEQUENCE: 8

Met Asn Lys Ala Gln Leu Ile Asp Ala Ile Ala Glu Lys Ala Gly Leu
1               5                   10                  15

Thr Lys Ala Asp Ser Lys Lys Ala Leu Glu Ala Phe Val Glu Thr Val
            20                  25                  30

Gly Glu Ala Leu Lys Gly Gly Asp Lys Val Ala Leu Ile Gly Phe Gly
        35                  40                  45

Ser Phe Ser Val Ser Glu Arg Ser Ala Arg Ser Gly Arg Asn Pro Gln
    50                  55                  60

Thr Gly Lys Thr Ile Thr Ile Pro Ala Lys Lys Val Val Lys Phe Lys
65                  70                  75                  80

Ala Gly Ala Glu Leu
                85

<210> SEQ ID NO 9
<211> LENGTH: 85
<212> TYPE: PRT
<213> ORGANISM: Bacteroides pyogenes

<400> SEQUENCE: 9

Met Asn Lys Ser Glu Leu Val Ser Ala Met Ala Ala Glu Ala Gln Met
1               5                   10                  15

Ser Lys Ala Asp Ala Lys Lys Ala Leu Asp Ala Phe Ile Ser Ser Val
            20                  25                  30

Thr Lys Ala Met Lys Ala Gly Asp Lys Val Ser Leu Val Gly Phe Gly
        35                  40                  45

Thr Phe Ser Val Ser Glu Arg Ser Ala Arg Thr Gly Ile Asn Pro Ser
    50                  55                  60

Thr Lys Ala Thr Ile Thr Ile Pro Ala Lys Lys Val Ala Lys Phe Lys
65                  70                  75                  80

Ala Gly Ala Glu Leu
                85

<210> SEQ ID NO 10
```

```
<211> LENGTH: 82
<212> TYPE: PRT
<213> ORGANISM: Saprospira grandis

<400> SEQUENCE: 10
```

| Met<br>1 | Asn | Lys | Gly | Asp<br>5 | Leu | Ile | Asp | Lys | Ile<br>10 | Ala | Glu | Ala | Ala | Gly<br>15 | Leu |
|---|---|---|---|---|---|---|---|---|---|---|---|---|---|---|---|
| Lys | Lys | Ala | Asp<br>20 | Ala | Ala | Ala | Leu | Asn<br>25 | Ala | Thr | Leu | Glu | Thr<br>30 | Ile | |
| Ala | Asp | Thr<br>35 | Leu | Lys | Ala | Gly | Gln<br>40 | Lys | Ile | Thr | Leu | Val<br>45 | Gly | Phe | Gly |
| Thr | Phe<br>50 | Asp | Val | Asn | Tyr | Arg<br>55 | Ala | Ala | Arg | Lys | Gly<br>60 | Ile | Asn | Pro | Ser |
| Thr<br>65 | Gln | Lys | Glu | Ile | Gln<br>70 | Ile | Ser | Asp | Lys | Val<br>75 | Thr | Val | Lys | Phe | Lys<br>80 |
| Ala | Gly | | | | | | | | | | | | | | |

```
<210> SEQ ID NO 11
<211> LENGTH: 88
<212> TYPE: PRT
<213> ORGANISM: Porphyromonas gingivalis

<400> SEQUENCE: 11
```

| Met<br>1 | Asn | Lys | Thr | Asp<br>5 | Phe | Ile | Ala | Ala | Val<br>10 | Ala | Glu | Lys | Ala | Asn<br>15 | Leu |
|---|---|---|---|---|---|---|---|---|---|---|---|---|---|---|---|
| Thr | Lys | Ala | Asp<br>20 | Ala | Gln | Arg | Ala | Val<br>25 | Asn | Ala | Phe | Ala | Glu<br>30 | Val | Val |
| Thr | Glu | Gln<br>35 | Met | Asn | Ala | Gly | Glu<br>40 | Lys | Ile | Ala | Leu | Ile<br>45 | Gly | Phe | Gly |
| Thr | Phe<br>50 | Ser | Val | Ser | Glu | Arg<br>55 | Ala | Ala | Arg | Lys | Gly<br>60 | Ile | Asn | Pro | Lys |
| Thr<br>65 | Lys | Lys | Ser | Ile | Ser<br>70 | Ile | Pro | Ala | Arg | Lys<br>75 | Val | Val | Arg | Phe | Lys<br>80 |
| Pro | Gly | Ser | Thr | Leu<br>85 | Glu | Leu | Lys | | | | | | | | |

```
<210> SEQ ID NO 12
<211> LENGTH: 91
<212> TYPE: PRT
<213> ORGANISM: Streptococcus gordonii

<400> SEQUENCE: 12
```

| Met<br>1 | Ala | Asn | Lys | Gln<br>5 | Asp | Leu | Ile | Ala | Lys<br>10 | Val | Ala | Ala | Ala | Thr<br>15 | Glu |
|---|---|---|---|---|---|---|---|---|---|---|---|---|---|---|---|
| Leu | Thr | Lys | Lys<br>20 | Asp | Ser | Ala | Ala | Ala<br>25 | Val | Asp | Ala | Val | Phe<br>30 | Ala | Ala |
| Val | Thr | Glu<br>35 | Tyr | Leu | Ser | Lys | Gly<br>40 | Glu | Lys | Val | Gln | Leu<br>45 | Ile | Gly | Phe |
| Gly | Asn<br>50 | Phe | Glu | Val | Arg | Glu<br>55 | Arg | Ala | Ala | Arg | Lys<br>60 | Gly | Arg | Asn | Pro |
| Gln<br>65 | Thr | Gly | Lys | Glu | Ile<br>70 | Lys | Ile | Ala | Ala | Ser<br>75 | Lys | Val | Pro | Ala | Phe<br>80 |
| Lys | Ala | Gly | Lys | Ala<br>85 | Leu | Lys | Asp | Val | Ile<br>90 | Lys | | | | | |

```
<210> SEQ ID NO 13
<211> LENGTH: 24
<212> TYPE: PRT
```

<213> ORGANISM: Porphyromonas gingivalis

<400> SEQUENCE: 13

Ala Ala Arg Lys Gly Ile Asn Pro Lys Thr Lys Lys Ser Ile Ser Ile
1               5                   10                  15

Pro Ala Arg Lys Val Val Arg Phe
            20

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Pro Ser Leu Lys Leu
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Pro Ser Leu
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ser Leu Lys
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Pro Ser Leu Lys
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Leu Lys Leu
1

<210> SEQ ID NO 19
<211> LENGTH: 384
<212> TYPE: PRT
<213> ORGANISM: Homo sapiens

<400> SEQUENCE: 19

```
Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Ser Pro Gln Pro Ala Thr
            340                 345                 350

Tyr Thr Cys Val Val Ser His Glu Asp Ser Arg Thr Leu Leu Asn Ala
        355                 360                 365

Ser Arg Ser Leu Glu Val Ser Tyr Val Thr Asp His Gly Pro Met Lys
```

```
                    370                 375                 380

<210> SEQ ID NO 20
<211> LENGTH: 330
<212> TYPE: PRT
<213> ORGANISM: Homo sapiens

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 21
<211> LENGTH: 326
<212> TYPE: PRT
<213> ORGANISM: Homo sapiens
```

<400> SEQUENCE: 21

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 22
<211> LENGTH: 377
<212> TYPE: PRT
<213> ORGANISM: Homo sapiens

<400> SEQUENCE: 22

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 23
<211> LENGTH: 452
<212> TYPE: PRT
<213> ORGANISM: Homo sapiens

<400> SEQUENCE: 23

Gly Ser Ala Ser Ala Pro Thr Leu Phe Pro Leu Val Ser Cys Glu Asn
 1               5                  10                  15

Ser Pro Ser Asp Thr Ser Ser Val Ala Val Gly Cys Leu Ala Gln Asp
            20                  25                  30
```

```
Phe Leu Pro Asp Ser Ile Thr Leu Ser Trp Lys Tyr Lys Asn Asn Ser
         35                  40                  45

Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Gly Asn Pro Arg
                115                 120                 125

Lys Ser Lys Leu Ile Cys Gln Ala Thr Gly Phe Ser Pro Arg Gln Ile
        130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
                180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
        210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
                260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
        290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
                355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
                420                 425                 430

Gly Lys Pro Thr Leu Tyr Asn Val Ser Leu Val Met Ser Asp Thr Ala
                435                 440                 445
```

```
Gly Thr Cys Tyr
    450

<210> SEQ ID NO 24
<211> LENGTH: 327
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 25
<211> LENGTH: 353
<212> TYPE: PRT
<213> ORGANISM: Homo sapiens
```

<400> SEQUENCE: 25

```
Ala Ser Pro Thr Ser Pro Lys Val Phe Pro Leu Ser Leu Cys Ser Thr
1               5                   10                  15
Gln Pro Asp Gly Asn Val Val Ile Ala Cys Leu Val Gln Gly Phe Phe
            20                  25                  30
Pro Gln Glu Pro Leu Ser Val Thr Trp Ser Glu Ser Gly Gln Gly Val
        35                  40                  45
Thr Ala Arg Asn Phe Pro Pro Ser Gln Asp Ala Ser Gly Asp Leu Tyr
    50                  55                  60
Thr Thr Ser Ser Gln Leu Thr Leu Pro Ala Thr Gln Cys Leu Ala Gly
65                  70                  75                  80
Lys Ser Val Thr Cys His Val Lys His Tyr Thr Asn Pro Ser Gln Asp
                85                  90                  95
Val Thr Val Pro Cys Pro Val Pro Ser Thr Pro Pro Thr Pro Ser Pro
            100                 105                 110
Ser Thr Pro Pro Thr Pro Ser Pro Ser Cys Cys His Pro Arg Leu Ser
        115                 120                 125
Leu His Arg Pro Ala Leu Glu Asp Leu Leu Leu Gly Ser Glu Ala Asn
    130                 135                 140
Leu Thr Cys Thr Leu Thr Gly Leu Arg Asp Ala Ser Gly Val Thr Phe
145                 150                 155                 160
Thr Trp Thr Pro Ser Ser Gly Lys Ser Ala Val Gln Gly Pro Pro Glu
                165                 170                 175
Arg Asp Leu Cys Gly Cys Tyr Ser Val Ser Ser Val Leu Pro Gly Cys
            180                 185                 190
Ala Glu Pro Trp Asn His Gly Lys Thr Phe Thr Cys Thr Ala Ala Tyr
        195                 200                 205
Pro Glu Ser Lys Thr Pro Leu Thr Ala Thr Leu Ser Lys Ser Gly Asn
    210                 215                 220
Thr Phe Arg Pro Glu Val His Leu Leu Pro Pro Pro Ser Glu Glu Leu
225                 230                 235                 240
Ala Leu Asn Glu Leu Val Thr Leu Thr Cys Leu Ala Arg Gly Phe Ser
                245                 250                 255
Pro Lys Asp Val Leu Val Arg Trp Leu Gln Gly Ser Gln Glu Leu Pro
            260                 265                 270
Arg Glu Lys Tyr Leu Thr Trp Ala Ser Arg Gln Glu Pro Ser Gln Gly
        275                 280                 285
Thr Thr Thr Phe Ala Val Thr Ser Ile Leu Arg Val Ala Ala Glu Asp
    290                 295                 300
Trp Lys Lys Gly Asp Thr Phe Ser Cys Met Val Gly His Glu Ala Leu
305                 310                 315                 320
Pro Leu Ala Phe Thr Gln Lys Thr Ile Asp Arg Leu Ala Gly Lys Pro
                325                 330                 335
Thr His Val Asn Val Ser Val Val Met Ala Glu Val Asp Gly Thr Cys
            340                 345                 350
Tyr
```

<210> SEQ ID NO 26
<211> LENGTH: 340
<212> TYPE: PRT
<213> ORGANISM: Homo sapiens

<400> SEQUENCE: 26

```
Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
                100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
    275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 27
<211> LENGTH: 106
<212> TYPE: PRT
<213> ORGANISM: Homo sapiens

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30
```

```
Pro Arg Glu Ala Lys Val Gln Trp Lys Val Asp Asn Ala Leu Gln Ser
        35              40              45

Gly Asn Ser Gln Glu Ser Val Thr Glu Gln Asp Ser Lys Asp Ser Thr
 50              55              60

Tyr Ser Leu Ser Ser Thr Leu Thr Leu Ser Lys Ala Asp Tyr Glu Lys
 65              70              75              80

His Lys Val Tyr Ala Cys Glu Val Thr His Gln Gly Leu Ser Ser Pro
            85              90              95

Val Thr Lys Ser Phe Asn Arg Gly Glu Cys
            100             105
```

HU SPECIFIC INTERFERING AGENTS

CROSS-REFERENCE TO RELATED APPLICATIONS

This application is a continuation under 35 U.S.C. §§ 120 of International Application No. PCT/US2016/057237, filed Oct. 14, 2016, which in turn claims priority under 35 U.S.C. 119(e) to U.S. Ser. No. 62/241,670, filed Oct. 14, 2015; U.S. Ser. No. 62/242,235, filed Oct. 15, 2015; and U.S. Ser. No. 62/347,551 filed Jun. 8, 2016, the contents of each of which is incorporated herein by reference.

STATEMENT OF GOVERNMENT SUPPORT

This invention was made with government support under DC011818 and DE019117 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Nov. 9, 2016, is named 106887-0510_SL.txt and is 37,382 bytes in size.

FIELD

The present disclosure generally relates to methods and compositions to lessen and/or cure bacterial biofilms and/or inhibit or prevent bacterial infection.

BACKGROUND

At least one protein from the DNABII family of proteins is found in all known eubacteria and are naturally found outside of the bacterial cell; the HU protein specifically is found within a number of microbes implicated in biofilm formation. While they elicit a strong innate immune response, host subjects fail to naturally produce specific neutralizing antibody to DNABII protein family members as a result of infection.

Chronic and recurrent infections can result when the human body fails to clear disease causing bacteria. Such bacteria may have ways of persisting. One means by which bacteria persist is by invading human host cells. Once inside they are protected from the immune system and antimicrobial therapies. Moreover, these bacteria have evolved to divide and eventually kill these host cells, releasing the endogenous bacteria and allowing subsequent re-infection; this is the root cause of the chronicity of the disease state. Another mechanism is the formation of a biofilm. The major problem with bacterial biofilms is the inability of the host immune system and/or antibiotics and other antimicrobials to gain access to the bacteria protected within the biofilm. The DNABII DNA-binding proteins are an important component of the extracellular matrix of bacterial biofilms, binding to and maintaining the structure of the extracellular DNA component of such biofilms.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility to the point where fouling and corrosive biofilm organisms have even been found on the surfaces of final product storage tanks.

In the home, biofilms are found in or on any surface that supports microbial growth, e.g., in drains, on food preparation surfaces, in toilets, and in swimming pools and spas. Biofilms are implicated in a wide range of water processes, both domestic and industrial. They can grow on the surface of process equipment and impede the performance of the equipment, such as degradation of heat transfer or plugging of filters and membranes. Biofilms growing on a cooling tower fill can add enough weight to cause collapse of the fill. Biofilms cause corrosion of even highly specialized stainless steels. Biofilms in a water process can degrade the value of a final product such as biofilm contamination in a paper process or the attachment of even a single cell on a silicon chip. Biofilms growing in drinking water distribution systems can harbor potential pathogenic organisms, corrosive organisms or bacteria that degrade the aesthetic quality of the water.

SUMMARY

Within bacterial cells, the DNABII proteins are DNA binding proteins that necessarily bend DNA substrates upon binding. Similarly, DNA that is already in a bent conformation is an exemplary substrate as the energy required for bending is rendered unnecessary.

The DNABII family of proteins is also found outside of bacterial cells in the biofilm state. One of DNABII protein is the histone-like ("HU") protein found in many bacteria involved in biofilm formation. Not to be bound by theory, targeting these proteins for removal from the extracellular matrix may result in the collapse of the biofilm structure and the release of resident bacteria.

Aspects of this disclosure relate to the understanding that the HU polypeptides of microbial pathogens may be antigenically diverse and are highly important to biofilm formation and/or growth. Thus, this disclosure provides compositions and methods relating to the protein-specific removal of biofilms, focusing on interfering agents that specifically inhibit, compete, or titrate binding of an HU polypeptide to a microbial DNA. This disclosure further provides compositions and method relating to the use of such interfering agents to inhibit or prevent bacterial infection, e.g. a bacteria infecting a cell or tissue, by a bacteria that exports an HU protein.

In some aspects, this HU polypeptide is the HU polypeptide of a biofilm-forming or an infectious microbial pathogen. Not bound by theory, aspects of the disclosure contemplate the use of highly specific interfering agents to target specific biofilm-forming or an infectious microbial pathogen based on the underlying antigenic diversity of each microbial pathogen HU polypeptide (that may be optionally shared across class, order, family, genus, or species thereof).

In one aspect, the interfering agents target and disrupt biofilms or bacterial infection where an HU polypeptide from *P. gingivalis* ("annotated as "Pg" below) is present. Without being bound by theory, Applicants submit that only the HU beta subunit appears important extracellularly. *S. gordonii* (annotated as "Sg" below) has just one HU allele (common amino acids are shown between the two sequences and +means similar amino acid) and the significance amino acid substitutions can be found between amino acids from about 56 to 80, or alternatively from 60 to 75, or alternatively from about amino acid 61 to 74 as noted below:

```
Pg   1    MNKTDFIAAVAEKANLTKADAQRAVNAFAEVVTEQMNAGEKIALIGFGTFSVSERAARKGI
61
          NK D IA VA     LTK D+   AV+A     VTE ++ GEK+ LIGFG F V ERAARKG
Sg   1    MANKQDLIAKVAAATELTKKDSAAAVDAVFAAVTEYLSKGEKVQLIGFGNFEVRERAARKGR
62

Pg   62   NPKTKKSISIPARKVVRFKPGSTLELK              88 (SEQ ID NO: 11)
          NP+T K I I A KV  FK G  L+
Sg   63   NPQTGKEIKIAASKVPAFKAGKALKDVIK            91 (SEQ ID NO: 12)
```

Not to be limited by theory, Applicant submits that the amino acid at positions 61 and/or 64—e.g. the presence of I (or alternatively another hydrophobic amino acid, that includes, but is not limited to V or F) at position 61 and/or K at position 64—have an impact on the antibody binding target for HU; thus rendering it antigenically distinct. As used herein and throughout this application, these position numbers are used in reference to the sequence of P. gingivalis provided above. It is understood that corresponding positions in other sequences, having different amino acid numbering due to differing length, can be readily determined through sequence alignment as depicted in the preceding paragraph. It is further submitted that other amino acid differences between sequences, such as those disclosed herein above can contribute to the distinctiveness of certain HU of particular species. Thus, in one aspect, Applicant provides a method to modify wild-type polypeptides by the substitution of I (or alternatively another hydrophobic amino acid such as V or F) and/or K for the native amino acids at corresponding positions in HU polypeptides from other bacterial species, and the mutated, non-naturally occurring polypeptides so produced. In a further aspect, this disclosure provides antibodies, polyclonal and monoclonal and modified antibodies as disclosed herein) that specifically recognize and bind the mutated polypeptides, and their use as correlated for the bacterial species as noted herein for P. gingivalis.

Certain aspects of the disclosure relate to an interfering agent capable of specifically competing, titrating, or inhibiting the binding of an HU protein to a microbial DNA and methods of use thereof related to biofilms. In some aspects, the interfering agent competes, titrates, or inhibits the binding of an HU protein but does not compete, titrate, or inhibit the binding of an IHF protein. In some aspects, the interfering agent may be specific and competes, titrates, or inhibits the binding of an HU protein of a specific microbial species but does not inhibit HU proteins of other microbial species. In some aspects, the interfering agent may be cross reactive and competes, titrates, or inhibits binding of an HU protein of multiple species. In some embodiments, the multiple species are those recited in Table 1.

Aspects of the disclosure relate to an interfering agent capable of specifically competing, titrating, or inhibiting the binding of an HU protein such as, but not limited to:
(a) an isolated or recombinant HU antigenic polypeptide or antigenic fragment or equivalent each thereof;
(b) an isolated or recombinant polynucleotide that encodes the polypeptide of (a) or its compliment or a fragment or equivalent each thereof;
(c) an antibody or antigen binding fragment of the antibody or polypeptide that specifically recognizes or binds (a) or a fragment or equivalent each thereof; and/or
(d) an isolated or recombinant polynucleotide that encodes the antibody or antigen binding fragment of (c) or a fragment or equivalent each thereof.

Further aspects of the disclosure provide one or more interfering agents that can be administered alone or in combination with each other, alone or combined with another therapeutic agent such as an agent that kills or inhibits the growth of the organism creating the biofilm or an opportunistic infection, and/or an adjuvant or a pharmaceutically acceptable carrier. Some aspects of the disclosure also relate to a composition comprising, or alternatively consisting essentially thereof, or yet further consisting of these combinations. Further aspects relate to the use of the interfering agents in, for example, diagnostic, therapeutic, and functional assays as disclosed herein that include but are not limited to the use of interfering agents in the treatment of, and/or visualization and/or detection of biofilms.

This disclosure provides methods and compositions to inhibit or prevent infection of a host cell by a bacteria that exports an HU protein, the methods and compositions comprising, or alternatively consisting essentially of, or yet further consisting of, administering to a tissue exposed to or infected with the bacteria an effective amount of an bacteria-relevant antibody that specifically recognizes and binds the HU protein, thereby inhibiting or preventing infection of the host cell by the bacteria. The antibody can be polyclonal, monoclonal or a derivative of an antibody that recognizes and binds the bacteria-relevant HU protein. Multiple antibodies can be administered concurrently or sequentially along with supporting therapies as noted herein. Owing to the omnipresence of these DNABII proteins associated with the bacterial surface throughout the life cycle of the cell inclusive of all states, e.g. individual, aggregated or resident biofilm bacteria, antisera directed to HU proteins may interfere with interactions with the host cell surface including, attachment and subsequent invasion. Bacteria that can invade and propagate in host cells are protected from the host's immune system and antimicrobial therapy. Rendering bacteria incapable of binding and invasion makes them susceptible to clearance by the immune system and administered antimicrobials. The source of antibody against the HU protein can be elicited by either active vaccination of the host with HU protein or passive transfer of antiserum or an antibody against the HU protein.

This disclosure provides a method to inhibit or prevent infection of a cell by a bacteria that exports an HU protein. The method comprises, or alternatively consists essentially of, or yet further consists of, administering to a tissue infected with the bacteria an effective amount of an antibody that specifically recognizes and binds the HU protein, thereby inhibiting or preventing infection of the bacteria. The source of antibody against the HU family proteins can be elicited by either active vaccination of the host with the HU protein or passive transfer of antiserum or an antibody against proteins of the HU protein. The antibody can be polyclonal, monoclonal or a derivative of an antibody that recognizes and binds the bacteria-relevant HU protein. Multiple antibodies can be administered concurrently or sequentially along with supporting therapies as noted herein.

The administration can be in vitro in a culture or in vivo, by administration to a patient infected with the bacteria. When practiced in vivo, the method can be used to treat a subject infected with the bacteria by administering to the infected subject an effective amount of the antibody. In addition, when the subject is a non-human animal, the method can be used to test possible therapies or combination therapies prior to administration to a human. When practiced in vitro, the method is useful to screen for other therapeutic agents and combination therapies, such as small molecule drugs, that inhibit or prevent infection of the bacteria in a tissue.

Also provided are methods to treat a bacterial infection in subject in need thereof, wherein the subject is infected with a bacteria that comprises an HU protein, the method comprising, or alternatively consisting essentially of, or yet further consisting of, administering to the subject an effective amount of an antibody that specifically recognizes and binds the HU protein, thereby inhibiting or preventing infection of the bacteria. The antibody can be polyclonal, monoclonal or a derivative of an antibody that recognizes and binds the bacteria-relevant HU protein. The source of antibody against the HU protein can be elicited by either active vaccination of the host with the HU protein or passive transfer of antiserum or an antibody against proteins of the HU protein. Multiple antibodies can be administered concurrently or sequentially along with supporting therapies as noted herein.

Yet further provided are methods to treat a condition in a subject in need thereof, wherein the condition is associated with a bacterial infection wherein the bacteria comprises an HU protein, the method comprising, or alternatively consisting essentially of, or yet further consisting of, administering to the subject an effective amount of an antibody that specifically recognizes and binds the HU protein, thereby inhibiting or preventing infection of the bacteria. The source of antibody against the HU protein can be elicited by either active vaccination of the host with the HU protein or passive transfer of antiserum or an antibody against the HU protein. The antibody can be polyclonal, monoclonal or a derivative of an antibody that recognizes and binds the bacteria-relevant HU protein. Multiple antibodies can be administered concurrently or sequentially along with supporting therapies as noted herein.

Any of the above methods can further comprise, or alternatively consist essentially of, or yet further consist of, administering to the subject or the tissue or cell culture in vitro, an effective amount of one or more of an antimicrobial, an antigenic peptide or an adjuvant. The subject, in some aspects, is a non-human animal or a human patient.

The antibody, polypeptide or composition is administered locally or systemically by any appropriate method, e.g., to the site of infection or biofilm, topically, rectally, vaginally, ocularly, subcutaneous, intramuscularly, intraperitoneally, urethrally, intranasally, by inhalation or orally.

In some aspects, the subject is a pediatric patient and the antibody is administered in a formulation for the pediatric patient. In some aspects, the subject is an adult patient and the antibody is administered in a formulation for the adult patient.

In some aspects, the subject is a human patient and the antibody is administered in a formulation for human use. In some aspects, the subject is a non-human patient and the antibody is administered in a formulation for non-human use, e.g., a veterinary use.

A screen to identify potential therapeutic agents that inhibit or prevent infection of a cell by a bacteria that exports an HU protein and/or that disrupt or prevent biofilm formation is also disclosed. The screening method comprises, or alternatively consists essentially of, or yet consists of, contacting in vitro or administering in vivo to a tissue infected with the bacteria an agent and determining if the agent binds the HU protein. Methods to determining binding are known in the art and several non-limiting examples are described herein. In one aspect, if the agent binds the protein, the agent is a potential therapeutic agent and if the agent does not bind the protein, the agent is not a potential therapeutic agent. In another aspect, if the infection or biofilm is inhibited, disrupted, or prevented in vivo, the agent is a potential therapeutic agent and if infection is not inhibited or prevented, the agent is not a potential therapeutic agent. Methods of determining if the infection is inhibited or prevented are known in the art and several non-limiting examples are described herein; methods of determining if a biofilm is disrupted or prevented are known in the art and further disclosed herein. Non-limiting examples of potential therapeutic agents are from the group of: an antibody, an antibody derivative, a polypeptide, a polynucleotide, or a small molecule. Multiple antibodies can be administered concurrently or sequentially along with supporting therapies as noted herein. In a further aspect, the agent binds the protein and the binding is compared to the binding of anti-HU antisera to the protein, e.g., antisera directed against an HU protein.

This disclosure also provides isolated or recombinant polypeptides comprising, or alternatively consisting essentially of, or yet further consisting essentially of, an amino acid sequence of an HU antigenic protein, or an antigenic fragment or equivalent each thereof. In certain aspects, the disclosure relates to an isolated or recombinant polypeptide consisting essentially of an amino acid sequence selected from the amino acid sequences provided in Table 1, or an antigenic fragment or equivalent of each thereof. In certain aspects, the isolated or recombinant HU antigenic polypeptide is derived from *P. gingivalis*, and optionally, a polypeptide comprising, or alternatively consisting essentially of, or yet further amino acids AARKGINPKTKKSISI-PARKVVRF (SEQ ID NO: 13). In yet a further aspect, this disclosure provides mutated or recombinant HU antigenic polypeptides having the corresponding amino acid(s) to the *P. gingivalis* amino acids at positions 61 and/or 64 modified to I (or alternatively another hydrophobic amino acid that includes, but is not limited to V or F) and/or K. Use of the isolated or recombinant polypeptides as immunogens is disclosed herein. In some method aspects, such isolated or recombinant polypeptides may be used to generate antibodies that specifically recognize or bind these amino acid sequences. In additional method aspects, the isolated or recombinant polypeptides may be used in vaccine formulations or as interfering agents.

In certain aspects, the disclosure relates to one or more antibodies or antigen binding fragments that are specific to an HU polypeptide, protein or recombinant HU protein or antigenic polypeptide In certain aspects, the disclosure relates to an antibody or antigen binding fragment that specifically recognizes or binds an isolated or recombinant polypeptide consisting essentially of an amino acid sequence selected from the amino acid sequences provided in Table 1, or a polypeptide comprising, or alternatively consisting essentially of, or yet further amino acids AARKGINPKTKKSISIPARKVVRF (SEQ ID NO: 13), or an antigenic fragment or equivalent of each thereof. Use of the antibodies or antigen binding fragments is disclosed herein. In some method aspects, such antibodies or antigen binding fragments may be used as interfering agents. In additional method aspects, the antibodies or antigen binding fragments may be used in diagnostic methods.

This disclosure also provides isolated or recombinant polynucleotides encoding one or more of the above-identified isolated, mutated or recombinant polypeptides or antibodies or a fragment of each thereof. In certain aspects, the disclosure relates to a polynucleotide encoding an isolated, mutated or recombinant polypeptide consisting essentially of an amino acid sequence selected from the amino acid sequences provided in Table 1 or a polypeptide comprising, or alternatively consisting essentially of, or yet further amino acids AARKGINPKTKKSISIPARKVVRF (SEQ ID NO: 13), or an antigenic fragment or equivalent of each thereof, or an antibody or antigen binding fragment that bind specifically to one or more of these polypeptides. Vectors comprising the isolated polynucleotides are further provided. In aspects involving more than one isolated polypeptide disclosed herein, the isolated polynucleotides may be contained within a polycistronic vector.

Isolated host cells comprising one or more of isolated, mutated or recombinant polypeptides or isolated, mutated or recombinant polynucleotides or the vectors, described herein are further provided.

The polynucleotides, polypeptides, antibodies, antigen binding fragment, or vectors or host cells can further comprise a detectable label. In one aspect, the detectable label is not a naturally occurring, detectable compound such as a fluorescent polynucleotide or amino acid.

Compositions comprising a carrier and one or more of an isolated, mutated or recombinant polypeptide disclosed herein, an isolated, mutated or recombinant polynucleotide disclosed herein, a vector disclosed herein, an isolated host cell disclosed herein, or an antibody or fragment thereof, are also provided. The carriers can be one or more of a solid support, a medical device like a stent or dental implant, or a liquid such as a pharmaceutically acceptable carrier. The compositions can further comprise an adjuvant, an antimicrobial or an antigenic peptide or an antimicrobial other than the disclosed antibodies or fragments thereof.

The compositions can further comprise additional biologically active agents. A non-limiting example of such is an antimicrobial agent such as other vaccine components (i.e., antigenic peptides) such as surface antigens, e.g., important virulence factors such as the gingipains (RgpA, RgbB, and Kgp), the RagB lipoprotein, fimbrial genes such as FimA and Mfa, outer membrane vesicles (OMV), and the conserved C-terminal domain essential for translocation across the membrane (see Kong et al (2015) *Porphyromonas gingivalis* B cell Antigen Epitope Vaccine, pIRES-ragB'-mGITRL, Promoted RagB-Specific Antibody Production and Tfh Cells Expansion. *Scandinavian Journal of Immunology*, 81(6), 476-482 and Zheng et al (2013) Enhancing specific-antibody production to the ragB vaccine with GITRL that expand Tfh, IFN-γ(+) T cells and attenuates *Porphyromonas gingivalis* infection in mice. *PloS One*, 8(4), e59604, and Bai et al (2015) Immunoreactive antigens recognized in serum samples from mice intranasally immunized with *Porphyromonas gingivalis* outer membrane vesicles. *Pathogens and Disease*, 73(3), ftu006-ftu006 and Kadowski et al (1998) Arg-gingipain Acts as a Major Processing Enzyme for Various Cell Surface Proteins in *Porphyromonas gingivalis*. *The Journal of Biological Chemistry*, 273(44), 29072-29076 and Chen et al (2004) Comparative whole-genome analysis of virulent and avirulent strains of *Porphyromonas gingivalis*. *Journal of Bacteriology*, 186(16), 5473-5479 and antimicrobial agents.

This disclosure also provides a method for producing an antigenic peptide by growing or culturing a host cell comprising an isolated polynucleotide encoding an antigenic peptide as described above under conditions that favor the expression of the polynucleotide. The polypeptide produced by this method can be isolating for further in vitro or in vivo use. Alternatively, the polypeptides can be produced using chemical synthetic methods known to those of skill in the art.

A kit is also provided for diagnostic or therapeutic use comprising an interfering agent or agents as described above and instructions for use. A kit is also provided to perform screens for new drugs and/or combination therapies as provided herein.

DETAILED DESCRIPTION

Figure 1:
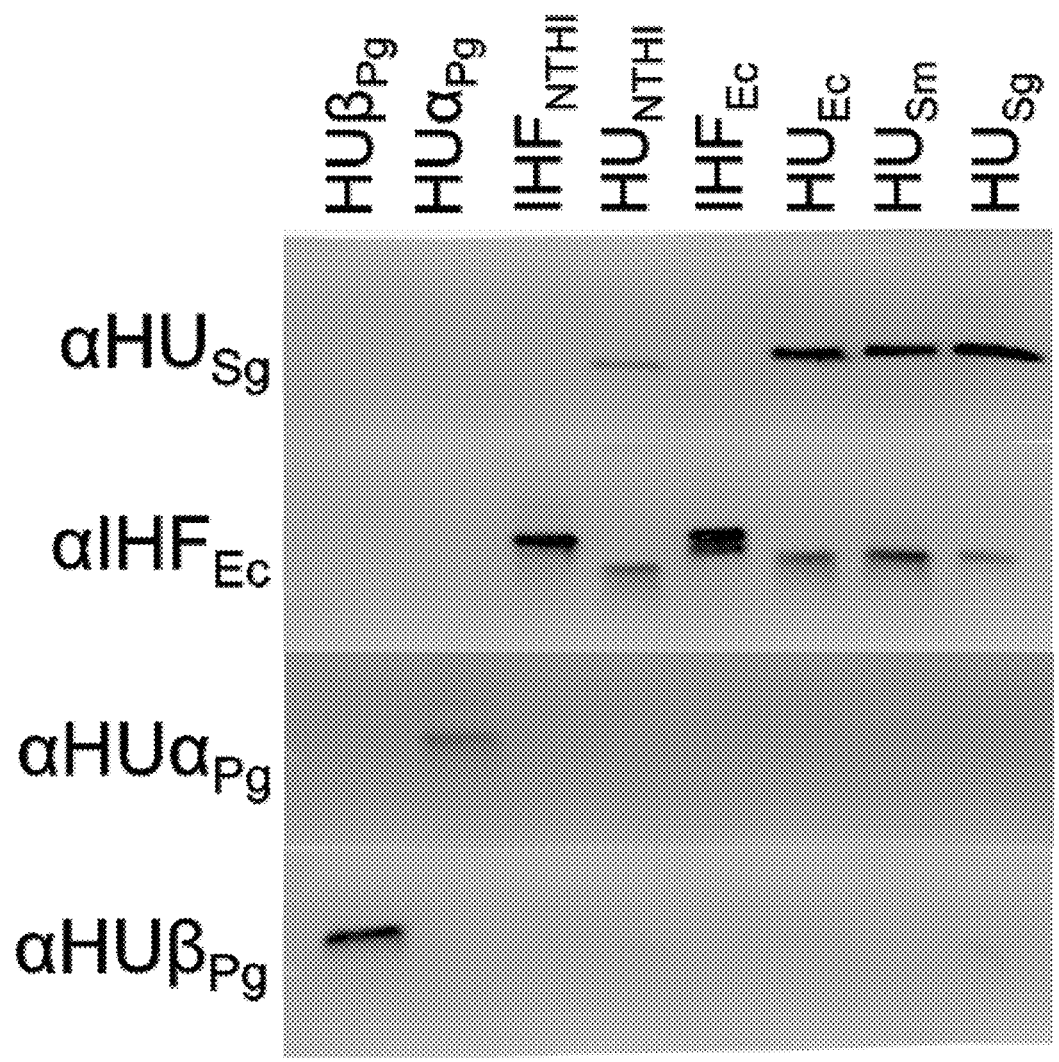
FIG. 1 is a western blot analysis of the recognition of DNABII proteins by DNABII antisera. Antisera derived against *P. gingivalis* (Pg) DNABII proteins displays no cross reactivity, while antisera derived against *E. coli* (Ec) IHF and *S. gordonii* (Sg) HU display wide cross-reactivity. NTHI (non-typable *Haemophilus influenzae*).

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety, some of which are identified by an Arabic number, the full citation for which can be found immediately preceeding the claims. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Green and Sambrook eds. (2012) Molecular Cloning: A Laboratory Manual, $4^{th}$ edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, $6^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, $2^{nd}$ edition; Guisan ed. (2006) Immobilization of Enzymes and Cells; Perbal (1988) A Practical Guide to Molecular Cloning, $2^{nd}$ edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, $4^{th}$ edition; and Herzenberg et al. eds (1996) Weir's Handbook of Experimental Immunology, $5^{th}$ edition.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

A "biofilm" intends an organized community of microorganisms that at times adhere to the surface of a structure, that may be organic or inorganic, together with the polymers such as DNA that they secrete and/or release. The biofilms are very resistant to microbiotics and antimicrobial agents. They live on gingival tissues, teeth and restorations, causing caries and periodontal disease, also known as periodontal plaque disease. They also cause middle ear infections. Biofilms can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. They cause vaginal infections and lead to life-threatening systemic infections in people with hobbled immune systems. Biofilms also are involved in numerous diseases, including but not limited to those caused by *Aggregatibacter actinomycetemcomitans, Borrelia burgdorferi* (e.g., B31), *Bordetella pertussis* (e.g., Tohama I), *Burkholderia pseudomallei* (e.g., 668), *Burkholderia cenocepacia* (e.g., HI2424), *Escherichia coli* (e.g., K12 MG1655), *Enterococcus faecalis* (e.g., V583), *Haemophilus influenzae* (e.g., Rd KW20), *Helicobacter pylori* (e.g., 26695), *Klebsiella pneumoniae, Moraxella catarrhalis* (e.g., RH4), *Mycobacterium smegmatis* (e.g., MC2), *Mycobacterium tuberculosis* (e.g., CDC1551), *Neisseria gonorrhoeae* (e.g., FA1090), *Neisseria meningitidis* (e.g., MC58), *Pseudomonas aeruginosa, Porphyromonas gingivalis* (e.g., W83), *Prevotella intermedia* (e.g., 17), *Prevotella melaninogenica* (e.g., ATCC® 25845), *Staphylococcus aureus* (e.g., MW2), *Staphylococcus epidermidis* (e.g., RP62A), *Streptococcus agalactiae* (e.g., 2603V/R), *Streptococcus bovis, Streptococcus gallolyticus* (e.g., UCN34), *Streptococcus gordonii* (e.g., NCTC 7868 (Challis)), *Streptococcus mutans* (e.g., UA159), *Streptococcus pneumoniae* (e.g., R6), *Streptococcus pyogenes* (e.g., MGAS10270), *Streptococcus sobrinus* (e.g., 6715), *Salmonella enterica* (e.g., *typhi*, CT18), *Treponema denticola* (e.g., ATCC® 35405), *Treponema palladum* (e.g., Nichols), *Vibrio cholera* (e.g., El Tor, N16961). Additional organisms known to associate with and/or form biofilms include but are not limited to *Campylobacter* spp., *Candida* spp., *Legionella pneumophila*, and *Listeria monocytogenes*. For example, cystic fibrosis patients have *Pseudomonas* infections that often result in antibiotic resistant biofilms. Other diseases associated with biofilms include, but are not limited to, lung infections of cystic fibrosis patients, otitis media, native valve infectious endocarditis, osteomyelitis, rhinosinusitis, prostatitis, urinary tract infection, wounds, dental caries and periodontitis. Foodborne pathogens, such as but not limited to some of the above listed organisms (e.g., *Listeria monocytogenes, Escherichia coli, Salmonella enterica*) may also form biofilms on the food which they contaminate. Disease causing biofilms in animals (e.g., *Escherichia coli, Salmonella*, and *Shigella* species) may also cause downstream food contamination and/or disease in human hosts. Further, biofilms need not be of one homogeneous microbial population and may incorporate other pathogens and even host cells. In addition to being associated with disease—both nosocomial and otherwise—and food contamination, biofilms are often causes of industrial contamination, most notably in relation to process waters and surfaces in contact therewith. Complications involving organisms that form biofilm as industrial contaminants include but are not limited to biocorrosion, biofouling, and equipment damage as a result of biofilm formation. Non-limiting exemplary organisms associated with biofilms in industrial settings include those disclosed in Ferrera et al. (2015) Biofouling 31(2):173-80 and *Desulfovibrio* species. Additional details regarding biofilms may be found in, for example, Donlan (2002) Emerging Infectious Diseases 8(9):881-890.

A "DNABII polypeptide or protein" intends a DNA binding protein or polypeptide that is composed of DNA-binding domains and thus have a specific or general affinity for microbial DNA. In one aspect, they bind DNA in the minor grove. Non-limiting examples of DNABII proteins are an integration host factor (IHF) protein and a histone-like protein (HU). Other DNA binding proteins that may be associated with the biofilm include DPS (Genbank Accession No.: CAA49169), H—NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" of "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes.

"HU" or "histone-like protein" refers to a class of proteins that, in some species, may be heterodimeric or homdimeric. HU proteins are known to bind DNA junctions. The complete amino acid sequence of *E. coli* HU was reported by Laine et al. (1980) Eur. J. Biochem 103(3):447-481.

The following table lists non-limiting exemplary sequences for HU proteins and the species from which they originate:

TABLE 1

A listing of non-limiting exemplary HU protein sequences from a variety of species.

| SEQ ID | Species | Ref No. | Exemplary Sequence |
|---|---|---|---|
| SEQ ID NO 1 | Tannerella forsythia | WP_041591297.1 | MNKTEFINAVAEKAGLSKVDGKKAVEAM VKTIQGEMKKGEKVSILGFGSFSVVEKAS RKGVNPQTKKVINIPARKVIKFKPGTDL |
| SEQ ID NO 2 | Porphyromonas endodontalis | WP_004334454.1 | MNKTEFIAAVAEKAGLTKADAQRAVNAF TEVVKETMEKGDRLPLVGFGTFSVSQRKA REGKNPRTGETIKIAARKVVHFKPGANLD LK |
| SEQ ID NO 3 | Porphyromonas macacae | WP_025003580.1 | MNKSEFIAEVAAKAGMTKVDAQKSVNAF IEVIQEQMKKGEKVALLGFGTFSVTQKAA RTGINPKTKKAIKIPARKAVKFKAGSALDV |
| SEQ ID NO 4 | Bergeyella zoohelcum | WP_002662711.1 | MNKTDFIAAVAEKANLTKADAQRAVNAF AEVVTEQMNAGEKIALIGFGTFSVSERAA RKGINPATKQPINIPAKMVAKFKPGT |
| SEQ ID NO 5 | Parabacteroides johnsonii | WP_008154292.1 | MNKTEFINAVAEKSGLSKVDAKKAVEAF VETVSSELKEGGKVALLGFGSFSVAEKAA RKGVNPKTKQPIEIPARKSVKFKAGAEL |
| SEQ ID NO 6 | Porphyromonas cangingivalis | WP_025837655.1 | MNKTEFISAVAEKAGATKVDTKAIVDAA VAVIAEEMKKGEKVAILGFGTFSVVERAK REGFNPRTKEKIKIPARKIVKFKPGSDLDI |
| SEQ ID NO 7 | Bacteroides faecichinchillae | WP_025073728.1 | MNKSELISAMATEAQMSKADAKRALEAFI TSVTNAMKAGDKVSLVGFGTFAVSERAA RTGINPSTKASITIPAKKVAKFKPGAEL |
| SEQ ID NO 8 | Odoribacter splanchnicus | WP_013611412.1 | MNKAQLIDAIAEKAGLTKADSKKALEAFV ETVGEALKGGDKVALIGFGSFSVSERSARS GRNPQTGKTITIPAKKVVKFKAGAEL |
| SEQ ID NO 9 | Bacteroides pyogenes | WP_027325691.1 | MNKSELVSAMAAEAQMSKADAKKALDA FISSVTKAMKAGDKVSLVGFGTFSVSERS ARTGINPSTKATITIPAKKVAKFKAGAEL |
| SEQ ID NO 10 | Saprospira grandis | WP_015691662.1 | MNKGDLIDKIAEAAGLKKADAAAALNAT LETIADTLKAGQKITLVGFGTFDVNYRAA RKGINPSTQKEIQISDKVTVKFKAG |

TABLE 1-continued

A listing of non-limiting exemplary HU protein sequences from a variety of species.

| SEQ ID | Species | Ref No. | Exemplary Sequence |
|---|---|---|---|
| SEQ ID NO 11 | Porphyromonas gingivalis | WP_004583766.1 | MNKTDFIAAVAEKANLTKADAQRAVNAF AEVVTEQMNAGEKIALIGFGTFSVSERAA RKGINPKTKKSISIPARKVVRFKPGSTLELK |

Not to be bound by theory, Applicant submits that one or more of the above listed HU polypeptide sequences may be antigenically distinct relative to other subspecies, species, genus, family, order, and/or class of microbial pathogen; thus, utilizing interfering agents that target the antigenically distinct elements of these pathogens may elicit a highly specific response. In some embodiments, the antigenic similarity or distinctiveness of an HU protein may be determined according to methods described herein below based on the cross-reactivity of HU antibodies or antigen binding fragments of one species with the HU protein of another species.

As used herein the term "same species" used in relation to a microbial pathogen refers to a member of the same taxonomic species; the term "highly related species" refers to species exhibiting antigenic similarity between HU proteins within the same taxonomic genus, family, order, and/or class.

The term "surface antigens" or "surface proteins" refers to proteins or peptides on the surface of cells such as bacterial cells. Examples of surface antigens are outer membrane proteins such as RgpA (Genbank Accession No.: BAG34488.1), RgpB (Genbank Accession No.: BAG34488.1), Kgp (Genbank Accession No.: BAG34247.1), RagB (Genbank Accession No.: BAG32813.1), FimA (Genbank Accession No.: BAG-32699.1) and Mfa1 (Genbank Accession No.: BAH90730.1).

"Microbial DNA" intends single or double stranded DNA from a microorganism that produces a biofilm.

"Inhibiting, preventing or breaking down" a biofilm intends the prophylactic or therapeutic reduction in the structure of a biofilm. In certain aspects, this intends a recution in the formation of the DNA/protein matrix that is a component of a microbial biofilm.

To "specifically" inhibit, prevent or breakdown a biofilm intends the prophylactic or therapeutic reduction in the structure of a biofilm of an HU protein from a single or highly related species. The term "selectively" may be used in a similar manner. Both terms may also be used in methods relating to inhibition or prevention of bacterial infection; i.e. to "specifically" or "selectively" inhibit or prevent bacteria from infecting a cell or tissue intends the inhibition or prevention where the bacteria comprise an HU protein from a single or highly related species.

An "interfering agent" or "interfering HU agent" intends an agent that any one or more of competes, inhibits, prevents, titrates a HU to a microbial DNA, inhibits or prevents a bacteria from infecting a cell or tissue, or breaks down a microbial biofilm (e.g., by disrupting the structural integrity of the eDNA based extracellular matrix). It can be any one or more of a chemical or biological molecule. Examples of such agents, without limitation, include:

(a) an isolated or recombinant HU polypeptide or fragment or equivalent each thereof;

(b) an isolated or recombinant polynucleotide that encodes the polypeptide of (a) or its compliment or a fragment or equivalent each thereof;

(c) an antibody or antigen binding fragment of the antibody or antigen binding polypeptide that specifically recognizes or binds (a) or a fragment or equivalent each thereof; and/or (d) an isolated or recombinant polynucleotide that encodes the antibody or antigen binding fragment of (c) or a fragment or equivalent each thereof.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets.

The term "protein," "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity as compared to a reference antibody or antigen binding fragment. Non-limiting examples of relevant reference antibody or antigen binding fragment include an antibody or antigen binding fragment thereof that specifically binds an HU fragment with an I amino acid residue at position 61, an antibody or antigen binding thereof that specifically binds any one of the HU fragments listed in Table 1, and an antibody or antigen binding fragment that binds an HU protein of the same species or a highly related species as the target microbial pathogen. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW (available at the web address:align.genome.jp, last accessed on Mar. 7, 2011.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, microspheres, microparticles, or nanoparticles (comprising e.g., biodegradable polymers such as Poly(Lactic Acid-co-Glycolic Acid)), and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

A "biologically active agent" or an active agent disclosed herein intends one or more of an isolated or recombinant polypeptide, an isolated or recombinant polynucleotide, a vector, an isolated host cell, or an antibody, as well as compositions comprising one or more of same.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application. Administration can be for use in industrial as well as therapeutic applications.

An agent (antibody or fragment thereof, polypeptide or polynucleotide, or cell) of the present disclosure can be administered for therapy by any suitable route of administration. It will also be appreciated that the optimal route will vary with the condition and age of the recipient, and the disease being treated.

As used herein the terms "antigenic" and "immunogenic" are used interchangeably as descriptors to indicate that a particular agent or composition such as a protein or polypeptide that is capable of stimulating the production of an antibody.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in breaking down a biofilm or reduction or prevention of the bacterial infection. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The term "conjugated moiety" refers to a moiety that can be added to an isolated chimeric polypeptide by forming a covalent bond with a residue of chimeric polypeptide. The moiety may bond directly to a residue of the chimeric polypeptide or may form a covalent bond with a linker which in turn forms a covalent bond with a residue of the chimeric polypeptide.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

A "microsphere" intends a biofilm-carrying and/or compound-carrying (e.g., drug-carrying) particulate or granular material within the particular size range recited. As used herein, a microsphere consisting of particles 50 millimeters or less in diameter, and 1 micron or more (e.g., 1 to 100 or alternatively, or alternatively, 1 to 75 microns, or alternatively 1 to 50, or alternatively 1 to 25, or alternatively 1 to 10 microns) in diameter. Non-limiting examples of such include hollow microspheres that can, in some aspects, contain a pharmaceutical or drug, microcapsules (in which the excipient forms a skin or shell that surrounds and contains a cargo, such as a drug), and microparticles, which are used as a generic term for any particles in the recited size range, whether spherical or not, as those terms are typically used in the art.

A "biodegradable polymer" intends polymers that are biocompatible and can degrade in vivo by bodily processes to products that are readily disposable by the body and should not accumulate in the body.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, are preferentially used. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to microspheres made from materials which undergo bioabsorption in vivo over a period of time such that long term accumulation of the material in the patient is avoided. The biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the microspheres used in this invention.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, di stearoylphosphatidylethanolamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides or antibodies described here. It is contemplated that the conjugation of a polymer to the polypeptide or antibody is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides;

lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

As used herein the term "eDNA" refers to extracellular DNA found as a component to microbial biofilms.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., PCT International Application Publication No. WO 95/27071. Ads do not require integration into the host cell genome. Recombinant Ad derived vectors, particularly those that reduce the potential for recombination and generation of wild-type virus, have also been constructed. See, PCT International Application Publication Nos. WO 95/00655 and WO 95/11984, Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, species-ized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-IHF, anti-HU, anti-OMP P5, for example, refers to a monoclonal or polyclonal antibody that binds and/or has an affinity to a particular protein. For example, "anti-HU" refers to an antibody that binds to the HU protein.

The antibodies can be polyclonal, monoclonal, multispecific (e.g., bispecific antibodies), and antibody fragments, so long as they exhibit the desired biological activity. Antibodies can be isolated from any suitable biological source, e.g., murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like.

The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody," as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine. Non-human antibodies may be generated according to the same or a similar procedure to generate "species-ized" antibodies.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. While the term "label" generally intends compositions covalently attached to the composition to be detected, it specifically excludes naturally occurring nucleosides and amino acids that are known to fluoresce under certain conditions (e.g., temperature, pH, etc.) and generally any natural fluorescence that may be present in the composition to be detected. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, a fluorescent label sold under CASCADE BLUE®, and a fluorescent label sold under TEXAS RED®. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen disclosed herein is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

"Immune response" broadly refers to the antigen-specific responses of lymphocytes to foreign substances. The terms "immunogen" and "immunogenic" refer to molecules with the capacity to elicit an immune response. All immunogens are antigens; however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

As used herein, the term "inducing an immune response in a subject" is a term well understood in the art and intends that an increase of at least about 2-fold, at least about 5-fold, at least about 10-fold, at least about 100-fold, at least about 500-fold, or at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), a resin sold under POLYHIPE® resin (obtained from Aminotech, Canada), polyamide resin (obtained from Peninsula Laboratories), polystyrene resin grafted with polyethylene glycol (a resin sold under TENTAGEL®, Rapp Polymere, Tubingen, Germany) or polydimethylacrylamide resin (obtained from Milligen/Biosearch, Calif.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Polypeptides

Aspects of the disclosure relate to an isolated or recombinant HU polypeptide or fragment or equivalent each thereof, e.g., an antigenic polypeptide or protein, capable of competing, titrating, or inhibiting the binding of an HU protein.

This disclosure also provides isolated or recombinant polypeptides comprising or alternatively consisting essentially of, or yet further consisting of, two or more, or three or more, four or more, five or more, six or more, seven or more, eight or more, nine or more, ten or more, eleven or more, twelve or more, thirteen or more of all fourteen of the isolated polypeptides or a fragment or an equivalent of each thereof. Non-limiting examples of such include isolated or recombinant polypeptides comprising the amino acid sequences listed in Table 1 or fragments or equivalents thereof, and equivalents of each thereof. Further non-limiting examples include an isolated or recombinant polypeptide comprising, or alternatively consisting essentially of, or yet further amino acids AARKGINPKTKKSISIPARKVVRF (SEQ ID NO: 13). In yet a further aspect, this disclosure provides mutated or recombinant HU antigenic polypeptides having the corresponding amino acid(s) to the *P. gingivalis* amino acids at positions 61 and/or 64 modified to I (or alternatively another hydrophobic amino acid such as V or F) and/or K. Biological equivalents of these polypeptides are further included in this disclosure with the proviso that the sequences do not include whole, isolated wildtype sequences.

In one embodiment, any polypeptide or protein having sequence identity to the wildtype polypeptides or those disclosed in Pedulla et al. (1996) PNAS 93:15411-15416 is excluded from this disclosure.

In any of the above embodiments, a peptide linker can be added to the N-terminus or C-terminus of the polypeptide. A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO: 14). Other examples include Gly-Gly-Gly; Gly-Pro-Ser-Leu (SEQ ID NO: 15); Gly-Pro-Ser; Pro-Ser-Leu-Lys (SEQ ID NO: 16); Gly-Pro-Ser-Leu-Lys (SEQ ID NO: 17) and Ser-Leu-Lys-Leu (SEQ ID NO: 18).

The isolated polypeptides disclosed herein are intended to include isolated wildtype and recombinantly produced polypeptides and proteins from prokaryotic and eukaryotic host cells, as well as muteins, analogs and fragments thereof, examples of such cells are described above. In some embodiments, the term also includes antibodies and anti-idiotypic antibodies as described herein. Such polypeptides can be isolated or produced using the methods known in the art and briefly described herein.

It is understood that functional equivalents or variants of the wild type polypeptide or protein also are within the scope of this disclosure, for example, those having conservative amino acid substitutions of the amino acids. Other analogs include fusion proteins comprising a protein or polypeptide disclosed herein which can include a polypeptide joined to an antigen presenting matrix.

In a further aspect, the polypeptides are conjugated or linked to a detectable label. Suitable labels are known in the art and described herein.

In a yet further aspect, the polypeptides with or without a detectable label can be contained or expressed on the surface of a host prokaryotic or eukaryotic host cell, such as a dendritic cell.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins disclosed herein by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Green and Sambrook (2012) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies as described below. The polypeptides disclosed herein are useful in an in vitro assay system to screen for agents or drugs, which modulate cellular processes.

It is well known to those skilled in the art that modifications can be made to the peptides disclosed herein to provide them with altered properties. As used herein the term "amino acid" refers to either natural and/or unnatural or synthetic amino acids, including, but not limited to, the twenty commonly occurring amino acids alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V) and both the D or L optical isomers thereof, and amino acid analogs and peptidomimetics. The term "amino acid" is used herein in the conventional sense to refer to organic chemical moieties which comprise an amino group (—$NH_2$) and a carboxylic acid group (—COOH). Amino acids may be further grouped based on their side chains, e.g. "hydrophobic amino acids" are those with hydrophobic side chains, including, but not limited to, alanine (A), isoleucine (I), leucine (L), valine (V), phenylalanine (F), tryptophan (W) or tyrosine (Y) and "hydrophilic amino acids" are those with charged or polar side chains, including, but not limited to, arginine (R), asparagine (N), aspartic acid (D), glutamine (Q), glutamic acid (E), histidine (H), lysine (K), serine (S), and threonine (T).

A peptide of three or more amino acids is commonly called an oligopeptide if the peptide chain is short. If the peptide chain is long, the peptide is commonly called a polypeptide or a protein. Peptides disclosed herein can be modified to include unnatural amino acids. Thus, the peptides may comprise D-amino acids, a combination of and L-amino acids, and various "designer" amino acids (e.g., beta-methyl amino acids, C-alpha-methyl amino acids, and N-alpha-methyl amino acids, etc.) to convey special properties to peptides. Additionally, by assigning specific amino acids at specific coupling steps, peptides with alpha-helices, beta turns, beta sheets, gamma-turns, and cyclic peptides can be generated. Generally, it is believed that alpha-helical secondary structure or random secondary structure may be of particular use.

The polypeptides disclosed herein also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of E. coli, mutant derivatives of cholera toxin, CPG oligonucleotides, and adjuvants derived from squalene.

This disclosure also provides a pharmaceutical composition comprising or alternatively consisting essentially of, or yet further consisting of, any of a polypeptide, analog, mutein, or fragment disclosed herein, alone or in combination with each other or other agents, such an antibiotic and an acceptable carrier or solid support.

These compositions are useful for various diagnostic and therapeutic methods as described herein. In specific embodiments, it is envisioned that the polypeptides disclosed herein may be used in the generation of antibodies or a more generalized immune response. For example, the use of said polypeptides as immunogens may be useful in the generation of antibodies according to the above disclosed methods, as well as in diagnostic and therapeutic methods disclosed below. Conceivable embodiments according to the present disclosure include but are not limited to use of the isolated or recombinant polynucleotides to characterize, identify, purify, or otherwise assay the antibodies disclosed herein; use of the isolated or recombinant polynucleotides to generate the antibodies disclosed herein; or use of the isolated or recombinant polynucleotides alone or in combination with the antibodies disclosed herein in a vaccine or therapeutic formulation as contemplated herein.

Antibodies and Derivatives Thereof

This disclosure also provides an antibody that binds and/or specifically recognizes and binds an isolated polypeptide for use in the methods disclosed herein. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody, examples of such are provided herein. In one aspect, the antibody is detectably labeled or further comprises a detectable label conjugated to it. Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein.

Antibodies also can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Antibodies specific to HU can be generated by injection of polypeptides corresponding to different epitopes of HU. For example, antibodies can be generated using the amino acid sequences or fragments thereof disclosed in Table 1. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SAS, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Mumma 93:154-161) that are capable of producing a repertoire of human antibodies, as known in the art and/or as described herein. Such techniques, include, but are not limited to, ribosome display, e.g., Wanes et al. (1997) Proc. Natl. Acad. Sci. USA, 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052, Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody or fragment thereof disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbiol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or to reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e., the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In certain aspects, the disclosure relates to an antibody or antigen binding fragment that specifically recognizes or binds an isolated or recombinant polypeptide that comprises or consisting essentially of an amino acid sequence selected from the amino acid sequences provided in Table 1, or a fragment or equivalent of each thereof. In certain aspects, the disclosure relates to an antibody or antigen binding fragment that specifically recognizes or binds an isolated or recombinant polypeptide that comprises or consisting essentially of the amino acid sequence AARKGINPKTKKSISI-PARKVVRF (SEQ ID NO: 13) or an antibody or antigen-binding fragment that specifically recognizes and binds a mutated or recombinant HU antigenic polypeptide having the corresponding amino acid(s) to the *P. gingivalis* amino acids at positions 61 and/or 64 modified to I (or alternatively another hydrophobic amino acid, that includes, but is not limited to V or F) and/or K, respectively.

In some of the aspects of the antibodies provided herein, the antibody binds an HU protein or polypeptice with a dissociation constant ($K_D$) of less than $10^{-4}$M, $10^{-5}$M, $10^{-6}$M, $10^{-7}$M, $10^{-8}$M, $10^{-9}$M, $10^{-10}$ M, $10^{-11}$M, or $10^{-12}$M. In some of the aspects of the antibodies provided herein, the antigen binding site specifically binds to an HU protein.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.

2) Amino acids with acidic side chains: aspartic acid, glutamic acid.

3) Amino acids with uncharged polar side chains: asparagine, glutamine, serine, threonine, tyrosine.

4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind an HU protein with similar specificity and sensitivity profiles as the disclosed antibodies. This may be tested by way of the binding assays.

The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include:

```
Human IgD constant region, Uniprot: P01880
                                       (SEQ ID NO: 19)
APTKAPDVFPIISGCRHPKDNSPVVLACLITGYHPTSVTVTWYMGTQSQP
QRTFPEIQRRDSYYMTSSQLSTPLQQWRQGEYKCVVQHTASKSKKEIFRW
PESPKAQASSVPTAQPQAEGSLAKATTAPATTRNTGRGGEEKKKEKEKEE
QEERETKTPECPSHTQPLGVYLLTPAVQDLWLRDKATFTCFVVGSDLKDA
HLTWEVAGKVPTGGVEEGLLERHSNGSQSQHSRLTLPRSLWNAGTSVTCT
LNHPSLPPQRLMALREPAAQAPVKLSLNLLASSDPPEAASWLLCEVSGFS
PPNILLMWLEDQREVNTSGFAPARPPPQPGSTTFWAWSVLRVPAPPSPQP
ATYTCVVSHEDSRTLLNASRSLEVSYVTDHGPMK
Human IgG1 constant region, Uniprot: P01857
                                       (SEQ ID NO: 20)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK
Human IgG2 constant region, Uniprot: P01859
                                       (SEQ ID NO: 21)
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDISVEWESNGQPENNYKTTPPMLDSDGSFFLYSKLTVDKSRWQQGN
VFSCSVMHEALHNHYTQKSLSLSPGK
Human IgG3 constant region, Uniprot: P01860
                                       (SEQ ID NO: 22)
ASTKGPSVFPLAPCSRSTSGGTAALGCLVKDYFPEPVTVSWNSGALTSGV
HTFPAVLQSSGLYSLSSVVTVPSSSLGTQTYTCNVNHKPSNTKVDKRVEL
KTPLGDTTHTCPRCPEPKSCDTPPPCPRCPEPKSCDTPPPCPRCPEPKSC
DTPPPCPRCPAPELLGGPSVFLFPPKPKDTLMISRTPEVTCVVVDVSHED
PEVQFKWYVDGVEVHNAKTKPREEQYNSTFRVVSVLTVLHQDWLNGKEYK
CKVSNKALPAPIEKTISKTKGQPREPQVYTLPPSREEMTKNQVSLTCLVK
GFYPSDIAVEWESSGQPENNYNTTPPMLDSDGSFFLYSKLTVDKSRWQQG
NIFSCSVMHEALHNRFTQKSLSLSPGK
Human IgM constant region, Uniprot: P01871
                                       (SEQ ID NO: 23)
GSASAPTLFPLVSCENSPSDTSSVAVGCLAQDFLPDSITLSWKYKNNSDI
SSTRGFPSVLRGGKYAATSQVLLPSKDVMQGTDEHVVCKVQHPNGNKEKN
VPLPVIAELPPKVSVFVPPRDGFFGNPRKSKLICQATGFSLRPRQIQVSWLR
EGKQVGSGVTTDQVQAEAKESGPTTYKVTSTLTIKESDWLGQSMFTCRVD
HRGLTFQQNASSMCVPDQDTAIRVFAIPPSFASIFLTKSTKLTCLVTDLT
TYDSVTISWTRQNGEAVKTHTNISESHPNATFSAVGEASICEDDWNSGER
FTCTVTHTDLPSPLKQTISRPKGVALHRPDVYLLPPAREQLNLRESATIT
CLVTGFSPADVFVQWMQRGQPLSPEKYVTSAPMNIPEPQAPGRYFAHSILT
VSEEEWNTGETYTCVAHEALPNRVTERTVDKSTGKPTLYNVSLVMSDTAG
TCY
Human IgG4 constant region, Uniprot: P01861
                                       (SEQ ID NO: 24)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK
Human IgA1 constant region, Uniprot: P01876
                                       (SEQ ID NO: 25)
ASPTSPKVFPLSLCSTQPDGNVVIACLVQGFFPQEPLSVTWSESGQGVTA
RNFPPSQDASGDLYTTSSQLTLPATQCLAGKSVTCHVKHYTNPSQDVTVP
CPVPSTPPTPSPSTPPTPSPSCCHPRLSLHRPALEDLLLGSEANLTCTLT
GLRDASGVTFTWTPSSGKSAVQGPPERDLCGCYSVSSVLPGCAEPWNHGK
TFTCTAAYPESKTPLTATLSKSGNTFRPEVHLLPPPSEELALNELVTLTC
LARGFSPKDVLVRWLQGSQELPREKYLTWASRQEPSQGTTTFAVTSILRV
AAEDWKKGDTFSCMVGHEALPLAFTQKTIDRLAGKPTHVNVSVVMAEVDG
TCY
Human IgA2 constant region, Uniprot: P01877
                                       (SEQ ID NO: 26)
ASPTSPKVFPLSLDSTPQDGNVVACLVQGFFPQEPLSVTWSESGQNVTA
RNFPPSQDASGDLYTTSSQLTLPATQCPDGKSVTCHVKHYTNPSQDVTVP
CPVPPPPPCCHPRLSLHRPALEDLLLGSEANLTCTLTGLRDASGATFTWT
PSSGKSAVQGPPERDLCGCYSVSSVLPGCAQPWNHGETFTCTAAHPELKT
PLTANITKSGNTFRPEVHLLPPPSEELALNELVTLTCLARGFSPKDVLVR
WLQGSQELPREKYLTWASRQEPSQGTTTFAVTSILRVAAEDWKKGDTFSC
MVGHEALPLAFTQKTIDRMAGKPTHVNVSVVMAEVDGTCY
Human Ig kappa constant region, Uniprot: P01834
                                       (SEQ ID NO: 27)
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKS
FNRGEC
```

In some aspects of the antibodies provided herein, the antibody binds to the epitope bound by DNABII antibodies.

In some aspects of the antibodies provided herein, the antibody contains structural modifications to facilitate rapid binding and cell uptake and/or slow release. In some aspects, the DNABII antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al, (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Patent Application Publication No. 2006/0211088; PCT International Application Publication WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments ($V_H$—$C_H1$-VH—$C_H1$) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58:671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677, 425) and amino acid mutations in the Fc hinge region to decrease die biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields, R. L. et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydral groups (Koyama 1994 Chem. Abstr. 120: 217262t) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

Additional suitable conjugated molecules include ribonuclease (RNase), DNase, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intra-molecularly or inter-molecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity. Suitable conjugated molecules may further include any protein that binds to DNA provided that it does not create or stabilize biofilm architecture and/or facilitate bacterial infection; it is envisioned that at least a subset of such proteins may facilitate the kinetics of binding for the interfering agents disclosed herein.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. (1994) Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, Engineering and Clinical Application, Ritter et al. (eds.), pages 60-84 (Cambridge University Press 1995)).

Techniques for conjugating therapeutic agents to antibodies are well known (Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al, (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), pp. 303-16 (Academic Press 1985), and Thorpe et al. (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or non-covalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

Polynucleotides

This disclosure also provides isolated or recombinant polynucleotides encoding one or more of the above-identified isolated or recombinant polypeptides and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides disclosed herein encode polypeptides or proteins having diagnostic and therapeutic utilities as described herein as well as probes to identify transcripts of the protein that may or may not be present. These nucleic acid fragments can be prepared, for example, by restriction enzyme digestion of larger polynucleotides and then labeled with a detectable marker. Alternatively, random fragments can be generated using nick translation of the molecule. For methodology for the preparation and labeling of such fragments, see Green and Sambrook (2012) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See Green and Sambrook (2012) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Green and Sambrook (2012) supra, for methodology. Thus, this disclosure also provides a host cell, e.g., a mammalian cell, an animal cell (rat or mouse), a human cell, or a prokaryotic cell such as a bacterial cell, containing a polynucleotide encoding a protein or polypeptide or antibody.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

When the vectors are used for gene therapy in vivo or ex vivo, a pharmaceutically acceptable vector, such as a replication-incompetent retroviral or adenoviral vector, are exemplary (but non-limiting) and may be of particular use. Pharmaceutically acceptable vectors containing the nucleic acids disclosed herein can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) Bio-Techniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides disclosed herein. The genetically modified cells can be produced by insertion of upstream regulatory sequences such as promoters or gene activators (see, U.S. Pat. No. 5,733,761).

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide disclosed herein under conditions permitting hybridization (optionally moderately stringent hybridization conditions) of complementary single-stranded polynucleotides, or optionally, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Green and Sambrook (2012) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides disclosed herein can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (199.4)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides disclosed herein by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the poly-nucleotide into a suitable replication vector and insert the vector into a suitable host cell (pro-karyotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Green and Sambrook (2012) supra. For instance, mRNA can be isolated using various lytic enzymes or chemical solutions according to the procedures set forth in Green and Sambrook (2012) supra, or extracted by nucleic-acid-binding resins following the accompanying instructions provided by manufactures.

Polynucleotides exhibiting sequence complementarity or homology to a polynucleotide disclosed herein are useful as hybridization probes or as an equivalent of the specific polynucleotides identified herein. Since the full coding sequence of the transcript is known, any portion of this sequence or homologous sequences, can be used in the methods disclosed herein.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. In some embodiments, a probe useful for detecting the aforementioned mRNA is at least about 80% identical to the homologous region. In some embodiments, the probe is 85% identical to the corresponding gene sequence after alignment of the homologous region; in some embodiments, it exhibits 90% identity.

These probes can be used in radioassays (e.g., Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide disclosed herein. Accordingly, this disclosure also provides a probe comprising or corresponding to a polynucleotide disclosed herein, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally well suited, so as to increase stability and selectivity of the hybrid, and thereby improving the specificity of particular hybrid molecules obtained. In certain embodiments, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods. In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Further isolated polynucleotides contemplated herein include an aptamer that is a biological equivalent to an isolated polypeptide, antibody, or small molecule disclosed herein. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293).

Small Molecules

Certain embodiments relate to a small molecule that is a biological equivalent of an isolated polypeptide, isolated polynucleotide, or antibody disclosed herein for use as a therapeutic agent. For the purpose of this disclosure, "small molecules" are molecules having low molecular weights (MW) that are, in one embodiment, capable of binding to a protein of interest thereby altering the function of the protein. In some embodiments, the MW of a small molecule is no more than 1,000. Methods for screening small molecules capable of altering protein function are known in the art. For example, a miniaturized arrayed assay for detecting small molecule-protein interactions in cells is discussed by You et al. (1997) Chem. Biol. 4:961-968.

Compositions

Compositions are further provided. The compositions comprise a carrier and one or more of an isolated polypeptide disclosed herein, an isolated polynucleotide disclosed herein, a vector disclosed herein, an isolated host cell disclosed herein, a small molecule or an antibody disclosed herein. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide disclosed herein, an isolated polynucleotide disclosed herein, a vector disclosed herein, a small molecule, an isolated host cell disclosed herein, or an antibody of the disclosure, formulated with one or more pharmaceutically acceptable substances.

For oral preparations, any one or more of an isolated or recombinant polypeptide as described herein, an isolated or recombinant polynucleotide as described herein, a vector as described herein, an isolated host cell as described herein, a small molecule or an antibody as described herein can be used alone or in pharmaceutical formulations disclosed herein comprising, or consisting essentially of, the compound in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated polypeptide disclosed herein, an isolated polynucleotide disclosed herein, a vector disclosed herein, an isolated host cell disclosed herein, or an antibody disclosed herein can be formulated into preparations for injection in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is an antimicrobial agent such as other vaccine components such as surface antigens, e.g., important virulence factors such as the gingipains (RgpA, RgbB, and Kgp), the RagB lipoprotein, fimbral genes such as FimA and Mfa, outer membrane vesicles (OMV), and the conserved C-terminal domain essential for translocation across the membrane (see Kong et al (2015) *Porphyromonas gingivalis* B cell Antigen Epitope Vaccine, pIRES-ragB'-mGITRL, Promoted RagB-Specific Antibody Production and Tfh Cells Expansion. *Scandinavian Journal of Immunology*, 81(6), 476-482 and Zheng et al (2013) Enhancing specific-antibody production to the ragB vaccine with GITRL that expand Tfh, IFN-γ(+) T cells and attenuates *Porphyromonas gingivalis* infection in mice. *PloS One,* 8(4), e59604, and Bai et al (2015) Immunoreactive antigens recognized in serum samples from mice intranasally immunized with *Porphyromonas gingivalis* outer membrane vesicles. *Pathogens and Disease,* 73(3), ftu006-ftu006 and Kadowski et al (1998) Arg-gingipain Acts as a Major Processing Enzyme for Various Cell Surface Proteins in *Porphyromonas gingivalis. The Journal of Biological Chemistry,* 273(44), 29072-29076 and Chen et al (2004) Comparative whole-genome analysis of virulent and avirulent strains of *Porphyromonas gingivalis. Journal of Bacteriology,* 186(16), 5473-5479 and antimicrobial agents. For intravenous administration, suitable carriers include physiological bacteriostatic water, a formulation vehicle sold under CREMOPHOR EL® (BASF, Parsippany, N.J.), or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations disclosed herein comprise a compound disclosed herein formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself (e.g., by an elastic bladder)).

Suppositories disclosed herein can be prepared by mixing a compound disclosed herein with any of a variety of bases such as emulsifying bases or water-soluble bases. Embodiments of this pharmaceutical formulation of a compound disclosed herein can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds disclosed herein. Similarly, unit dosage forms for injection or intravenous administration may comprise a compound disclosed herein in a composition as a solution in sterile water, normal saline or another pharmaceutically acceptable carrier.

Embodiments of the pharmaceutical formulations disclosed herein include those in which one or more of an isolated polypeptide disclosed herein, an isolated polynucleotide disclosed herein, a vector disclosed herein, a small molecule for use in the disclosure, an isolated host cell disclosed herein, or an antibody disclosed herein is formulated in an injectable composition. Injectable pharmaceutical formulations disclosed herein are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations disclosed herein.

In an embodiment, one or more of an isolated polypeptide disclosed herein, an isolated polynucleotide disclosed herein, a vector disclosed herein, an isolated host cell disclosed herein, or an antibody disclosed herein is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound disclosed herein can be accomplished using any of a variety of refillable, pump systems. Pumps provide consistent, controlled release over time. In some embodiments, a compound disclosed herein is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems may be utilized due to their generally more consistent, controlled release over time. Osmotic pumps are used in some embodiments due to their combined advantages of more consistent controlled release and relatively small size (see, e.g., PCT International Application Publication No.

WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a compound disclosed herein are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylatanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the interfering agent (as well as combination compositions) is delivered in a controlled release system. For example, a compound disclosed herein may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990) Science 249:1527-1533.

In another embodiment, the compositions of the present disclosure (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The present disclosure provides methods and compositions for the administration of a one or more of an interfering agent to a host (e.g., a human) for the treatment of a microbial infection alone or combination with an antimicrobial to the underlying HU generating microorganism or others, such as those that are opportunistic. In various embodiments, these methods disclosed herein span almost any available method and route suitable for drug delivery, including in vivo and ex vivo methods, as well as systemic and localized routes of administration.

Among suitable mechanisms for delivery of the interfering agent, this disclosure provides a microsphere that comprises or alternatively consists essentially of, or yet further consists of, an interfering agent encapsulated within a polymer having a glyosidic bond, e.g. a glycosidic polymer-based microsphere. In one aspect, any glycosidic polymer having an alpha-1,6 linkage, an alpha-1,3 linkage, or any combinations thereof can be used in the microsphere. In one aspect, the glycosidic polymer-based microsphere comprises an insoluble cross-linked dextran, e.g., the commercially available insoluble cross-linked dextran sold under SEPHADEX® (GE Healthcare, Pistcataway, N.J.) or a mimetic thereof or combination thereof.

Disclosed herein are microspheres comprising an antimicrobial agent encapsulated within a glycosidic polymer-based microsphere. In one aspect, the microsphere is comprised of a glycosidic polymer-based microsphere, such as an insoluble cross-linked dextran. A non-limiting example of such includes commercially available insoluble cross-linked dextran marketed under the tradename SEPHADEX® or a mimetics thereof. SEPHADEX® (SEparation PHArmacia DEXtran, cross-linked dextran of varying sizes) is a macroscopic bead of cross-linked dextran (one type of glucan). Varieties of SEPHADEX® are commercially available and differ by their size (fine, medium, course, super fine (G01, G-15, G025 superfine, G-25 fine and G-25 medium) and degree of cross-linking, providing an extensive fractionation range. G-10 has a fractionation range of less than or equal to 700; G-15 has a fractionation range of less or equal to than 1500; G-15 has a fractionation range of less than or equal to 1500; G-25 has a fractionation range of about 1,000 to about 5,000; G-15 has a fractionation range of less than or equal to 1500; G-25 has a fractionation range of less than or equal to 1500; G-50 has a fractionation range of about 1500 to about 30,000; less than or equal to 1500; G-75 has a fractionation range of about 3,000 to about 80,000; G-100 has a fractionation range of about 4,000 to about 150,000; G-150 has a fractionation range of about 5000 to about 300,000; and G-200 has a fractionation range of about 5,000 to about 600,000.

As used herein, the term SEPHADEX® mimetic intends any structure, for example a polymer structure, that resembles SEPHADEX® e.g. a dextranomer or other polysaccharide consisting of glucose made into microspheres.

The average diameter of the microsphere can vary, for example having less than about 1000 μm in diameter (wet bead size). In some embodiments, the particles range in size from about 1 μm μm to about 1,000 μm in diameter, or alternatively between about 10 μm to about 500 μm, or alternatively between about 10 μm to about 500 μm, or alternatively between about 10 μm to about 800 μm, or alternatively between about 10 μm to about 700 μm, or alternatively between about 10 μm to about 600 μm, or alternatively between about 20 μm to about 1000, or alternatively between about 20 μm to about 800 μm, or alternatively between about 20 μm to about 700 μm, or alternatively between about 20 μm to about 600 μm, or alternatively between about 20 μm to about 500 μm; or alternatively between about 30 μm to about 1000 μm, or alternatively between about 30 μm to about 900 μm, or alternatively between about 30 μm to about 800 μm, or alternatively between about 30 μm to about 700 μm, or alternatively between about 100 μm to about 900 μm, or alternatively between about 200 μm to about 1000 μm, or alternatively between about 40 μm to about 1000 μm, or alternatively between about 40 μm to about 500 μm, or alternatively between about 40 μm to about 400 μm; or alternatively between about 40 μm to about 300 μm; or alternatively between about 10 μm to about 300 μm, or alternatively less than about 500 μm, or alternatively less than about 400 μm, or alternatively less than about 300 μm, or alternatively less than about 250 μm, or alternatively less than about 200 μm, alternatively lets than about 150 μm, or alternatively less than about 100 μm, or alternatively less than about 75 μm, or alternatively less than about 50 μm.

In addition to the interfering agent, one or more antimicrobial agents may be comprised within the core of the microsphere. The antimicrobial agent is any agent that has activity against the target organism, non-limiting examples of such include hydrogen peroxide, chlorhexidine, penicillin, streptomycin, erythromycin, xylitol, fluoride, triclosan, alcohol, and cetylpyridinium chloride. The amount of the encapsulated agent will vary, e.g., from about 10 μl to about 250 or from about 10 μl to about 200 or from about 10 μl to about 150 or from about 50 μl to about 250 or from about 50 μl to about 150 or from about 50 μl to about 250 or from about 75 μl to about 250 μl.

Also provided herein is a composition comprising, or alternatively consisting essentially of, or yet further consisting of, a plurality of microspheres as described above. The microspheres in the composition can comprise microspheres having the same or different average diameter, and/or the same or different composition of microsphere, and/or the same or different antimicrobial agent.

The compositions can further comprise one or more of any of the standard carriers, such as a phosphate buffered saline solution, buffers, water, and emulsions, such as an oil/water or water/oil emulsion, and various types of wetting agents. The carrier also can include stabilizers, preservatives, a pharmaceutically acceptable flavoring agent, and a coloring agent. The microspheres and compositions containing them can be formulated as a solid, a semi-solid or a liquid, e.g., a chewable tablet, a dissolvable lozenge, a suspension, a gum, a gel, a toothpaste, a fluoride rinse, or a mouthwash.

Any suitable interfering agent or, more generally, antimicrobial can be encapsulated within the microsphere, non-limiting examples of such include without limitation those that are active against organisms that cause dental caries and associated disease, e.g., one or more from the group of hydrogen peroxide, chlorhexidine, penicillin, streptomycin, erythromycin, xylitol, fluoride, triclosan, alcohol, and cetylpyridinium chloride.

The microspheres can be combined with a carrier, e.g., a pharmaceutically acceptable carrier. The composition can be formulated as a solid, a semi-solid or a liquid and can optionally comprise, or alternatively consisting essentially of, or yet further consist of, one or more of a flavoring agent or a color agent. The compositions can be formulated as a lyophilized powder, a chewable tablet, a suspension, a dissolvable lozenge, a gum, a gel, a fluoride rinse, a mouthwash.

Also provided herein are methods for making the microspheres by combining an effective amount of the microsphere particle and the interfering agent and any additional agent (e.g., antimicrobial), e.g., PLGA is mixed to hydration or wetting in an amount of hydrogen peroxide to produce a slurry. Excess agent is removed by any appropriate method, e.g., centrifugation, desiccation, and filtration, leaving the antimicrobial in the lumen of the microsphere.

The microspheres can be combined with an appropriate carrier and formulated using methods known in the art. Additional agents such as buffers, stabilizers, preservatives, a pharmaceutically acceptable flavoring agent, or a coloring agent can be added. The microspheres and compositions containing them can be formulated as a solid, a semi-solid or a liquid, e.g., a chewable tablet, a suspension, a dissolvable lozenge, a gum, a gel, a toothpaste, a fluoride rinse, or a mouthwash.

Formulations and Co-Formulations

More specifically, the disclosure provided herein provides specific formulations and co-formulations of the interfering agents disclosed along with a pharmaceutically acceptable excipient, such as those disclosed herein above.

For the purpose of the above noted formulations and co-formulations, the interfering agent is of the group of:
(a) an isolated or recombinant HU polypeptide or fragment or equivalent each thereof, e.g., an antigenic polypeptide or protein;
(b) an isolated or recombinant polynucleotide that encodes the polypeptide of (a) or its compliment or a fragment or equivalent each thereof;
(c) an antibody or antigen binding fragment that specifically recognizes or binds (a) or a fragment or equivalent each thereof; and/or
(d) an isolated or recombinant polynucleotide that encodes the antibody or antigen binding fragment of (c) or a fragment or equivalent each thereof.

In some embodiments, the antibodies are present in the formulation at a concentration from about 0.1 mg/mL to about 200 mg/mL, or alternatively from about 1 to about 150 mg/mL, or alternatively about 2 mg/mL to about 100 mg/mL, or alternatively about 3 mg/mL to about 80 mg/mL, or alternatively about 4 mg/mL to about 50 mg/mL, or alternatively about 5 mg/mL to about 20 mg/mL. In some embodiments, the antibodies are present at a concentration of at least about 1 mg/mL, or alternatively at least about 2 mg/mL, at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL or alternatively at least about 200 mg/mL. In some embodiments, at least one of the plurality of antibodies is present at a concentration of at least about 1 mg/mL, or alternatively at least about 2 mg/mL, or alternatively at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL, or alternatively at least about 200 mg/mL.

In some embodiments, wherein multiple different antibodies are included an antibody co-formulation, the different antibodies may be present in substantially equal concentrations. In another aspect of such embodiments, the different antibodies one or more of the antibodies may be present in a substantially higher concentration than the other antibodies, e.g., ratios of about 1.5:1, or alternatively about 1.5:1:1, or alternatively about 1.5:1:1:1, or alternatively about 2:1, or alternatively about 2:1:1, or alternatively about 2:1:1:1, or alternatively at least about 2.5:1, or alternatively at least about 2.5:1:1, or alternatively at least about 2.5:1:1:1.

Methods of stably formulating antibody formulations and co-formulations can be made according to techniques disclosed in the art—see, e.g., U.S. Pat. Publication No. 2011/0059079.

Diagnostic and Therapeutic Methods

Also provided are methods for inhibiting, competing or titrating the binding of an HU protein to a microbial DNA, by contacting the HU protein or the microbial DNA with an interfering agent, thereby inhibiting, competing or titrating the binding of the HU protein to the microbial DNA. In a further aspect, one or more of the HU protein and the microbial DNA are detectably labeled, for example with luminescent molecules that will emit a signal.

In aspects where both the HU protein and the microbial DNA are detectably labeled, for example, with luminescent molecules, in some embodiments, the luminescent molecules may emit a signal when brought into close contact with each other. This contacting can be performed in vitro or in vivo.

When practiced in vitro, the methods are useful to screen for or confirm interfering agents having the same, similar or opposite ability as the polypeptides, polynucleotides, antibodies, host cells, small molecules and compositions disclosed herein. Alternatively, they can be used to identify which interfering agent is best suited to treat a microbial infection. For example, one can screen for new agents or combination therapies by having two samples containing for example, the HU protein and microbial DNA and the agent to be tested. The second sample contains the HU protein and microbial DNA and an agent known to be active, e.g., an anti-HU antibody or a small molecule to serve as a positive control. In a further aspect, several samples are provided and the interfering agents are added to the system in increasing dilutions to determine the optimal dose that would likely be effective in treating a subject in the clinical setting. As is apparent to those of skill in the art, a negative control containing the HU protein and the microbial DNA can be provided. In a further aspect, the HU protein and the microbial DNA are detectably labeled, for example with luminescent molecules that will emit a signal when brought into close contact with each other. The samples are contained under similar conditions for an effective amount of time for the agent to inhibit, compete or titrate the interaction between the DNABII polypeptide and microbial DNA and then the sample is assayed for emission of signal from the luminescent molecules. If the sample emits a signal, then the agent is not effective to inhibit binding.

In another aspect, the in vitro method is practiced in a miniaturized chamber slide system wherein the microbial (such as a bacterial) isolate causing an infection could be isolated from the human/animal then cultured to allow it to grow as a biofilm in vitro, see for example Experiment 1 below. The interfering agent (such as anti-HU antibody) or potential interfering agent biofilm is added alone or in combination with another agent to the culture with or without increasing dilutions of the potential interfering agent or interfering agent such as an anti-HU (or small molecule, agent, etc.) to find the optimal dose that would likely be effective at treating that patient when delivered to the subject where the infection existed. As apparent to those of skill in the art, a positive and negative control can be performed simultaneously.

In a further aspect, the method is practiced in a high throughput platform with the interfering agent (such as anti-HU antibody) and/or potential interfering agent (alone or in combination with another agent) in a flow cell. The interfering agent (such as anti-IHF antibody) or potential interfering agent biofilm is added alone or in combination with another agent to the culture with or without increasing dilutions of the potential interfering agent or interfering agent such as an anti-HU (or other antibody, small molecule, agent, etc.) to find the optimal dose that would likely be effective at treating that patient when delivered to the subject where the infection existed. Biofilm isolates are sonicated to separate biofilm bacteria from the HU protein bound to microbial DNA. The HU protein—DNA complexes are isolated by virtue of the anti-IHF antibody on the platform. The microbial DNA is then be released with e.g., a salt wash, and used to identify the biofilm bacteria added. The freed DNA is then identified, e.g., by PCR sequenced. If DNA is not freed, then the interfering agent(s) successfully performed or bound the microbial DNA. If DNA is found in the sample, then the agent did not interfere with HU protein-microbial DNA binding. As is apparent to those of skill in the art, a positive and/or negative control can be simultaneously performed.

In some embodiments, the methods disclosed herein can be used as a diagnostic test to determine whether a particular agent is suitable for administration of an interfering agent capable of inhibiting, competing, or titrating the binding of an HU protein to microbial DNA by determining the presence or absence of the HU protein in the target biofilm.

The above methods also can be used as a diagnostic test since it is possible that a given bacterial species will respond better to reversal of its biofilm by one agent more than another, this rapid high throughput assay system could allow one skilled the art to assay a panel of possible anti-HU-like agents to identify the most efficacious of the group.

The advantage of these methods is that most clinical microbiology labs in hospitals are already equipped to perform these sorts of assays (i.e., determination of MIC, MBC values) using bacteria that are growing in liquid culture (or planktonically). As is apparent to those of skill in die art, bacteria generally do not grow planktonically when they are causing diseases. Instead they are growing as a stable biofilm and these biofilms are significantly more resistant to treatment by antibiotics, antibodies or other therapeutics. This resistance is why most MIC/MBC values fail to accurately predict efficacy in vivo. Thus, by determining what "dose" of agent could reverse a bacterial biofilm in vitro (as described above) Applicants' pre-clinical assay would be a more reliable predictor of clinical efficacy, even as an application of personalized medicine.

In addition to the clinical setting, the methods can be used to identify the microbe causing the infection and/or confirm effective interfering agents in an industrial setting. In some aspects, the methods can be used to prevent formation of or to disperse or dissolve a biofilm in an industrial setting or associated with an industrial process by treating a surface or industrial environment (e.g., within a pipe) susceptible to, or containing a biofilm with the agent as disclosed herein.

In a further aspect of the above methods, an antibiotic or antimicrobial known to inhibit growth of the underlying infection is added sequentially or concurrently, to determine if the infection can be inhibited. It is also possible to add the interfering agent to the microbial DNA or HU protein before adding the complex to assay for biofilm inhibition.

In another aspect, provided herein is a method of inhibiting, preventing or breaking down a biofilm in a subject by administering to the subject an effective amount of an interfering agent, thereby inhibiting, preventing or breaking down the microbial biofilm.

Alternatively or additionally, methods of inhibiting, preventing, dissolving, dispersing or breaking down a biofilm may be practiced in vitro and/or ex vivo and involve providing a sample of the biofilm—taken from a subject or generated in vitro—and administering an effective amount of an interfering agent, thereby inhibiting, preventing or breaking down the microbial biofilm. Similarly, the compositions disclosed herein may be used in method embodiments for inhibiting, preventing, dissolving, dispersing, or breaking down microbial biofilms on surfaces colonized by biofilms such as, but not limited to, hospital instruments, industrial equipment, and other materials not comprised of living tissue.

For the purpose of the above noted in vitro and in vivo methods, the interfering agent is of the group of:
(a) an isolated or recombinant HU polypeptide or fragment or equivalent each thereof, e.g., an antigenic polypeptide or protein;
(b) an isolated or recombinant polynucleotide that encodes the polypeptide of (a) or its compliment or a fragment or equivalent each thereof;
(c) an antibody or antigen binding fragment of the antibody or an antigen binding polypeptide that specifically recognizes or binds (a) or a fragment or equivalent each thereof; and/or
(d) an isolated or recombinant polynucleotide that encodes the antibody or antigen binding fragment of (c) or a fragment or equivalent each thereof.

In some method aspects, the interfering agent competes, titrates, or inhibits the binding of an HU protein but does not compete, titrate, or inhibit the binding of an IHF protein. In some aspects, the interfering agent may be specific and competes, titrates, or inhibits the binding of an HU protein of a specific microbial species but does not inhibit HU proteins of other microbial species. In some aspects, the interfering agent may be cross reactive and competes, titrates, or inhibits binding of an HU protein of multiple species.

Also provided herein is a method for inducing an immune response in or conferring passive immunity on subject in need thereof, comprising, or alternatively consisting essentially of, or yet further consisting of, administering to the subject an effective amount of one or more of the group:
(a) an isolated or recombinant HU polypeptide or fragment or equivalent each thereof e.g., an antigenic polypeptide or protein;
(b) an isolated or recombinant polynucleotide that encodes the polypeptide of (a) or its compliment or a fragment or equivalent each thereof;
(c) an antibody or antigen binding fragment if the antibody or an antigen binding polypeptide that specifically recognizes or binds (a) or a fragment or equivalent each thereof; and/or
(d) an isolated or recombinant polynucleotide that encodes the antibody or antigen binding fragment of (c) or a fragment or equivalent each thereof.

In a further aspect, the methods further comprise, or alternatively consist essentially of, or yet further consist of administering to the subject an effective amount of one or more of an antimicrobial, an antigenic peptide or an adjuvant.

In a further aspect, the compositions and methods disclosed herein are useful to treat a subject in need thereof, wherein the subject is suffering from a condition or disease selected from the group of: on oral infection, an infected artificial device, joint, catheter, stent or other surgical implant, a lung infection, pneumonia, cystic fibrosis, otitis media, native valve infectious endocarditis, osteomyelitis, rhinosinusitis, prostatitis, urinary tract infection, a dermal wound, lyme disease, dental caries and periodontitis. An effective amount of the interfering agent is delivered locally or systemically to the subject. Effective amounts can be empirically determined. As used herein, non-limiting examples of subjects include an animal, a mammal, an ovine, a bovine, a simian, an equine, a canine, a feline or a human patient.

A non-limiting example of an antimicrobial agent is another vaccine component such as a surface antigen, as disclosed above.

The agents and compositions disclosed herein can be concurrently or sequentially administered with other antimicrobial agents and/or surface antigens. In one particular aspect, administration is locally to the site of the infection by direct injection or by inhalation for example. Other non-limiting examples of administration include by one or more method comprising transdermally, urethrally, sublingually, rectally, vaginally, ocularly, subcutaneous, intramuscularly, intraperitoneally, intranasally, by inhalation or orally.

Thus, routes of administration applicable to the methods disclosed herein include intranasal, intramuscular, urethrally, intratracheal, subcutaneous, intradermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The interfering agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

Some therapeutic embodiments that require delivery to the oral cavity may be facilitated using microspheres as noted above. Thus, also provided are methods for selectively inhibiting the growth of, and/or selectively removing biofilm related disease organisms from the oral cavity, by administering to the oral cavity of the subject an effective amount of the interfering agent delivered in a microsphere or composition containing the same.

Also provided herein is a composition comprising, or alternatively consisting essentially of, or yet further consisting of, a plurality of microspheres as described above. The microspheres in the composition can comprise microspheres having the same or different average diameter, and/or the same or different composition of microsphere, and/or the same or different antimicrobial agent.

In one aspect, the microsphere, compositions and/or formulations are administered at least about 5 minutes, or alternatively at least about 7 minutes, or alternatively at least about 8 minutes, or at least about 10 minutes, or at least about 12 minutes, or alternatively at least about 15 minutes, or alternatively at least about 20 minutes, after the ingestion of or the presence of a food such as a high sugar food, by the subject. Mode of administration will vary with the formulation and can include dissolving a lozenge or alternatively swishing for an effective amount of time a mouthwash containing the microsphere.

The selection of the microsphere, the antimicrobial and formulation will vary with the subject being treated and the target of the therapy. These are determined by a treating or recommending physician or dentist.

The amount of microsphere to be administered to the subject will vary with the subject. Non-limiting examples of such include of about 5 to about 250 mg of microsphere per dose, or alternatively from about 15 to about 250 mg; or alternatively from about 25 to 100 mg; or alternatively from about 25 to about 75 mg; or about 25 to about 50 mg, or microsphere per dose.

In various embodiments of the methods disclosed herein, the interfering agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200-about 500 mg, and sometimes, depending on the compound, up to as much as about 1 g to about 2.5 g.

Dosing of can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Functional Analysis with Antibodies

Antibodies disclosed herein can be used to purify the polypeptides disclosed herein and to identify biological equivalent polypeptide and/or polynucleotides. They also can be used to identify agents that modify the function of the polypeptides disclosed herein. These antibodies include polyclonal antisera, monoclonal antibodies, and various reagents derived from these preparations that are familiar to those practiced in the art and described above.

Antibodies that neutralize the activities of proteins encoded by identified genes can also be used in vivo and in vitro to demonstrate function by adding such neutralizing antibodies into in vivo and in vitro test systems. They also are useful as pharmaceutical agents to modulate the activity of polypeptides disclosed herein.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

Further, in some embodiments, the antibodies disclosed herein may be used to visualize and/or detect biofilms. In such embodiments, the antibodies may be detectably labeled, e.g., with a radioisotope, an enzyme which generates a detectable product, a fluorescent protein, and the like or conjugated to other moieties, such as members of specific binding pairs, e.g., biotin (member of biotin-avidin specific binding pair), and the like. Detectably labeled antibodies may then be introduced to the sample suspected of being colonized by a biofilm and visualized and/or detected through microscopy or other methods known to detect the relevant label, e.g., spectroscopy, cytometry, or other common techniques. Conjugated antibodies or unlabeled antibodies may likewise be identified through known analytical methods targeting the conjugated moiety or antibody, respectively. For example, in some embodiments, a detectably labeled secondary antibody specific to the isotype of the antibodies disclosed herein may be used in the visualization and/or detection of a biofilm; such embodiments may entail the administration of the antibody specific to the exposed portion of an HU protein to the surface suspected of being colonized by a biofilm, followed by the administration of the detectably labeled secondary antibody and the subsequent detection of the relevant label.

This disclosure provides methods and compositions to inhibit or prevent infection of a host cell by a bacteria that exports an HU protein, the methods and compositions comprising, or alternatively consisting essentially of, or yet further consisting of, administering to a tissue exposed to or infected with the bacteria an effective amount of an bacteria-relevant antibody that specifically recognizes and binds the HU protein, thereby inhibiting or preventing infection of the host cell by the bacteria. The antibody can be polyclonal, monoclonal or a derivative of an antibody that recognizes and binds the bacteria-relevant HU protein. Multiple antibodies can be administered concurrently or sequentially along with supporting therapies as noted herein. Owing to the omnipresence of these DNABII proteins associated with the bacterial surface throughout the life cycle of the cell inclusive of all states, e.g. individual, aggregated or resident biofilm bacteria, antisera directed to HU proteins may interfere with interactions with the host cell surface including, attachment and subsequent invasion. Bacteria that can invade and propagate in host cells are protected from the host's immune system and antimicrobial therapy. Rendering bacteria incapable of binding and invasion makes them susceptible to clearance by the immune system and administered antimicrobials. The source of antibody against the HU protein can be elicited by either active vaccination of the host with HU protein or passive transfer of antiserum or an antibody against the HU protein.

This disclosure provides a method to inhibit or prevent infection of a cell by a bacteria that exports an HU protein. The method comprises, or alternatively consists essentially of, or yet further consists of, administering to a tissue infected with the bacteria an effective amount of an antibody that specifically recognizes and binds the HU protein, thereby inhibiting or preventing infection of the bacteria. The source of antibody against the HU family proteins can be elicited by either active vaccination of the host with the HU protein or passive transfer of antiserum or an antibody against proteins of the HU protein. The antibody can be polyclonal, monoclonal or a derivative of an antibody that recognizes and binds the bacteria-relevant HU protein. Multiple antibodies can be administered concurrently or sequentially along with supporting therapies as noted herein.

The administration can be in vitro in a culture or in vivo, by administration to a patient infected with the bacteria. When practiced in vivo, the method can be used to treat a subject infected with the bacteria by administering to the infected subject an effective amount of the antibody. In addition, when the subject is a non-human animal, the method can be used to test possible therapies or combination therapies prior to administration to a human. When practiced in vitro, the method is useful to screen for other therapeutic agents and combination therapies, such as small molecule drugs, that inhibit or prevent infection of the bacteria in a tissue.

Also provided are methods to treat a bacterial infection in subject in need thereof, wherein the subject is infected with a bacteria that comprises an HU protein, the method comprising, or alternatively consisting essentially of, or yet further consisting of, administering to the subject an effective amount of an antibody that specifically recognizes and binds the HU protein, thereby inhibiting or preventing infection of the bacteria. The antibody can be polyclonal, monoclonal or a derivative of an antibody that recognizes and binds the bacteria-relevant HU protein. The source of antibody against the HU protein can be elicited by either active vaccination of the host with the HU protein or passive transfer of antiserum or an antibody against proteins of the HU protein. Multiple antibodies can be administered concurrently or sequentially along with supporting therapies as noted herein.

Yet further provided are methods to treat a condition in a subject in need thereof, wherein the condition is associated with a bacterial infection wherein the bacteria comprises an HU protein, the method comprising, or alternatively consisting essentially of, or yet further consisting of, administering to the subject an effective amount of an antibody that specifically recognizes and binds the HU protein, thereby inhibiting or preventing infection of the bacteria. The source of antibody against the HU protein can be elicited by either active vaccination of the host with the HU protein or passive transfer of antiserum or an antibody against the HU protein. The antibody can be polyclonal, monoclonal or a derivative of an antibody that recognizes and binds the bacteria-relevant HU protein. Multiple antibodies can be administered concurrently or sequentially along with supporting therapies as noted herein.

The antibodies disclosed herein may be used for vaccination or to boost vaccination, alone or in combination with peptides or protein-based vaccines or dendritic-cell based vaccines.

Screening Assays

The present disclosure provides methods for screening for equivalent agents, such as equivalent monoclonal antibodies and fragments thereof to exemplified antibodies as described herein and various agents that modulate the activity of the active agents and pharmaceutical compositions disclosed herein or the function of a polypeptide or peptide product encoded by the polynucleotide disclosed herein. For the purposes of this disclosure, an "agent" is intended to include, but not be limited to a biological or chemical compound such as a simple or complex organic or inorganic molecule, a peptide, a protein (e.g., antibody), a polynucleotide anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

To practice the screening method in vitro, suitable cell culture or tissue infected with the microbial to be treated are first provided. The cells are cultured under conditions (temperature, growth or culture medium and gas ($CO_2$) and for an appropriate amount of time to attain exponential proliferation without density dependent constraints. It also is desirable to maintain an additional separate cell culture that is not infected as a control.

As is apparent to one of skill in the art, suitable cells can be cultured in micro-titer plates and several agents can be assayed at the same time by noting genotypic changes, phenotypic changes or a reduction in microbial titer.

When the agent is a composition other than a DNA or RNA, such as a small molecule as described above, the agent can be directly added to the cell culture or added to culture medium for addition. As is apparent to those skilled in the art, an "effective" a mount must be added which can be empirically determined.

When the agent is an antibody or antigen binding fragment, the agent can be contacted or incubated with the target antigen and polyclonal antibody as described herein under conditions to perform a competitive ELISA. Such methods are known to the skilled artisan.

The assays also can be performed in a subject. When the subject is an animal such as a rat, chinchilla, mouse or simian, the method provides a convenient animal model system that can be used prior to clinical testing of an agent in a human patient. In this system, a candidate agent is a potential drug if symptoms of the disease or microbial infection is reduced or eliminated, each as compared to untreated, animal having the same infection. It also can be useful to have a separate negative control group of cells or animals that are healthy and not treated, which provides a basis for comparison.

The agents and compositions can be used in the manufacture of medicaments and for the treatment of humans and other animals by administration in accordance with conventional procedures, such as an active ingredient in pharmaceutical compositions.

A screen to identify potential therapeutic agents that inhibit or prevent infection of a cell by a bacteria that exports an HU protein and/or that disrupt or prevent biofilm formation is also disclosed. The screening method comprises, or alternatively consists essentially of, or yet consists of, contacting in vitro or administering in vivo to a tissue infected with the bacteria an agent and determining if the agent binds the HU protein. Methods to determining binding are known in the art and several non-limiting examples are described herein. In one aspect, if the agent binds the protein, the agent is a potential therapeutic agent and if the agent does not bind the protein, the agent is not a potential therapeutic agent. In another aspect, if the infection or biofilm is inhibited, disrupted, or prevented in vivo, the agent is a potential therapeutic agent and if infection is not inhibited or prevented, the agent is not a potential therapeutic agent. Methods of determining if the infection is inhibited or prevented are known in the art and several non-limiting examples are described herein; methods of determining if a biofilm is disrupted or prevented are known in the art and further disclosed herein. Non-limiting examples of potential therapeutic agents are from the group of: an antibody, an antibody derivative, a polypeptide or a small molecule. Multiple antibodies can be administered concurrently or sequentially along with supporting therapies as noted herein. In a further aspect, the agent binds the protein and the binding is compared to the binding of anti-HU antisera to the protein, e.g., antisera directed against an HU protein.

Combination Therapy

The compositions and related methods of the present disclosure may be used in combination with the administration of other therapies. These include, but are not limited to, the administration of DNase enzymes, antibiotics, antimicrobials, or other antibodies.

In some embodiments, the methods and compositions include a deoxyribonuclease (DNase) enzyme that acts synergistically with the anti-DNABII antibody. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective Unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. Non-limiting examples of an antibodies that could be useful in combination with the methods and compositions described herein are antibodies directed against unrelated outer membrane proteins (i.e., RagB, Kgp, RgpA). Vaccination experiments utilizing these antigens alone do have shown limited success in relieving periodontitis (see Guo et at (2014) J. Periodontol. 85(11):1575-1581, Kong et al (2015) Scandinavian Journal of Immunology, 81(6), 476-482 Zheng et al (2013) PloS One, 8(4), e59604. Combined therapy antibodies derived against these proteins and a biofilm reducing agent should result in a greater effect than that which could be achieved by either reagent used alone at the same concentration. Other antibodies that may produce a synergistic effect when combined with a biofilm reducing agent or methods to reduce a biofilm include anti-FimA anti-RagB, anti-Kgp, anti-RgpA, anti-RgpB and anti-OMV preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formation or as a separate formulation.

Kits

Kits containing the agents and instructions necessary to perform the in vitro and in vivo methods as described herein also are claimed. Accordingly, the disclosure provides kits for performing these methods which may include an interfering disclosed herein as well as instructions for carrying out the methods disclosed herein such as collecting tissue and/or performing the screen, and/or analyzing the results, and/or administration of an effective amount of an interfering agent as defined herein. These can be used alone or in combination with other suitable antimicrobial agents.

For example, a kit can comprise, or alternatively consist essentially of, or yet further consist of any one or more interfering agent such as, but not limited to:

(a) an isolated or recombinant HU polypeptide or fragment or equivalent each thereof, e.g., an antigenic polypeptide or protein;

(b) an isolated or recombinant polynucleotide that encodes the polypeptide of (a) or its compliment or a fragment or equivalent each thereof;

(c) an antibody or antigen binding fragment of the antibody or an antigen binding polypeptide that specifically recognizes or binds (a) or a fragment or equivalent each thereof; and/or (d) an isolated or recombinant polynucleotide that encodes the antibody or antigen binding fragment of (c) or a fragment or equivalent each thereof.

The following examples are intended to illustrate, and not limit the embodiments disclosed herein.

EXAMPLES

Example 1: HU Deficient Non-Typeable Hameophilus influenzae (NTHI)

An HU deficient NTHI strain (NTHI ΔHU) was constructed and demonstrated that the lack of HU, despite having no effect on the growth rate of NTHI, significantly decreased the rate of biofilm formation. The architecture of the biofilm and the distribution of eDNA within the biofilm were significantly different compared to wild type (WT) and the biofilm was resistant to disruption by an antiserum derived against a DNABII family member (anti-IHFEc) that is otherwise effective against WT NTHI. To further characterize the differences in the architecture of the biofilm, we used Atomic Force Microscopy (AFM) to determine the detach force of the in vitro preformed biofilm.

The lack of expression of HU resulted in a lower range of detach force (0.05-0.59 nN) compared to WT wild type (0.1-2 nN) which that suggested the formation of a less cohesive biofilm in the absence of HU. These data demonstrated that HU plays a critical role in maintaining specific aspects of the architecture of an NTHI biofilm.

Example 2: Comparative Analysis of Anti-HU Serum

Bacterial strains and growth conditions: P. gingivalis strain 381 strains were maintained on trypicase soy broth agar plates supplemented with 5% defibrinated sheep blood, hemin (5 μg/ml), menadione (1 μg/ml), and 1.5% agar under anaerobic conditions (5% hydrogen 10% carbon dioxide, 85% nitrogen) at 37° C. The P. gingivalis ΔHUβ strain was made as described previously (31) and selection maintained with added erythromycin at 5 μg/ml. Broth cultures of P. gingivalis were grown in Todd Hewitt Broth (THB) supplemented with hemin (5 μg/ml), menadione (1 μg/ml) (THBHK) under anaerobic conditions at 37° C. S. gordonii strain Chalis CH1 (DL1) was maintained on THB agar plates with 1.5% agar at 37° C., 5% $CO_2$. Broth cultures of S. gordonii were grown in THB at 37° C., 5% $CO_2$.

Purification of DNABII proteins: Integration host factor (IHF) and HU from E. coli were purified as previously described (29). S. gordonii HU was purified as follows. A S. gordonii liquid culture was diluted 1 to 100 into 1.5 L of chemically defined medium (CDM) (32) and grown statically for 16 hrs. at 37° C., 5% $CO_2$. Cells were pelleted at 7000 g for 10 min. and resuspended in 10 mM potassium phosphate pH 7.0, 200 mM KCl, 1 mM PMSF, 100 μg/ml DNase I. Cell suspension was lysed by two passages through a French pressure cell at 20000 psi. Cell lysates were clarified by centrifugation at 39000 g for 35 min. followed by filtration through a 0.45 μm filter. Clarified lysates were bound to a 1 ml heparin SEPHAROSE® column (utilizing an ion exchange media sold under SEPHAROSE®) equilibrated with 10 mM potassium phosphate, pH 7.0, 200 mM KCl. The protein was then eluted with a 20 column volume linear gradient from 200 to 2 M KCl. Fractions were analyzed by SDS-PAGE analysis and fractions containing purified S. gordonii HU were combined and dialyzed overnight against 2 L of 50 mM Tris pH 7.4, 600 mM KCl, 1 mM EDTA, 10% glycerol, drop frozen over liquid nitrogen and stored at −80° C. P. gingivalis HUα and HUβ proteins were purified using the Intein Mediated Purification with an Affinity Chitin-binding Tag (IMPACT®) kit (NEB) following manufacturer's protocols. Briefly, the HUα and HUβ genes from P. gingivalis were PCR amplified and cloned into the NdeI and SapI sites of plasmid pTXB1 creating C-terminal fusions with the chitin binding protein. The resulting plasmids were then transformed into E. coli strain ER2566 and the resulting transformants were selected on lysogeny broth (LB) (33, 34) agar plates supplemented with 100 mg/ml ampicillin at 37° C. Single colonies picked and grown overnight in LB broth at 37° C. and the resulting cultures were subcultured 1 to 50 into 1.5 L of LB and grown at 37° C. shaking (200 rpm) until cultures reached an optical density at 600 nm of 0.5 (HUβ) or 0.3 (HUα). Expression of the fusion protein was induced through the addition of 1 mM isopropyl β-D-1-thiogalactopyranoside (IPTG) for 3 hrs. Cells were then harvested at 7000 g for 10 min and resuspended in chitin binding buffer (20 mM Tris-HCl pH 8.5, 500 mM NaCl, 1 mM EDTA). Cell suspensions were lysed by two passages through a French pressure cell at 20000 psi. Cell lysates were clarified by centrifugation at 39000 g for 35 min. followed by filtration through a 0.45 μm filter. Clarified lysates were bound to 5 ml of chitin beads equilibrated in chitin binding buffer and washed with 20 column volumes of chitin binding buffer. On column cleavage of the fusion proteins was performed by washing columns with 3 volumes of chitin binding buffer containing 30 mM DTT and allowing the columns to sit at 4° C. for 70 hrs. before elution of the purified protein. Fractions were analyzed by SDS-PAGE analysis and fractions containing purified P. gingivalis HUα or HUβ were combined and dialyzed against 2 L of 50 mM Tris pH 7.9, 500 mM KCl, 1 mM EDTA, 10% glycerol overnight at 4° C., drop frozen over liquid nitrogen, and stored at −80° C.

In vitro biofilm analysis: S. gordonii was cultured on THB agar overnight at 37° C., 5% $CO_2$. The culture was diluted to an $OD_{490\,nm}$ of 0.65 and subsequently diluted 1:4 in THB and grown statically at 37° C. until an $OD_{490\,nm}$ of 0.65 was reached. The culture was then diluted 1:2500 in CDM with 1% glucose as a carbon source and 200 μl of this culture was used to inoculate each well of an eight-well chambered glass coverslip. Cultures were grown at 37° C., 5% $CO_2$ for 24 hours to allow for biofilm formation. P. gingivalis cultures were grown in THBHK anaerobically at 37° C. for 2 days. The resulting cultures were diluted 1:2 in THBHK, grown for 6 hours, and diluted to an $OD_{490\,nm}$ of 0.1 in THBHK and 200 μl of this culture were used to inoculate each well of an eight-well chambered glass coverslip. Cultures were grown for 40 hrs. anaerobically at 37° C. to allow for biofilm formation. For the addition of exogenous DNABII proteins, protein was added to 0.5 μM to the cultures at the time of biofilm seeding, calf thymus DNA (ctDNA) was added at the indicated concentrations at seeding as well. Antisera derived against DNABII proteins were added at a 1:50 ration at the time of biofilm seeding. After 24 hrs. S. gordonii biofilms were stained with LIVE/DEAD® stain (Molecular Probes, Eugene Oreg.) following manufacturer's protocols, washed once with 200 μl of sterile 0.9% NaCl and fixed with fixative solution (1.6% paraformaldehyde, 0.025% glutaraldehyde, 4% acetic acid, in 0.1 M sodium phosphate buffer pH 7.4). P. gingivalis biofilms were washed twice with sterile 0.9% NaCl, stained with LIVE/DEAD® stain, washed an additional two times and fixed with fixative solution. Biofilms were imaged using a 63× water objective on a Zeiss 510 Meta-laser scanning confocal microscope (carl Zeiss, Thornwood, N.Y.). Three-dimensional z-stack images were reconstructed with AxioVision Rel. 4.8 (Carl Zeiss) and the average biofilm thickness and total biofilm biomass parameters were determined using the COMSTAT analysis program running on MatLab software. All biofilm conditions were completed a in a minimum of 3 independent experiments, with each experiment containing 2 wells for each condition and 4 images taken and averaged from each well.

Immunofluorescence of DNABII proteins within in vitro biofilms:Biofilms were grown and stained as previously described and fixed for one hour before being washed twice with 200 μl of Tris buffered saline pH 7.4 (TBS). Primary antibody was added at a 1 to 150 dilution in TBS and incubated for 1 hour at room temperature. Biofilms were washed two times with 200 μl of TB S and incubated with ECL-Plex Goat-α-Rabbit IgG Cy5 (GE Healthcare Life Sciences) antibody at a 1 to 250 dilution for 30 min. Biofilms were then washed twice with 200 μl TBS and imaged a 63× water objective on a Zeiss 510 Meta-laser scanning confocal microscope (carl Zeiss, Thornwood, N.Y.). Three-dimensional z-stack images were reconstructed with AxioVision Rel. 4.8.

Previous work has indicated that antisera directed against the E. coli IHF protein ($\alpha IHF_{Ec}$) has the ability to recognize DNABII proteins from a wide variety of organisms. Goodman et al. Mucosal immunology. 2011; 4(6):625-37. Indeed, $\alpha IHF_{Ec}$ is able to recognize a variety of DNABII proteins as judged by Western blot analysis (FIG. 1) including DNABII proteins from the oral microbes Streptococcus gordonii and Streptococcus mutans. Similarly, antiserum derived against the HU protein of S. gordonii ($\alpha HU_{Sg}$) is capable of recognizing other HU-like DNABII proteins. These results are consistent with the conservation of the secondary structure of the DNABII family beyond the modest primary sequence conservation. Intriguingly, $\alpha IHF_{Ec}$ and $\alpha HU_{Sg}$ fail to recognize the DNABII proteins HUα and HUβ of P. gingivalis ($\alpha HU\alpha_{Pg}$ and $\alpha HU\beta_{Pg}$, respectively) (FIG. 1). To date, this is the first time any antisera from one DNABII protein failed to cross-react with any other. Additionally, antisera derived against $\alpha HU\alpha_{Pg}$ and $\alpha HU\beta_{Pg}$ show no cross-reactivity with other DNABII proteins, recognizing only the proteins they were originally generated against. This suggests that the DNABII proteins of P. gingivalis are antigenically distinct when compared to other DNABII proteins, providing the opportunity to discern species-specific DNABII proteins within a bacterial community or biofilm.

Figure 2:
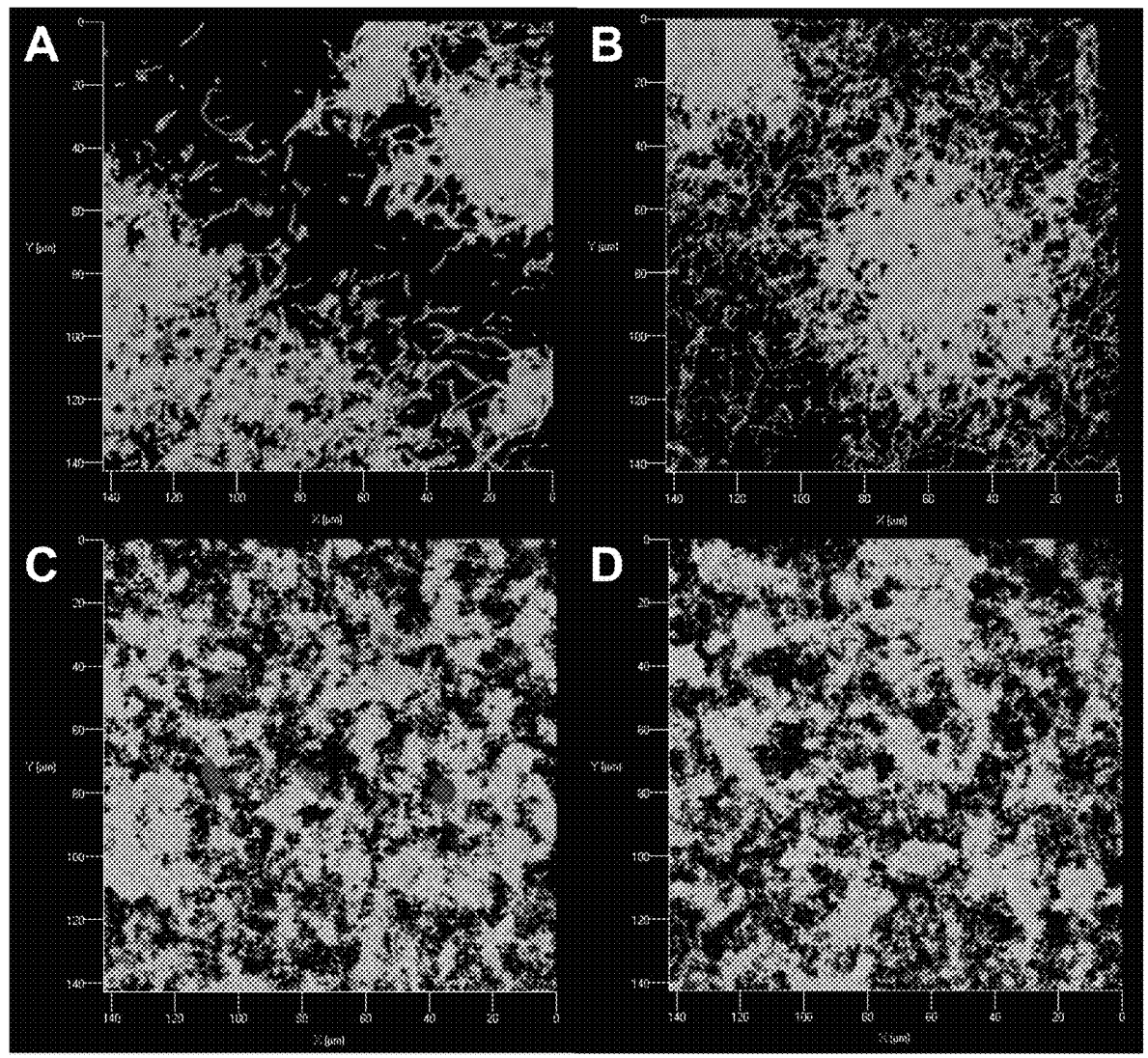
FIG. 2 depicts immunofluorescence microscopy of Sg biofilms probed with αHUSg (Panel A) or αHUβPg (Panel B) and Pg biofilms probed with αHUβPg (Panel C) and αHUSg (Panel D). Biofilms were grown for 24 hrs in THB+Hemin+menadione for Pg and CDM for Sg. Cells were stained with Styo-9, shown in white, and bound antibodies were labeled with a secondary antibody conjugated to Cy5 shown in red.

Immunofluorescence microscopy was performed on biofilms of S. gordonii and P. gingivalis in order to detect the presence of each species' DNABII proteins within the biofilms. Biofilms of S. gordonii and P. gingivalis were grown in vitro and then probed with $\alpha HU_{Sg}$, $\alpha HU\alpha_{Pg}$, or $\alpha HU\beta_{Pg}$ followed by a goat anti-rabbit secondary antibody conjugated to a fluorophore. CLSM imaging revealed that the S. gordonii biofilms had extensive labeling with the secondary antibody when the biofilms were probed with $\alpha HU_{Sg}$ (FIG. 2, Panel A) but not with antibodies against P. gingivalis DNABII proteins, (FIG. 2, Panel B). The biofilms of P. gingivalis had the greatest signal when probed with $\alpha HU\beta_{Pg}$ (FIG. 2, Panel C) but no fluorescence was seen when $\alpha HU_{Sg}$ was used (FIG. 2, Panel D). Use of the αHUα$_{Pg}$ resulted in no signal when either S. gordonii or P. gingivalis biofilms were tested. Taken together these results suggest that both S. gordonii and P. gingivalis have DNABII proteins present in the EPS of their respective biofilms, with the P. gingivalis biofilms relying on just the HUβ protein, not HUα.

As αIHF$_{Ec}$ has shown a differing ability to recognize DNABII proteins from S. gordonii and P. gingivalis (FIG. 1), experiments were performed to determine if the antigenic distinctiveness resulted in differing abilities to disrupt biofilms in these two species.

TABLE 2

The effects of antisera on biofilms of P. gingivalis and S. gordonii.

| | Species/Strain | | |
|---|---|---|---|
| Percent reduction in: | P. gingivalis | P. gingivalis ΔHUβ | S. gordonii |
| Anti-E. coli IHF | | | |
| Avg. thickness (μm) | <10% | <10% | 65%** |
| Biomass (μm$^3$/μm$^2$) | 15% | <10%. | 60%* |
| Anti-PgHUβ | | | |
| Avg. thickness (μm) | 45%*** | +30% | +15% |
| Biomass (μm$^3$/μm$^2$) | 45%*** | +30% | +15% |
| Anti-PgHUα | | | |
| Avg. thickness (μm) | +15% | +10% | 15% |
| Biomass (μm$^3$/μm$^2$) | +15% | +10% | <10% |
| Anti-SgHU | | | |
| Avg. thickness (μm) | <10% | <10% | 85%** |
| Biomass (μm$^3$/μm$^2$) | +15% | <10%. | 80%* |

P. gingivalis biofilms were grown for 40 hrs in THB supplemented with hemin (5 μg/ml) and menadione (1 μg/ml) in the presence of antisera.
S. gordonii was grown for 24 hrs in a chemically defined medium in the presence of antisera.
P- values for statistical significance indicated by asterisks *P ≤ 0.05, P ≤ 0.01, *P ≤ 0.001, **** P ≤ 0.0001.

COMSTAT analysis of in vitro grown biofilms revealed that the addition of αIHF$_{Ec}$ at a 1:25 dilution resulted in a significant decrease in the measured parameters of average thickness and total biomass of S. gordonii biofilms (Table 2). However, the antibody had no significant effects on biofilms of P. gingivalis. Additionally, the same parameters of S. gordonii biofilms were also reduced by the addition of αHU$_{Sg}$ antibody and, as with the αIHF$_{Ec}$ antibody, there was no effect on biofilms of P. gingivalis (Table 2). Conversely, when biofilms were treated with HUβ$_{Pg}$ antibodies only P. gingivalis biofilms were diminished while S. gordonii biofilms were unaffected. To demonstrate specificity of the αHUβ$_{Pg}$ antisera, biofilms were grown with of an HUβ deletion strain (PgΔHUβ). The αHUβ$_{Pg}$ antisera had no effect on PgΔHUβ biofilms, suggesting the ability of the antisera to disrupt biofilms is dependent on the ability to recognize the HUβ protein. Antisera derived against the HUα protein of P. gingivalis had no effect on either P. gingivalis or S. gordonii biofilms. Taken together, these results suggest that the HU protein from S. gordonii and the HUβ protein from P. gingivalis play important roles in the formation of biofilms in their respective species, while the HUα protein from P. gingivalis does not play a significant role.

Biofilms were grown in vitro and supplemented at seeding with 0.5 μM of DNABII protein from various homologous and heterologous sources.

TABLE 3

The effects of exogenous HU proteins on P. gingivalis and S. gordonii biofilms.

| Percent increase | Species/Strain | | |
|---|---|---|---|
| after the addition of: | P. gingivalis | P. gingivalis ΔHUβ | S. gordonii |
| E. coli IHF | | | |
| Avg. thickness (μm) | 25% | <10% | 195%** |
| Biomass (μm$^3$/μm$^2$) | 25% | <10% | 260%** |
| SgHU | | | |
| Avg. thickness (μm) | 15% | −25% | 50% |
| Biomass (μm$^3$/μm$^2$) | 15% | −20% | 75% |
| PgHUα | | | |
| Avg. thickness (μm) | 15% | −50% | <10% |
| Biomass (μm$^3$/μm$^2$) | 15% | −45% | <10% |
| PgHUβ | | | |
| Avg. thickness (μm) | <10% | −30% | 20% |
| Biomass (μm$^3$/μm$^2$) | <10% | −25% | 30% |

P. gingivalis biofilms were grown for 40 hrs in THB supplemented with hemin (5 μg/ml) and menadione (1 μg/ml) in the presence of 0.5 μM protein.
S. gordonii was grown for 24 hrs in a chemically defined medium in the presence of 0.5 μM protein.
P- values for statistical significance indicated by asterisks * P ≤ 0.05, P ≤ 0.01, * P ≤ 0.001, **** P ≤ 0.0001.

The addition of exogenous DNABII proteins to S. gordonii biofilms resulted in increases ranging from 25-300% for both the measured biomass and average thickness of the biofilm (Table 3). The HUα protein of P. gingivalis was an exception in that it had no effect on any of the biofilm parameters measured. In contrast to S. gordonii, addition of DNABII proteins to both P. gingivalis and the PgΔHUβ strain showed no significant effect on measured parameters. The lack of any significant effect on the PgΔHUβ strain is significant because deletion of the gene results in a significant decrease in biofilm formation.

TABLE 4

The effects of exogenous dsDNA on P. gingivalis and S. gordonii biofilms.

| | Amount of dsDNA Added | | | |
|---|---|---|---|---|
| | 1 μg/ml | 5 μg/ml | 10 μg/ml | 15 μg/ml |
| S. gordonii | | | | |
| Avg. thickness (μm) | <10% | 55%* | 10% | 25% |
| Biomass (μm$^3$/μm$^2$) | <10% | 55%* | <10% | 35% |
| P. gingivalis | | | | |
| Avg. thickness (μm) | 15% | −15% | −25% | −15% |
| Biomass (μm$^3$/μm$^2$) | 10% | −20% | −25% | −15% |
| P. gingivalis ΔHUβ | | | | |
| Avg. thickness (μm) | <10% | −20% | <10% | −30% |
| Biomass (μm$^3$/μm$^2$) | <10% | −20% | <10% | −30% |

P. gingivalis biofilms were grown for 40 hrs in THB supplemented with hemin (5 μg/ml) and menadione (1 μg/ml) in the presence of the indicated amounts of dsDNA.
S. gordonii was grown for 24 hrs in a chemically defined medium in the presence of the indicated amounts of dsDNA.
P- values for statistical significance indicated by asterisks *P ≤ 0.05,  P ≤ 0.01, * P ≤ 0.001, **** P ≤ 0.0001.

Titration of exogenous dsDNA from 1 to 10 ng/μl, in the form of calf thymus DNA, resulted in increases in S. gordonii biofilm biomass and average thickness when added at 5 ng/μl (Table 4). While both higher and lower concentrations had smaller, but not statistically significant effects on biofilm size. As with the addition of DNABII proteins, addition of dsDNA to both P. gingivalis and the PgΔHUβ mutant biofilms resulted in no significant change in the size of the biofilms.

TABLE 5

The effects of exogenous DNABII proteins and dsDNA on P. gingivalis and S. gordonii biofilms.

| Percent increase after the addition of dsDNA and: | Species/Strain | | |
|---|---|---|---|
| | P. gingivalis | P. gingivalis ΔHUβ | S. gordonii |
| E. coli IHF | | | |
| Avg. thickness (μm) | 15% | 35% | 390%*** |
| Biomass (μm³/μm²) | <10% | 40% | 495%*** |
| SgHU | | | |
| Avg. thickness (μm) | <10% | 15% | 685%**** |
| Biomass (μm³/μm²) | <10% | 15% | 845%**** |
| PgHUα | | | |
| Avg. thickness (μm) | −15% | <10% | <10% |
| Biomass (μm³/μm²) | −20% | <10% | <10% |
| PgHUβ | | | |
| Avg. thickness (μm) | <10% | 15% | 390%** |
| Biomass (μm³/μm²) | <10% | 15% | 485%** |

P. gingivalis biofilms were grown for 40 hrs in THB supplemented with hemin (5 μg/ml) and menadione (1 μg/ml) in the presence of 0.5 μM protein and 5 μg/ml dsDNA.
S. gordonii was grown for 24 hrs in a chemically defined medium in the presence of 0.5 μM protein 5 μg/ml dsDNA.
P- values for statistical significance indicated by asterisks * P ≤ 0.05, P ≤ 0.01, *P ≤ 0.001, ****P ≤ 0.0001.

According to our model, DNABII proteins and eDNA should work in concert, with the DNAII proteins stabilizing the meshwork of eDNA, allowing it to support the bacterial cells within. Indeed, increasing the extracellular levels of both DNABII proteins (0.5 μM) and calf thymus DNA (5 ng/μl) to S. gordonii biofilms resulted in 3 to 9-fold increases in the biomass and average thickness of the biofilms (Table 5). Interestingly, even the addition of both DNABII proteins and DNA had no ability to increase the size of the biofilms of P. gingivalis or its isogenic PgΔHUβ mutant.

Figure 3:
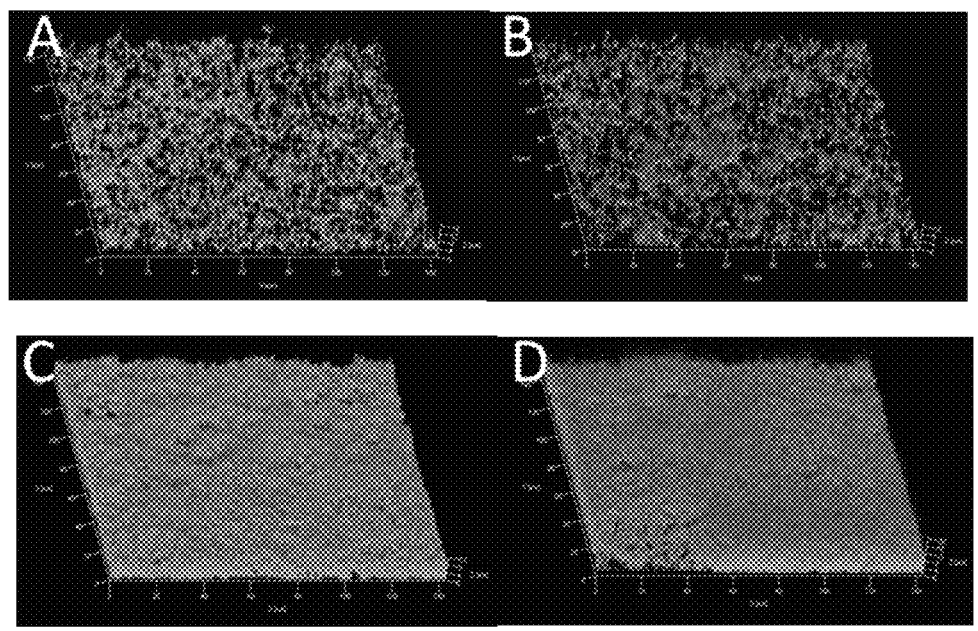
FIG. 3 shows functional complementation of HU proteins in *S. gordonii* and *P. gingivalis* biofilms. *S. gordonii* biofilms were treated with either naïve serum (A) or αHU$_{Sg}$ antisera and HUβ$_{Pg}$ protein (B) and then probed with αHUβ$_{Pg}$ antisera. *P. gingivalis* biofilms were treated with naïve serum (C) or αHUβ$_{Pg}$ antisera and HU$_{Sg}$ protein (D) and probed with αHU$_{Sg}$ antisera. As can be seen from the red fluorescence in Panels B and C, the non-native DNABII proteins were incorporated within the biofilms structures of the bacteria and no background fluorescence was detected when no protein was added (Panels A and C). The changes in the average thickness and biomass are plotted for both *S. gordonii* (Panel E) as well as *P. gingivalis* (Panel F) with the addition of the non-native protein resulting in significant increases in antibody treated biofilms, while the addition of a different DNA-binding protein (H—NS) had no effect. The increases in biofilms could also be reversed through the addition of antisera directed against the non-native protein.
Figure 3:
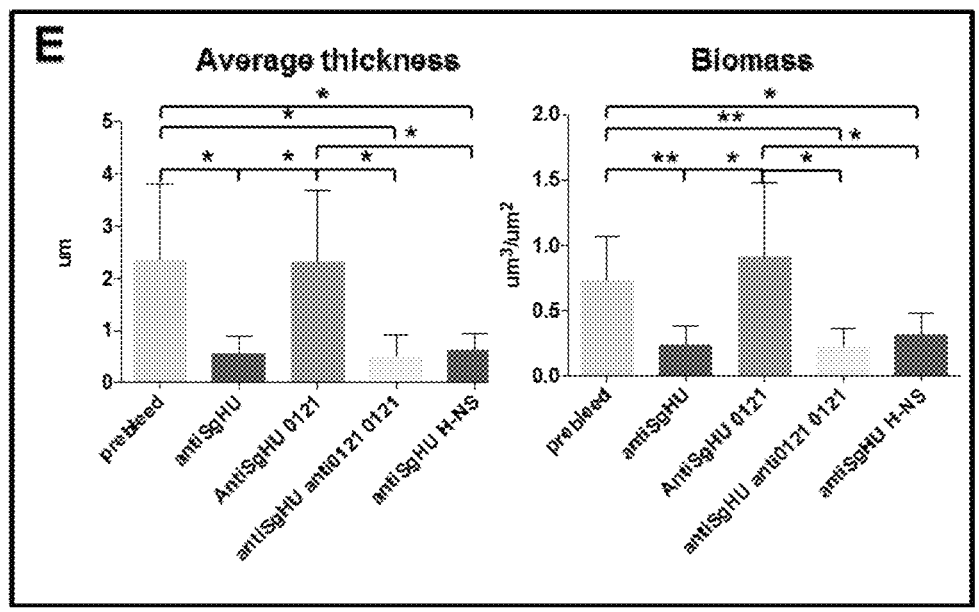

Having demonstrated the presence of DNABII proteins in the EPS of S. gordonii and P. gingivalis biofilms in vitro as well as their importance for the maintenance of the biofilm structure; we performed experiments to determine the ability of these DNABII proteins to functionally complement one another within a biofilm structure. Biofilms of S. gordonii were treated with αHU$_{Sg}$ to deplete the native S. gordonii DNABII proteins while being simultaneously supplemented with the antigenically distinct HUβ$_{Pg}$. Likewise, P. gingivalis biofilms were treated with αHUβ$_{Pg}$ while being simultaneously supplemented with HU$_{Sg}$. If these DNABII proteins are functionally equivalent within the EPS of different species, then addition of the second DNABII protein should functionally replace the protein lost from the EPS via depletion with the hetero-specific antibody. Indeed, addition of 0.5 HUβ$_{Pg}$ to S. gordonii biofilms treated with a 1:50 dilution of αHU$_{Sg}$ allowed for complete elimination of the effects of the antibodies on the biofilm. Addition of 0.5 μM HU$_{Sg}$ to P. gingivalis biofilms treated with a 1:50 dilution of αHUβ$_{Pg}$ also resolved the effects of the antisera on P. gingivalis biofilms. S. gordonii biofilm average thickness and biomass were reduced by ~70% with addition of antibody and returned to levels equivalent to untreated biofilms when HUβ$_{Pg}$ was present in the medium, while the ~30% decreases in P. gingivalis biofilm average thickness and biomass were eliminated when HU$_{Sg}$ was present. The effect was specific to the presence of the specific DNABII protein, as the non-typeable Haemophilus influenzae DNA-binding protein H—NS had no ability to recover the S. gordonii or P. gingivalis biofilms size. H—NS is a protein, which like the DNABII family of proteins, is within the class of proteins known nucleoid associated proteins (NAPs) and are all known to affect the global chromatin structure. Additionally, the effects of the HUβ$_{Pg}$ protein on S. gordonii could be removed through the concurrent addition of αHUβ$_{Pg}$ at a 1:50 dilution (FIG. 3, Panel E). While the effects of the HU$_{Sg}$ protein could be eliminated through the addition of αHU$_{Sg}$ (FIG. 3, Panel F). Immunofluorescence microscopy revealed that HUβ$_{Pg}$ protein and the HU$_{Sg}$ protein could be detected in recovered S. gordonii biofilms (FIG. 3, Panel B) and P. gingivalis biofilms (FIG. 3, Panel D).

Example 3—Dual-Species Biofilms

The oral cavity contains an array of bacterial species that coexist within biofilm communities. These communities contain both commensal bacteria, such as some oral streptococci, and other bacterial species, such as the periodontal pathogen Porphyromonas gingivalis. The ability of P. gingivalis to enter, persist, and expand within a preexisting biofilm depends on its ability to interact with the commensal bacteria present within the biofilm. One well-characterized binding partner of P. gingivalis is Streptococcus gordonii. Understanding how P. gingivalis interacts with S. gordonii and interfering with those interactions may allow exclusion or removal of this important periodontal pathogen from native biofilm communities within the oral cavity.

Applicants studied of the effects of targeting the DNABII proteins of an individual species within a multi-species biofilm. Dual-species biofilms of S. gordonii and P. gingivalis were used to test the ability of antisera derived against the P. gingivalis HUβ (αPgHUβ) protein to prevent dual-species biofilm formation and prevent P. gingivalis from entering into and expanding within a preexisting S. gordonii biofilm. Confocal microscopy was utilized to analyze the biofilm structure, and differential plating and immunofluorescence microscopy were used to determine the composition of the bacterial species present within the biofilms.

Pre-Treating Dual-Species Biofilms with Anti-DNABII Antibodies.

Figure 4:
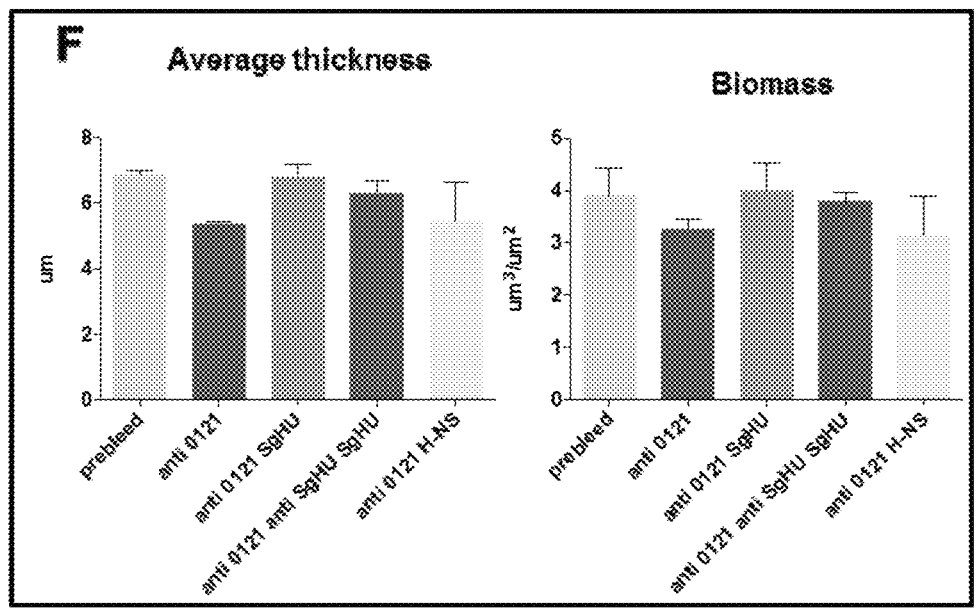
FIG. 4 shows the effects of anti-DNABII antisera added at seeding to dual species biofilms. Anti-SgHU antisera had no effect on the average thickness of a biofilm (Panel A) or on total biofilm biomass (Panel B) while anti-PgHUβ alone and anti-SgHU and anti-PgHUβ together reduced both biofilm parameters.
Figure 4:
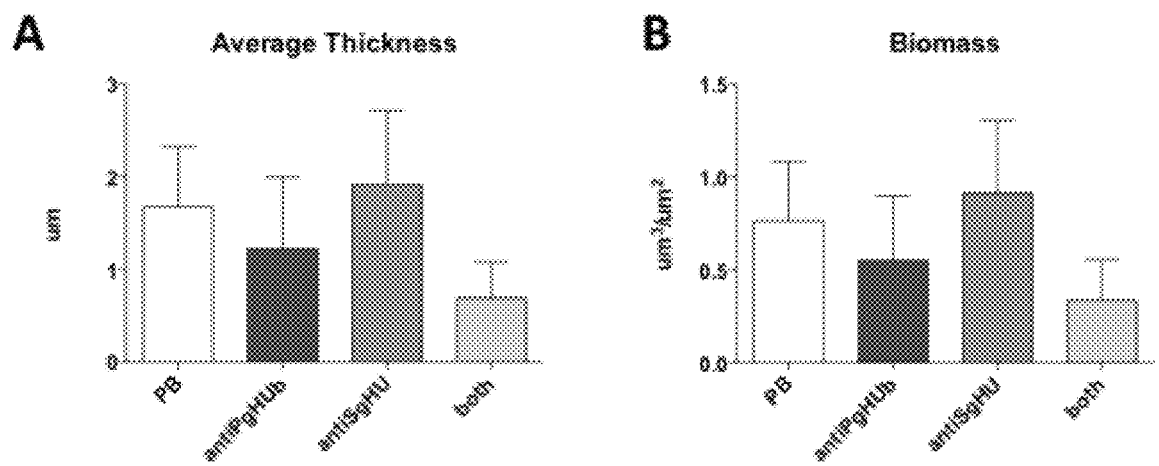

S. gordonii was grown overnight in THB medium and diluted to an OD$_{490}$=0.65 in THB. The culture was then diluted 1:4 in THB and grown at 37° C. until an OD$_{490}$=0.65 was reached again. The culture was then diluted 1:2500 into THBHK (THB supplemented with hemin and menadione) and used in Biofilm assays. P. gingivalis was grown anaerobically in THBHK medium to stationary phase. The culture was then diluted 1:2 in THBHK and grown for 6 hours before being diluted to an OD$_{490}$=0.1 in THBHK and used in biofilm assays. Antisera, or the corresponding prebleed control, were added to mixed cultures at a 1:50 dilution and biofilms were seeded in an 8 well chambered slide and grown at 37° C. anaerobically. After 24 h biofilms were stained, fixed, and imaged. COMSTAT analysis revealed that addition of anti-PgHUβ resulted a 30 percent decrease in both average thickness of the biofilm as well as biofilm biomass while addition of anti-SgHU antiserum had no effect on biofilm size. Addition of both anti-PgHUb and anti-SgHU at 1:50 dilutions of each antiserum resulted in a 60% decrease in average thickness and a 55% decrease in biofilm biomass (FIG. 4).

Preventing P. gingivalis from Entering Preformed S. gordonii Biofilms with Anti-PgHUβ Antiserum.

Figure 5:
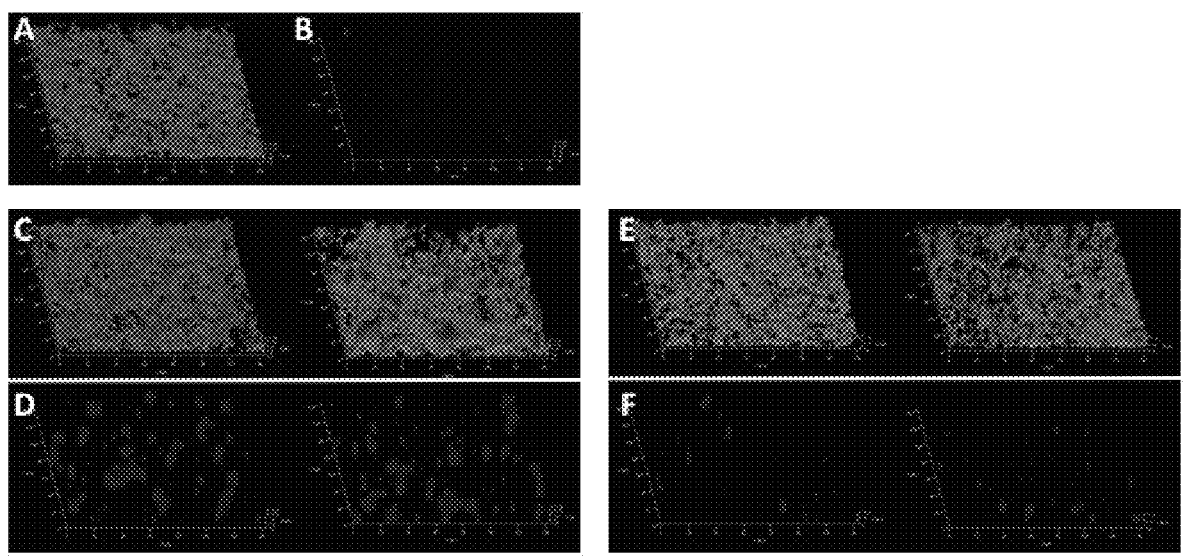
FIG. 5 depicts immunofluorescent microscopy of *S. gordonii* and *P. gingivalis* biofilms. *S. gordonii* biofilms alone had minimal signal when probed with anti-Pg fimbrial antisera (Panel A—while cell staining, Panel B—anti-Pg fimbrial immunofluorescence staining). Pretreatment of *P. gingivalis* with naive serum before addition to *S. gordonii* biofilms resulted in extensive immunofluorescence staining throughout the biofilm (Panels C, all cells—light gray; and D, *P. gingivalis* only—dark gray) while preincubation of *P. gingivalis* with anti-PgHUβ antisera resulted in large decreases in the amount of *P. gingivalis* present in the biofilms (Panels E; all cells—light gray and F; *P. gingivalis* only—dark gray).

Anti-PgHUβ antisera was tested for its ability to prevent *P. gingivalis* from entering into preformed *S. gordonii* biofilms. *S. gordonii* biofilms were grown for 24 hrs in a chemically defined medium in 8-well chambered slides and washed twice with sterile PBS before addition of *P. gingivalis*. *P. gingivlais* was grown as above and pre-incubated with a 1:50 dilution anti-PgHUβ for 30 min before addition to *S. gordonii* biofilms. Co-biofilms were grown for an additional 16 h anaerobically before being stained with CFSE and fixed. Fixed biofilms were then probed with antisera against *P. gingivalis* fimbrial proteins and a secondary antibody covalently labeled with a fluorescent probe. Biofilms were then imaged using confocal laser scanning microscopy to identify the presence of *P. gingivalis* within the biofilm. As can be seen in Figure B pretreatment of *P. gingivalis* with anti-PgHUβ antisera resulted in a large decrease in *P. gingivalis* within the biofilm (FIG. 5).

It was found that αPgHUβ reduced dual-species biofilm formation. The addition of both antisera reduced biofilm formation to an even greater extent. Additionally, pretreating *P. gingivalis* with αPgHUβ reduced the ability of the bacteria to enter into and expand within a preexisting *S. gordonii* biofilm.

Antisera derived against the *P. gingivalis* HUβ protein is a promising new tool for both reducing biofilms containing *P. gingivalis* within the oral cavity and preventing *P. gingivalis* from entering into preexisting biofilms, thereby reducing the ability of this important pathogen to cause disease.

EQUIVALENTS

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Eke P I, Dye B A, Wei L, Thornton-Evans G O, Genco R J, Cdc Periodontal Disease Surveillance workgroup: James Beck GDRP. Prevalence of periodontitis in adults in the United States: 2009 and 2010. Journal of dental research. 2012; 91(10):914-20. Epub 2012/09/01. doi: 10.1177/0022034512457373. PubMed PMID: 22935673.
2. Petersen P E, Ogawa H. Strengthening the prevention of periodontal disease: the WHO approach. Journal of periodontology. 2005; 76(12):2187-93. Epub 2005/12/08. doi: 10.1902/jop.2005.76.12.2187. PubMed PMID: 16332229.
3. Albandar J M. Epidemiology and risk factors of periodontal diseases. Dental clinics of North America. 2005; 49(3):517-32, v-vi. Epub 2005/06/28. doi: 10.1016/j.cden.2005.03.003. PubMed PMID: 15978239.
4. Choi J I, Nakagawa T, Yamada S, Takazoe I, Okuda K. Clinical, microbiological and immunological studies on recurrent periodontal disease. Journal of clinical periodontology. 1990; 17(7 Pt 1):426-34. Epub 1990/08/01. PubMed PMID: 2201704.
5. Lamont R J, Jenkinson H F. Life below the gum line: pathogenic mechanisms of *Porphyromonas gingivalis*. Microbiology and molecular biology reviews: MMBR. 1998; 62(4):1244-63. Epub 1998/12/05. PubMed PMID: 9841671; PMCID: 98945.
6. Grossi S G, Zambon J J, Ho A W, Koch G, Dunford R G, Machtei E E, Norderyd O M, Genco R J. Assessment of risk for periodontal disease. I. Risk indicators for attachment loss. Journal of periodontology. 1994; 65(3):260-7. Epub 1994/03/01. doi: 10.1902/jop.1994.65.3.260. PubMed PMID: 8164120.
7. Dzink J L, Socransky S S, Haffajee A D. The predominant cultivable microbiota of active and inactive lesions of destructive periodontal diseases. Journal of clinical periodontology. 1988; 15(5):316-23. Epub 1988/05/01. PubMed PMID: 3292595.
8. Hajishengallis G, Liang S, Payne M A, Hashim A, Jotwani R, Eskan M A, McIntosh M L, Alsam A, Kirkwood K L, Lambris J D, Darveau R P, Curtis M A. Low-abundance biofilm species orchestrates inflammatory periodontal disease through the commensal microbiota and complement. Cell host & microbe. 2011; 10(5):497-506. Epub 2011/11/01. doi: 10.1016/j.chom.2011.10.006. PubMed PMID: 22036469; PMCID: 3221781.
9. Hajishengallis G, Darveau R P, Curtis M A. The keystone-pathogen hypothesis. Nature reviews Microbiology. 2012; 10(10):717-25. Epub 2012/09/04. doi: 10.1038/nrmicro2873. PubMed PMID: 22941505; PMCID: 3498498.

10. Hajishengallis G, Lambris J D. Microbial manipulation of receptor crosstalk in innate immunity. Nature reviews Immunology. 2011; 11(3):187-200. Epub 2011/02/26. doi: 10.1038/nri2918. PubMed PMID: 21350579; PMCID: 3077082.
11. Darveau R P. Periodontitis: a polymicrobial disruption of host homeostasis. Nature reviews Microbiology. 2010; 8(7):481-90. Epub 2010/06/02. doi: 10.1038/nrmicro2337. PubMed PMID: 20514045.
12. Darveau R P. The oral microbial consortium's interaction with the periodontal innate defense system. DNA and cell biology. 2009; 28(8):389-95. Epub 2009/05/14. doi: 10.1089/dna.2009.0864. PubMed PMID: 19435427; PMCID: 2883565.
13. Slots J, Gibbons R J. Attachment of *Bacteroides melaninogenicus* subsp. *asaccharolyticus* to oral surfaces and its possible role in colonization of the mouth and of periodontal pockets. Infection and immunity. 1978; 19(1): 254-64. Epub 1978/01/01. PubMed PMID: 24002; PMCID: 414075.
14. Park Y, Simionato M R, Sekiya K, Murakami Y, James D, Chen W, Hackett M, Yoshimura F, Demuth D R, Lamont R J. Short fimbriae of *Porphyromonas gingivalis* and their role in coadhesion with *Streptococcus gordonii*. Infection and immunity. 2005; 73(7):3983-9. Epub 2005/06/24. doi: 10.1128/IAI.73.7.3983-3989.2005. PubMed PMID: 15972485; PMCID: 1168573.
15. Maeda K, Nagata H, Nonaka A, Kataoka K, Tanaka M, Shizukuishi S. Oral streptococcal glyceraldehyde-3-phosphate dehydrogenase mediates interaction with *Porphyromonas gingivalis* fimbriae. Microbes and infection/ Institut Pasteur. 2004; 6(13):1163-70. Epub 2004/10/19. doi: 10.1016/j.micinf.2004.06.005. PubMed PMID: 15488735.
16. Brinkmann V, Reichard U, Goosmann C, Fauler B, Uhlemann Y, Weiss D S, Weinrauch Y, Zychlinsky A. Neutrophil extracellular traps kill bacteria. Science. 2004; 303(5663):1532-5. doi: 10.1126/science.1092385. PubMed PMID: 15001782.
17. Jurcisek J A, Bakaletz L O. Biofilms formed by nontypeable *Haemophilus influenzae* in vivo contain both double-stranded DNA and type IV pilin protein. Journal of bacteriology. 2007; 189(10):3868-75. Epub 2007/02/27. doi: 10.1128/JB.01935-06. PubMed PMID: 17322318; PMCID: 1913342.
18. Novotny L A, Amer A O, Brockson M E, Goodman S D, Bakaletz L O. Structural stability of *Burkholderia cenocepacia* biofilms is reliant on eDNA structure and presence of a bacterial nucleic acid binding protein. PloS one. 2013; 8(6):e67629. Epub 2013/06/27. doi: 10.1371/journal.pone.0067629. PubMed PMID: 23799151; PMCID: 3682984.
19. Gustave J E, Jurcisek J A, McCoy K S, Goodman S D, Bakaletz L O. Targeting bacterial integration host factor to disrupt biofilms associated with cystic fibrosis. Journal of cystic fibrosis: official journal of the European Cystic Fibrosis Society. 2013; 12(4):384-9. Epub 2012/11/22. doi: 10.1016/j.jcf.2012.10.011. PubMed PMID: 23168017; PMCID: 3582735.
20. Lappann M, Claus H, van Alen T, Harmsen M, Elias J, Molin S, Vogel U. A dual role of extracellular DNA during biofilm formation of *Neisseria meningitidis*. Molecular microbiology. 2010; 75(6):1355-71. doi: 10.1111/j.1365-2958.2010.07054.x. PubMed PMID: 20180907.
21. Rouviere-Yaniv J, Gros F. Characterization of a novel, low-molecular-weight DNA-binding protein from *Escherichia coli*. Proceedings of the National Academy of Sciences of the United States of America. 1975; 72(9): 3428-32. Epub 1975/09/01. PubMed PMID: 1103148; PMCID: 433007.
22. Swinger K K, Rice P A. IHF and HU: flexible architects of bent DNA. Current opinion in structural biology. 2004; 14(1):28-35. Epub 2004/04/23. doi: 10.1016/j.sbi.2003.12.003. PubMed PMID: 15102446.
23. Pontiggia A, Negri A, Beltrame M, Bianchi M E. Protein H U binds specifically to kinked DNA. Molecular microbiology. 1993; 7(3):343-50.
24. Bonnefoy E, Takahashi M, Yaniv J R. DNA-binding Parameters of the H U Protein of *Escherichia coli* to Cruciform DNA. Journal of molecular biology. 1994; 242(2):116-29.
25. Kamashev D, Rouviere-Yaniv J. The histone-like protein H U binds specifically to DNA recombination and repair intermediates. The EMBO journal. 2000; 19(23):6527-35.
26. Rice P A, Yang S, Mizuuchi K, Nash H A. Crystal structure of an IHF-DNA complex: a protein-induced DNA U-turn. Cell. 1996; 87(7):1295-306. PubMed PMID: 8980235.
27. Goodman S D, Obergfell K P, Jurcisek J A, Novotny L A, Downey J S, Ayala E A, Tjokro N, Li B, Justice S S, Bakaletz L O. Biofilms can be dispersed by focusing the immune system on a common family of bacterial nucleoid-associated proteins. Mucosal immunology. 2011; 4(6):625-37. Epub 2011/07/01. doi: 10.1038/mi.2011.27. PubMed PMID: 21716265.
28. Brandstetter K A, Jurcisek J A, Goodman S D, Bakaletz L O, Das S. Antibodies directed against integration host factor mediate biofilm clearance from Nasopore. The Laryngoscope. 2013; 123(11):2626-32. Epub 2013/05/15. doi: 10.1002/lary.24183. PubMed PMID: 23670606; PMCID: 4060527.
29. Devaraj A, Justice S S, Bakaletz L O, Goodman S D. DNABII proteins play a central role in UPEC biofilm structure. Molecular microbiology. 2015. doi: 10.1111/mmi.12994. PubMed PMID: 25757804.
30. Brockson M E, Novotny L A, Mokrzan E M, Malhotra S, Jurcisek J A, Akbar R, Devaraj A, Goodman S D, Bakaletz L O. Evaluation of the kinetics and mechanism of action of anti-integration host factor-mediated disruption of bacterial biofilms. Molecular microbiology. 2014; 93(6):1246-58. Epub 2014/07/30. doi: 10.1111/mmi.12735. PubMed PMID: 25069521; PMCID: 4160410.
31. Priyadarshini R, Cugini C, Arndt A, Chen T, Tjokro N O, Goodman S D, Davey M E. The nucleoid-associated protein HUβ affects global gene expression in *Porphyromonas gingivalis*. Microbiology. 2013; 159(Pt 2):219-29.
32. van de Rijn I, Kessler R E. Growth characteristics of group A streptococci in a new chemically defined medium. Infection and immunity. 1980; 27(2):444-8. Epub 1980/02/01. PubMed PMID: 6991416; PMCID: 550785.
33. Bertani G. Studies on lysogenesis. I. The mode of phage liberation by lysogenic *Escherichia coli*. Journal of bacteriology. 1951; 62(3):293-300. PubMed PMID: 14888646; PMCID: PMC386127.
34. Bertani G. Lysogeny at mid-twentieth century: P1, P2, and other experimental systems. Journal of bacteriology. 2004; 186(3):595-600. PubMed PMID: 14729683; PMCID: PMC321500.
35. Tjokro N O, Rocco C J, Priyadarshini R, Davey M E, Goodman S D. A biochemical analysis of the interaction of *Porphyromonas gingivalis* HU PG0121 protein with DNA. PloS one. 2014; 9(3):e93266. Epub 2014/04/01. doi: 10.1371/journal.pone.0093266. PubMed PMID: 24681691; PMCID: 3969353.

What is claimed is:

1. A composition comprising a glycosidic polymer-based microsphere, wherein the glycosidic polymer has a diameter of 20 μm to 50 μm and comprises an insoluble cross-linked dextran and an effective amount of an isolated antibody or an antigen-binding fragment thereof that specifically recognizes or binds to a histone-like (HU) polypeptide of *Streptococcus gordonii* consisting of the amino acid sequence of SEQ ID NO: 12 and an effective amount of an isolated antibody or an antigen-binding fragment thereof that specifically recognizes or binds to a histone-like (HU) polypeptide of *Porphyromonas gingivalis* consisting of the amino acid sequence of SEQ ID NO: 11.

2. The composition of claim 1, wherein the glycosidic polymer comprises an alpha-1,6 linkage, an alpha-1,3 linkage, or a combination thereof.

3. The composition of claim 1, wherein the microsphere further comprises an antimicrobial agent.

4. The composition of claim 1, wherein each of the antibody and the antigen-binding fragment thereof does not recognize or bind to an isolated or recombinant integration host factor (IHF) protein.

5. The composition of claim 1, wherein the composition comprises a pharmaceutically acceptable carrier.

6. The composition of claim 5, wherein the composition is formulated as a chewable tablet, a dissolvable lozenge, a suspension, a gum, a gel, a toothpaste, in fluoride rinse, a mouthwash, a flavoring agent, a coloring agent, or a sustained-release formulation.

7. A glycosidic polymer-based microsphere comprising an insoluble cross-linked dextran having a diameter of 20 μm to 50 μm, wherein the microsphere is bound by an isolated antibody or an antigen-binding fragment thereof that specifically recognizes or binds to a histone-like (HU) polypeptide of *Streptococcus gordonii* consisting of the amino acid sequence of SEQ ID NO: 12 and an isolated antibody or an antigen-binding fragment thereof that specifically recognizes or binds to a histone-like (HU) polypeptide of *Porphyromonas gingivalis* consisting of the amino acid sequence of SEQ ID NO: 11.

8. A composition comprising an effective amount of the microsphere of claim 7 and a pharmaceutically acceptable carrier.

9. The composition of claim 8, wherein the composition is formulated as a chewable tablet, a dissolvable lozenge, a suspension, a gum, a gel, a toothpaste, a fluoride rinse, a mouthwash, a flavoring agent, a coloring agent, or a sustained-release formulation.

10. The composition of claim 7, wherein the glycosidic polymer comprises an alpha-1,6 linkage, an alpha-1,3 linkage, or a combination thereof.

11. The composition of claim 7, wherein each of the antibody and the antigen-binding fragment thereof does not recognize or bind to an isolated or recombinant integration host factor (IHF) protein.

12. A method of selectively inhibiting the growth of a biofilm on a surface comprising contacting the surface with an effective amount of the composition of claim 8, wherein the biofilm is formed by *Porphyromonas gingivalis*.

13. The method of claim 12, wherein the surface is the surface of a dental implant, teeth, or gingival tissues.

14. A method of selectively inhibiting or breaking down a biofilm in the oral cavity of a mammalian subject comprising administering to the oral cavity of the subject an effective amount of the composition of claim 5 or claim 8, wherein the biofilm is formed by *Porphyromonas gingivalis*.

15. The method of claim 14, wherein the mammalian subject has periodontitis.

* * * * *

UNITED STATES PATENT AND TRADEMARK OFFICE
CERTIFICATE OF CORRECTION

PATENT NO. : 11,690,892 B2
APPLICATION NO. : 15/952129
DATED : July 4, 2023
INVENTOR(S) : Bakaletz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 279 days.

Signed and Sealed this
Twelfth Day of November, 2024

Katherine Kelly Vidal
*Director of the United States Patent and Trademark Office*